United States Patent
Bryer et al.

(10) Patent No.: US 7,922,971 B2
(45) Date of Patent: Apr. 12, 2011

(54) INTEGRATED METER FOR ANALYZING BIOLOGICAL SAMPLES

(75) Inventors: Philip Bryer, Tarzana, CA (US); Irving Lee, Palo Alto, CA (US); Stephen J. Schoenberg, Auckland (NL); Lloyd M. Berken, Fremont, CA (US); Jean-Pierre Giraud, Paris (FR)

(73) Assignee: Abbott Diabetes Care Inc., Alameda, CA (US)

( * ) Notice: Subject to any disclaimer, the term of this patent is extended or adjusted under 35 U.S.C. 154(b) by 963 days.

(21) Appl. No.: 11/535,985

(22) Filed: Sep. 28, 2006
(Under 37 CFR 1.47)

(65) Prior Publication Data
US 2008/0167578 A1    Jul. 10, 2008

Related U.S. Application Data

(60) Provisional application No. 60/741,019, filed on Nov. 30, 2005.

(51) Int. Cl.
*C12Q 1/68* (2006.01)
*G01N 33/48* (2006.01)
*G01N 33/00* (2006.01)
*A61B 5/00* (2006.01)

(52) U.S. Cl. ........... 422/50; 422/68.1; 436/95; 436/128; 600/300; 600/583

(58) Field of Classification Search ............ 422/50, 422/68.1; 600/583, 300; 436/95, 128
See application file for complete search history.

(56) References Cited

U.S. PATENT DOCUMENTS

| | | | |
|---|---|---|---|
| 4,895,147 | A | 1/1990 | Bodicky et al. |
| 5,279,294 | A | 1/1994 | Anderson et al. |
| 5,487,748 | A | 1/1996 | Marshall et al. |
| 5,971,941 | A | 10/1999 | Simons et al. |
| 6,129,823 | A | 10/2000 | Hughes et al. |
| 6,315,738 | B1 | 11/2001 | Nishikawa et al. |
| 6,377,894 | B1 | 4/2002 | Deweese et al. |
| 6,541,216 | B1 | 4/2003 | Wilsey et al. |
| 6,561,989 | B2 | 5/2003 | Whiton |
| 6,670,115 | B1 | 12/2003 | Zhang |
| 6,783,502 | B2 | 8/2004 | Orloff et al. |
| 6,939,450 | B2 | 9/2005 | Karinka et al. |
| 7,118,667 | B2 | 10/2006 | Lee |
| 7,299,081 | B2 | 11/2007 | Mace et al. |
| 2002/0002344 | A1 | 1/2002 | Douglas et al. |
| 2003/0068666 | A1 | 4/2003 | Zweig |
| 2003/0191415 | A1 | 10/2003 | Moerman et al. |
| 2003/0209451 | A1 | 11/2003 | Dineen et al. |
| 2003/0211619 | A1 | 11/2003 | Olson et al. |

(Continued)

OTHER PUBLICATIONS

Notification of Transmittal of the International Search Report and the Written Opinion of the International Searching Authority, or the Declaration, in PCT Application No. PCT/US2007/079778, paper dated Mar. 5, 2008, 16 pages.

*Primary Examiner* — Jill Warden
*Assistant Examiner* — Dean Kwak
(74) *Attorney, Agent, or Firm* — Edward J. Baba; Marcus T. Hunt; Bozicevic, Field & Francis LLP

(57) ABSTRACT

Analyte monitoring devices and methods therefore are provided. The devices integrate various functions of analyte monitoring, e.g., sample acquisition and testing.

26 Claims, 59 Drawing Sheets

U.S. PATENT DOCUMENTS

| | | |
|---|---|---|
| 2003/0212345 A1* | 11/2003 | McAllister et al. ........... 600/584 |
| 2004/0134779 A1 | 7/2004 | Hsu et al. |
| 2005/0234368 A1* | 10/2005 | Wong et al. ................... 600/583 |
| 2005/0277850 A1 | 12/2005 | Mace et al. |
| 2006/0094985 A1 | 5/2006 | Aceti et al. |
| 2006/0229532 A1 | 10/2006 | Wong et al. |
| 2007/0149897 A1 | 6/2007 | Ghesquiere et al. |
| 2007/0173739 A1* | 7/2007 | Chan ............................. 600/583 |
| 2007/0287191 A1 | 12/2007 | Stiene et al. |
| 2008/0039946 A1 | 2/2008 | Zucherman et al. |
| 2008/0039949 A1 | 2/2008 | Meesenburg et al. |
| 2008/0167578 A1 | 7/2008 | Bryer et al. |
| 2009/0321287 A1* | 12/2009 | List et al. ...................... 206/223 |

* cited by examiner

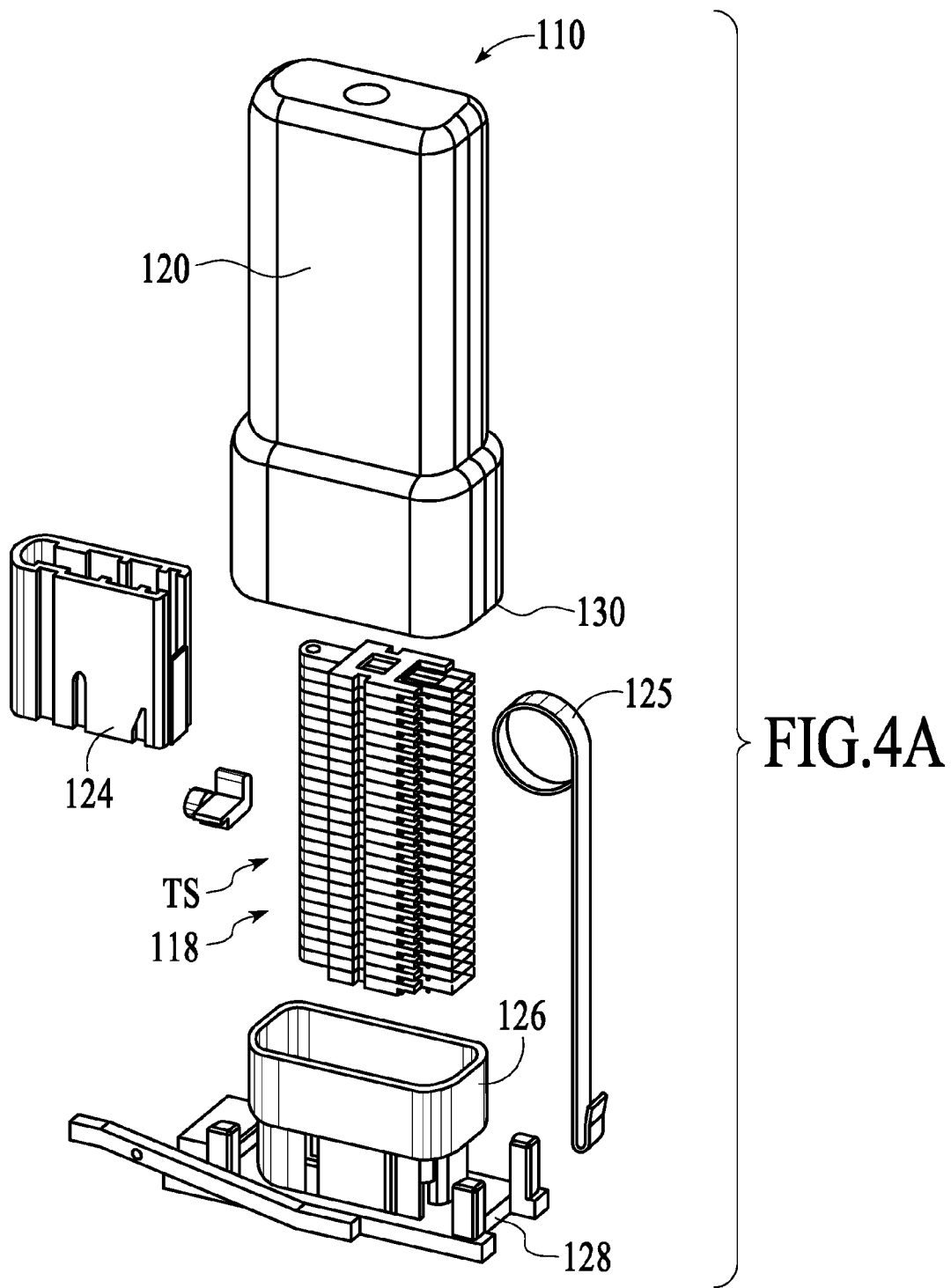

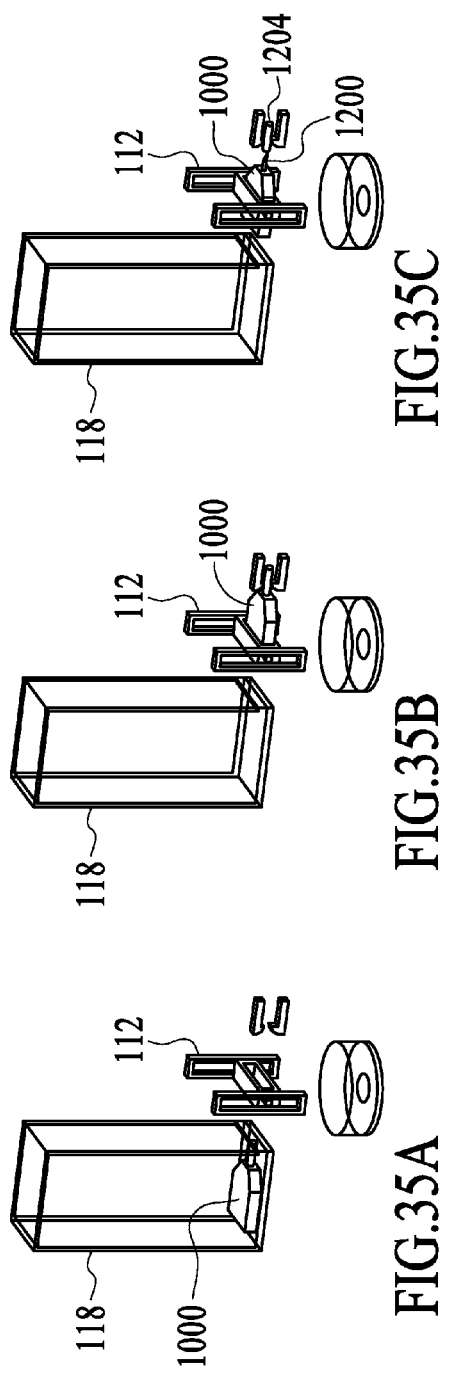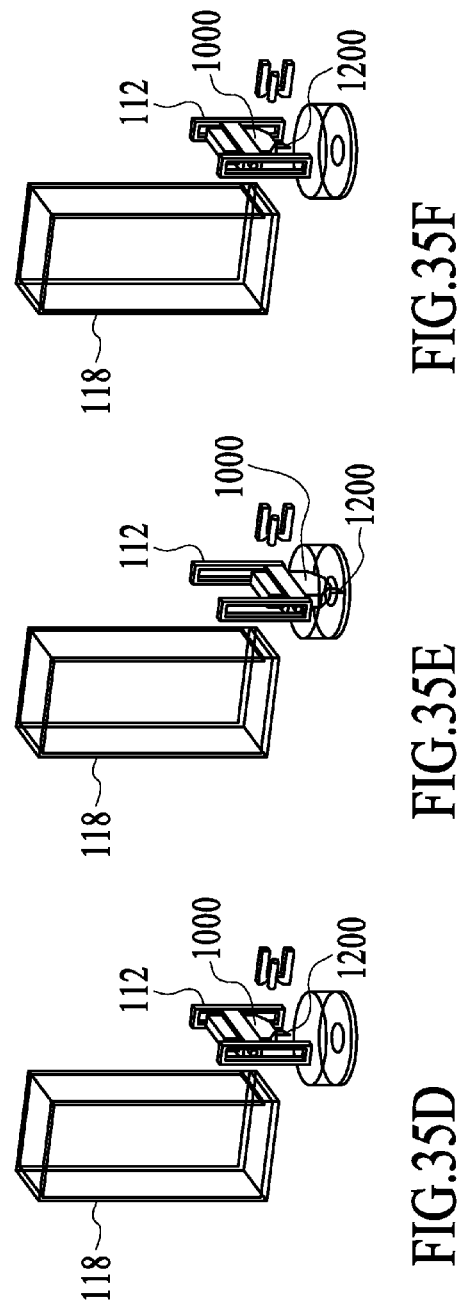

INTEGRATED METER FOR ANALYZING BIOLOGICAL SAMPLES

PRIORITY

This application claims the benefit of priority to U.S. provisional patent application No. 60/741,019, filed Nov. 30, 2005, which is hereby incorporated by reference. This application is related to a contemporaneously-filed application entitled Integrated Sensor for Analyzing Biological Samples, and a contemporaneously-filed design application, by the same Assignee.

BACKGROUND OF THE INVENTION

1. Field of the Invention

This invention relates to the field of medical diagnostic devices.

2. Discussion of the Art

The prevalence of diabetes is increasing markedly in the world. At this time, diagnosed diabetics represent about 3% of the population of the United States. It is believed that the actual number of diabetics in the United States is much higher. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse some of the effects of diabetes.

Analyte, e.g., glucose, monitoring devices known in the art have operated on the principle of taking blood from an individual by a variety of methods, such as by means of a needle or a lancet. The individual then coats a paper strip carrying reagents with the blood, and finally inserts the blood coated strip into a blood glucose meter for measurement of glucose concentration by optical or electrochemical techniques.

Medical devices of the prior art for monitoring the level of glucose in the blood stream have required that an individual have separately available a needle or a lancet for extracting blood from the individual, test strips carrying reagents for bringing about a chemical reaction with the glucose in the blood stream and generating an optical or electrochemical signal, and a blood glucose, meter for reading the results of the reaction, thereby indicating the level of glucose in the blood stream. The level of glucose, when measured by a glucose, meter, is read from the strip by an optical or electrochemical meter.

It is desired to simplify the systems, devices, and methods for determining the level of an analyte such as glucose in a body fluid such as blood. In particular, it is desired to integrate the operations of extracting a sample of blood by means of a needle or a lancet, applying the sample of blood to a reagent-bearing test strip, reading the result of a glucose, monitoring test, and discarding the used needle or lancet and test strip in a safe and efficient manner.

Certain patents describe devices that can perform steps of determining the concentration of glucose in the blood stream. For example, U.S. Pat. No. 5,632,410 discloses a sensor-dispensing instrument for handling a plurality of fluid sensors (i.e., test strips). However, this patent fails to include a lancing device for puncturing the skin of a patient in order to extract a sample of blood. U.S. Pat. No. 6,908,008 discloses an apparatus that includes a dispenser comprising a housing having a chamber; a means for retaining a plurality of test strips in a substantially moisture-proof, air-tight first position; and a means for opening the chamber and moving one of the plurality of test strips translationally from a first position inside of the chamber to a second position at least partially outside of the chamber, wherein the opening of the chamber and the moving of the one test strip is achieved by a single mechanical motion; and an electrochemical analyzing means for analyzing a biological fluid. However, like, U.S. Pat. No. 5,632,410, this patent fails to simplify the testing process, e.g., this patent fails to include a lancing device for puncturing the skin of a patient in order to extract a sample of blood.

In addition, U.S. Pat. No. 5,035,704 discloses a blood sampling mechanism including a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, means for defining a blood sampling station at which the blood sample is obtained, means for defining a blood testing station at which the blood sample is tested by said blood sample testing means, and means for conveying said test pad from said blood sampling station after the blood sample has been obtained to said blood testing station. The dermis-piercing member and test pad are, however, entirely separate components in this system (see also WO 03/082091).

U.S. Pat. No. 5,971,941 discloses a blood sampling apparatus for sampling blood from the skin of a patient for analysis. The apparatus includes a cartridge and a housing with a driver. The cartridge has a cartridge case, lancet, and a compartment associated with the cartridge case for receiving blood. The lancet is housed in the cartridge case and operatively connected thereto such that it is drivable to extend outside the cartridge case through a lancing opening for lancing the skin to yield blood. The housing has a driver for urging the lancet to extend outside the cartridge case. During lancing, the cartridge may be detachably held in the housing such that the cartridge can be disassociated from the driver after sampling blood. The U.S. Pat. No. 5,971,941 patent discloses that material around a lancet aperture in a cartridge case soaks up blood after lancing (see also U.S. Pat. No. 5,279,294). This does not bring the absorbent material to the center of the sample, and when only a small amount of blood is available such as is often the case in alternate site testing away from fingertips, then testing may be unreliable, may need to be repeated far too often, or may simply require testing at the fingertips. Application of sample fluid to a capillary end leading to reagent material involves careful manual alignment. A manual actuation step is also involves in getting the lancet to protrude from the cartridge.

WO 2004/041082 discloses a device for use with a body fluid sampling device for extracting bodily fluid from an anatomical feature. The device comprises a cartridge having a plurality of cavities. The device may include a plurality of penetrating members each at least partially contained in the cavities of the cartridge wherein the penetrating members are slidably moved to extend outward from openings on the cartridge to penetrate tissue. The device may also include a plurality of analyte detecting members and a plurality of chambers. Each chamber may be associated with one of the cavities, the chambers positioned along an outer periphery of the cartridge, wherein at least one of the analyte detecting members forms a portion of one wall of one of the plurality of chambers.

SUMMARY OF THE INVENTION

It would be desirable to develop a medical diagnostic device that (1) stores and dispenses lancets and sensors as integrated striplets including a lancet and test sensor each protruding from a lancet body or coupled directly thereto, (2) forms an opening with the lancet in the skin of a patient to enable a sample of biological liquid to emerge from the patient, (3) reorients the striplet for collecting the sample of biological liquid from the patient emerging from the opening in the skin by means of the test strip, (4) analyzes the sample of biological liquid to determine a characteristic of the biological liquid, and (5) ejects the used test strip in a safe manner. It would also be desirable to develop a medical diagnostic device that is small in size, reliable to use, and provides accurate results, even when only a small volume of sample of biological liquid is collected.

An analyte monitoring apparatus is provided. An example is a glucose monitoring apparatus. The apparatus includes a housing with a user interface having one or more switches or a display or both. One or more analyte testing striplets are contained in the housing that include both a lancet and a test sensor. A lancing and testing port is defined in the housing for permitting the striplet to contact a lancing site outside the housing. A set of mechanical components serve to load a striplet for a lancing and testing process, advance the striplet for lancing through the port at a lancing site proximate to the port, and re-orient and advance the striplet for testing at the lancing site also through the port. An analyzer determines an analyte level, e.g., a glucose, level, of a body fluid, e.g., blood, applied to the test sensor from the lancing site.

The monitoring apparatuses are configured for analysis (e.g., concentration determination) of an analyte in a sample of body fluid, wherein certain embodiments the apparatuses are configured to determine the concentration of an analyte in a small volume of sample, e.g., less than about 1 microliter, e.g., less than about 0.5 microliters, e.g., less than about 0.2 microliters, e.g., about 0.1 microliters or less. The monitoring apparatuses may be configured for analysis of an analyte in a volume of sample by, for example, coulometry, amperometry, and/or potentiometry. In certain embodiments, the monitoring apparatuses are configured for optical analysis of an analyte in a sample.

A striplet includes both a test strip portion and a lancet portion. These may be relatively opposed, e.g., extending about 180 degrees from each other, or extending at another angle from zero to 360 degrees. The lancet portion may couple to the test strip portion as a two-piece device, or each may couple with a lancet body as a three-piece device.

A cartridge that is coupled within a compartment of the housing may contain several striplets. The cartridge may include a guide rail for relative positioning within the housing with respect to the set of mechanical components. The guide rail having a stopping point which precisely locates the cartridge relative to the housing, and wherein the cartridge remains due to said guide rail and stopping point when said seal is temporarily broken for loading the striplet. A seal may generally maintain the striplets within the cartridge free from exposure to ambient air, and be configured for releasing the seal temporarily to permit loading of a striplet for a lancing and testing process. The seal may be elastomeric and/or include a bellows. In this sense, a bellows may be understood as a container which is deformable in such a way as to alter its volume, or a portion of a container that includes a pleated or expansible part and/or a length or direction adjustable element, which may be tubular or connecting one plane; in collapsible devices or applications permitting good sealing. The cartridge may include a biasing member for providing the striplets at a loading end of the cartridge. One or more structural supports or inserts may be included within the cartridge for structural support of the striplets within the cartridge, and also for desiccating an interior of the cartridge to keep the striplets substantially free of moisture. The one or more inserts may include a hard plastic insert for providing the structural support and a desiccating plastic insert for providing the desiccating. Desiccating may also be provided separately.

The set of mechanical components includes a striplet slot for holding the striplet during re-orientation which includes rotation of the striplet. The striplet slot may be coupled with a cam that oscillates, and in certain embodiments about a point of unstable equilibrium, although in a particular embodiment having a localized point of stability at or near its center or somewhere within its range of motion, between points corresponding to different orientations of the striplet for lancing and testing.

The lancet and analyte test sensor may each be coupled to a lancet body, and may protrude from the lancet body. The striplets may further include a lancet cap protecting the protruding lancet. A lancet cap compartment may serve to remove the lancet cap, e.g., by grabbing it more tightly than it is being held covering the lancet, when the lancet cap is positioned into the compartment. The lancet cap compartment may provide a space and a frictional force for holding the lancet cap during a lancing and testing process, and may provide the lancet cap back to re-cover the lancet for safe ejection of a used striplet.

The set of mechanical components may include first and second component subsets. The first mechanical subset includes a first set of gears within the housing, which, along with a cartridge housing and tub combination, a pusher, striplet track and turret including a rotatable striplet slot, and an ejection port in the housing, are respectively for unsealing the tub with the cartridge housing, advancing a striplet to the turret, and ejecting the striplet after testing. The second mechanical subset includes a second set of gears within the housing, which, along with a blade and mating lancet cap contour, the turret, and a carriage which contains the turret, are respectively for arming/disarming the lancet by removing/replacing the lancet cap over the lancet, re-orienting the striplet between lancing and testing, and performing both lancing and testing through the lancing and testing port when a user provides the lancing site proximate to the port.

The arming including removing the optional lancet cap may be deemed to also involve the first subset in an embodiment wherein the pusher couples with the lancet cap and pulls both the blade and lancet cap away from the striplet in a retreating motion. The disarming may include replacing the lancet cap for safe ejection of a used testing striplet through a separate striplet ejection port or through the same lancing and testing port. The pusher may contact and move the striplet along the striplet track until the striplet is disposed within the turret, while both the lancing and the testing may occur by movement of the carriage relative to the rest the apparatus. The lancing and the testing may occur by same or similar movements of the carriage due to the re-orienting of the striplet by rotating the turret by 180 degrees, or by whatever angle at which the testing component and lancing component of the striplet are relatively disposed.

The re-orienting of the striplet may include rotating and/or flipping the striplet.

A transmission system may be included for orienting the lancing/collecting assembly in a first position, whereby the lancet can be used to form an opening in the skin of a patient, and in a second position, whereby the test sensor can be used to collect a sample of biological liquid from the patient.

A analyte, e.g., glucose, monitoring apparatus is further provided including a user interface coupled with a housing including one or more switches or a display or both. Multiple analyte, e.g., glucose, testing striplets include both a lancet and an analyte test sensor. A cartridge contains multiple striplets for loading into the housing within a cartridge compartment, wherein the cartridge includes at least one guide rail for relative positioning within the housing. The seal generally maintains the striplets within the cartridge free from exposure to ambient air, and is configured for releasing the seal temporarily to permit loading of a striplet for a lancing and testing process. One or more lancing and testing ports are defined in the housing for permitting the striplet to contact a lancing site outside the housing. A set of mechanical components load a striplet for a lancing and testing process, advance the striplet for lancing at a lancing site, and also advance the striplet for testing at said lancing site, via the one or more lancing and testing ports. An analyzer determines a analyte, e.g., glucose, level of a body fluid applied to the test sensor from the lancing site.

The seal may be elastomeric and/or include a bellows. The guide rail may have a stopping point which precisely locates the cartridge relative to the housing. The cartridge may remain stationary relative to the housing due to the guide rail and stopping point when the seal is temporarily broken for loading the striplet. The cartridge may include a biasing member for urging the striplets to be loaded from the loading end of the cartridge. One or more structural supports and/or inserts within the cartridge may be for structural support of the striplets within the cartridge, and/or for desiccating an interior of the cartridge to keep the striplets substantially free of moisture. These may include a hard plastic insert for providing said structural support and a desiccating plastic insert for providing the desiccating.

A further analyte monitoring apparatus is provided with a housing having a user interface that includes one or more switches or a display or both. Multiple analyte testing striplets that include both a lancet and a test sensor are contained within a cartridge that is loaded into the housing within a cartridge compartment. One or more structural supports or inserts are provided within the cartridge for structural support of the striplets within the cartridge, and for desiccating an interior of the cartridge to keep the striplets substantially free of moisture. One or more lancing and testing ports are defined in the housing for permitting the striplet to contact a lancing site outside the housing. A set of mechanical components automatically load the striplet for a lancing and testing process, advance the striplet for lancing and for testing at a lancing site upon re-orienting via the one or more lancing and testing ports. An analyzer determines an analyte level, e.g., a glucose level, of a body fluid applied to the test sensor from the lancing site.

The one or more structural supports or inserts include a hard plastic insert for providing structural support and a desiccating plastic insert for providing desiccation. The cartridge may include one or more guide rails for relative positioning within the housing. The guide rail may have a stopping point which precisely locates the cartridge relative to the housing, such that the cartridge remains stationary relative to the housing when the seal is temporarily broken for loading a striplet for lancing and testing. The seal generally maintains the striplets within the cartridge free from exposure to ambient air, and is configured for releasing temporarily to permit loading of a striplet for a lancing and testing process. This apparatus can include other features described elsewhere hereinabove or below.

A further analyte monitoring apparatus is provided. This apparatus may include many of the features already recited hereinabove. A set of mechanical components includes first and second subsets respectively including first and second sets of gears. The first subset, along with a lancet cap compartment, a striplet track and a rotatable slot, are respectively for arming/disarming the lancet, loading a striplet for a lancing and testing process, and re-orienting the striplet between lancing and testing for performing both lancing and testing through a lancing and testing port when a user provides the lancing site proximate to the port. The second mechanical subset includes a second set of gears within the housing, which, along with a pusher, are for advancing the striplet though the port to the lancing site for both lancing and testing upon re-orienting.

Alone or in combination with one or more other features recited above and/or below herein, an assembly is also provided for storing and dispensing test strips, wherein each test strip includes a lancet-containing portion and a sensor-containing portion. The assembly includes an exterior cover, an interior housing, a platform for containing a biasing element, an insert for securing the biasing element, a test strip track for providing a guide path for an assembly for forming an opening in the skin of a patient and collecting a sample of biological liquid emerging from the skin of the patient, a biasing member for urging the test strips toward the test strip track, and an element for advancing a test strip from the assembly to the assembly for forming an opening in the skin of a patient and collecting a sample of biological liquid emerging from the skin of the patient.

The test strips are advanced, one at a time, to the assembly for forming an opening in the skin of a patient and collecting a sample of biological liquid emerging from the skin of the patient by a pushing element. A seal ensures a substantially moisture-tight, air-tight condition in the assembly for storing and dispensing a plurality of test strips. A bellows or elastomerically-composed seal ensures a substantially moisture-tight, air-tight condition in the assembly for storing and dispensing test strips. A door ensures a substantially moisture-tight, air-tight condition in the assembly for storing and dispensing test strips.

In further embodiments, an apparatus is provided whereby a test strip or a lancet is applied through a testing or lancing port, followed by re-orienting and ejection through an ejection port. According to one or these embodiments, an analyte monitoring apparatus includes a housing; a user interface coupled with the housing including one or more switches or a display or both; one or more analyte test strips; a testing port defined in the housing for permitting the strip to contact a testing site outside the housing; an ejection port separate from the testing port for disposing of the strip after testing; a set of mechanical components for loading a strip for a testing process, for advancing the strip for testing through said testing port at the testing site proximate to the port, for re-orienting the strip after testing, and for ejecting the strip through the ejection port; and an analyzer for determining a glucose or other analyte level of a body fluid applied to the test strip from the lancing site.

A cartridge may be coupled into a slot in the housing which contains several strips. A seal may generally maintain the strips within the cartridge free from exposure to ambient air, and may be configured for releasing the seal temporarily to permit loading of a strip for a testing process. The cartridge may have a structural support for the strips within the cartridge. The cartridge may include a desiccating member for keeping the strips substantially free of moisture. The set of mechanical components may include a strip turret for holding the strip at least during the re-orienting which includes rotation of the strip in certain embodiments.

In another of these further embodiments, an analyte monitoring apparatus includes a housing; one or more lancets; a lancing port defined in the housing for permitting a lancet to contact a lancing site outside the housing; a separate ejection port for disposing of the lancet after testing; and a set of mechanical components for loading a lancet for a lancing process, for advancing the lancet for lancing through said lancing port at the lancing site proximate to the port, for re-orienting the lancet after lancing, and for ejecting the lancet through the ejection port.

The apparatus may further include a user interface coupled with the housing including one or more switches or a display or both; one or more test strips; and an analyzer for determining an analyte level of a body fluid applied to the test strip from the lancing site. The apparatus may also include a cartridge coupled into a slot in the housing which contains several lancets. The cartridge may include a structural support for the lancets within the cartridge. A set of mechanical components may include a lancet turret for holding the lancet at least during the re-orienting which includes rotation of the lancet in certain embodiments.

BRIEF DESCRIPTION OF THE DRAWINGS

FIG. 4A is an exploded perspective view of the assembly for storing and dispensing test striplets shown in FIG. 3A.

FIG. 5A shows the assembly in a sealed condition. FIG. 5B shows the assembly in an unsealed condition.

In FIG. 10B, the hidden side of a drive gear is shown.

FIGS. 35A-35M, inclusive, are schematic views illustrating the positions of the lancing/collecting assembly of an alternative embodiment during one cycle of operation of the medical diagnostic device of an alternative embodiment.

DETAILED DESCRIPTION OF PREFERRED AND ALTERNATIVE EMBODIMENTS

Figure 1:
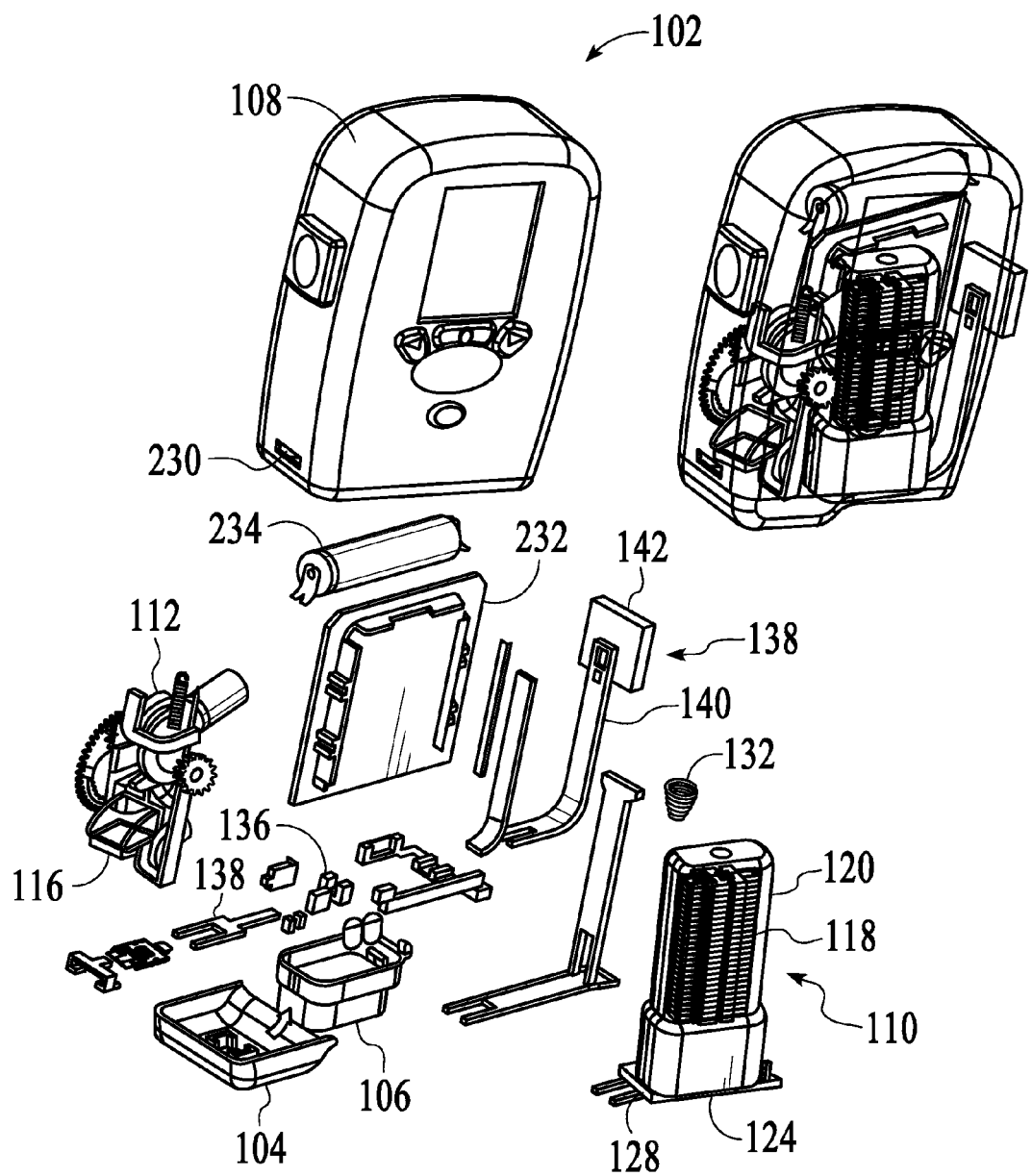
FIG. 1 is an exploded perspective view of one embodiment of the medical diagnostic device.

As used herein, the expressions "storing/dispensing assembly" and "assembly for storing and dispensing test strips" means a mechanism that is capable of both (a) storing a plurality of test strips in a magazine and (b) advancing the test strips, one at a time, from the magazine to the lancing/collecting assembly. The expression "lancing/collecting assembly" means a mechanism that is capable of both (a) forming an opening in the skin of a patient and (b) collecting a sample of biological liquid emerging from that opening.

Medical Diagnostic Device

Referring now to FIGS. 1 and 2A-2C, the medical diagnostic device 100, 100a in accordance with certain embodiments includes a housing 102, 102a. The device 100 may have an end cap 104, a tub 106, and a protective cover 108 for the subsystems and assemblies located with the housing 102, as in the embodiment of FIG. 1. Within the housing 102 is located an assembly for storing and dispensing test strips 110, a lancing/collecting assembly 112, an assembly 114 for removing a protective cover from the tip of a lancet and re-attaching the protective cover to the tip of a used lancet, and an analyzer 116. The end cap 104 has an opening 117, through which a lancet can be projected for forming an opening in the skin of a patient, and through which a sensor can be projected for collecting a sample of biological liquid emerging from the opening in the skin of the patient.

Figure 2A:
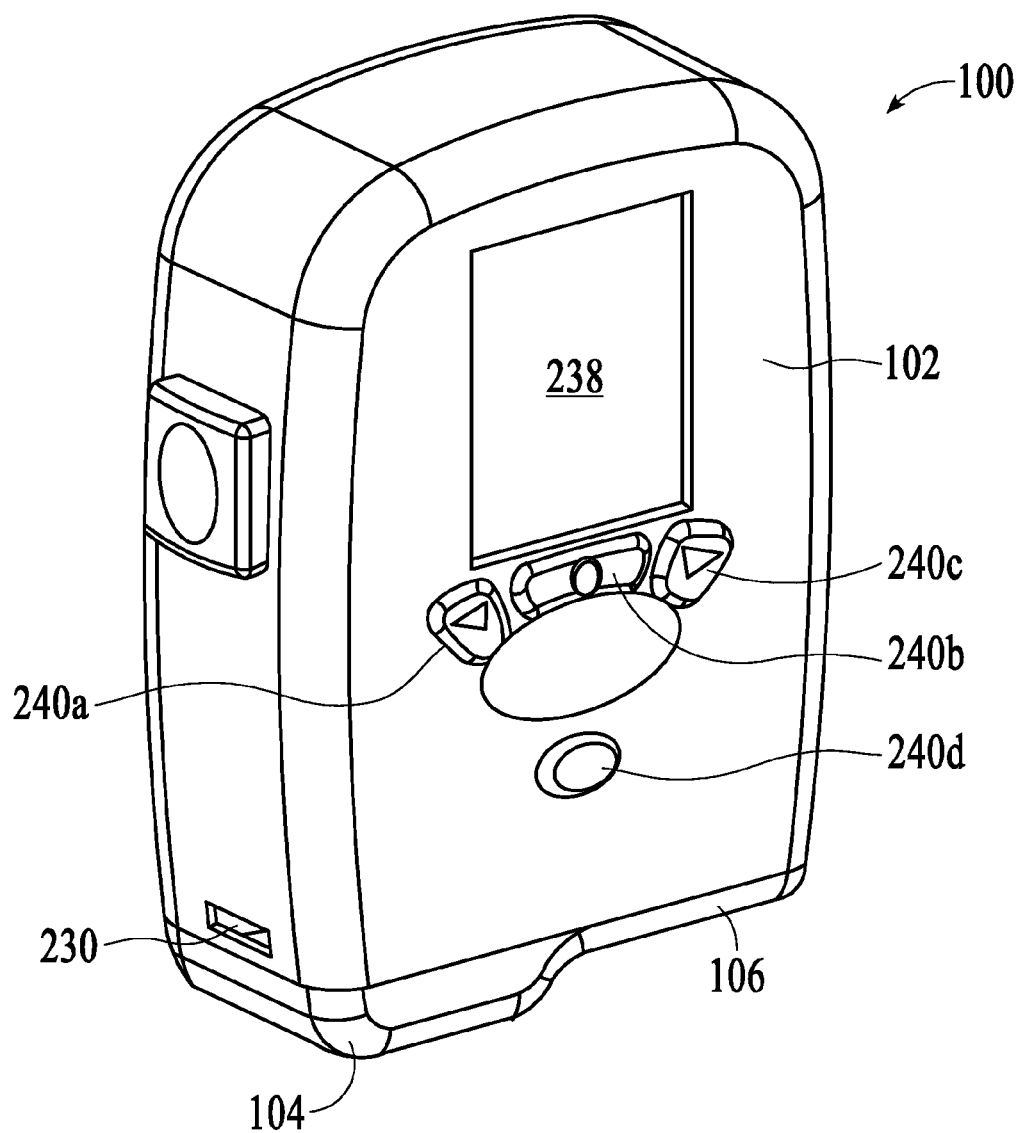
FIG. 2A is a perspective view of the medical diagnostic device with the housing shown attached to an end cap and a tub.
Figure 2C:
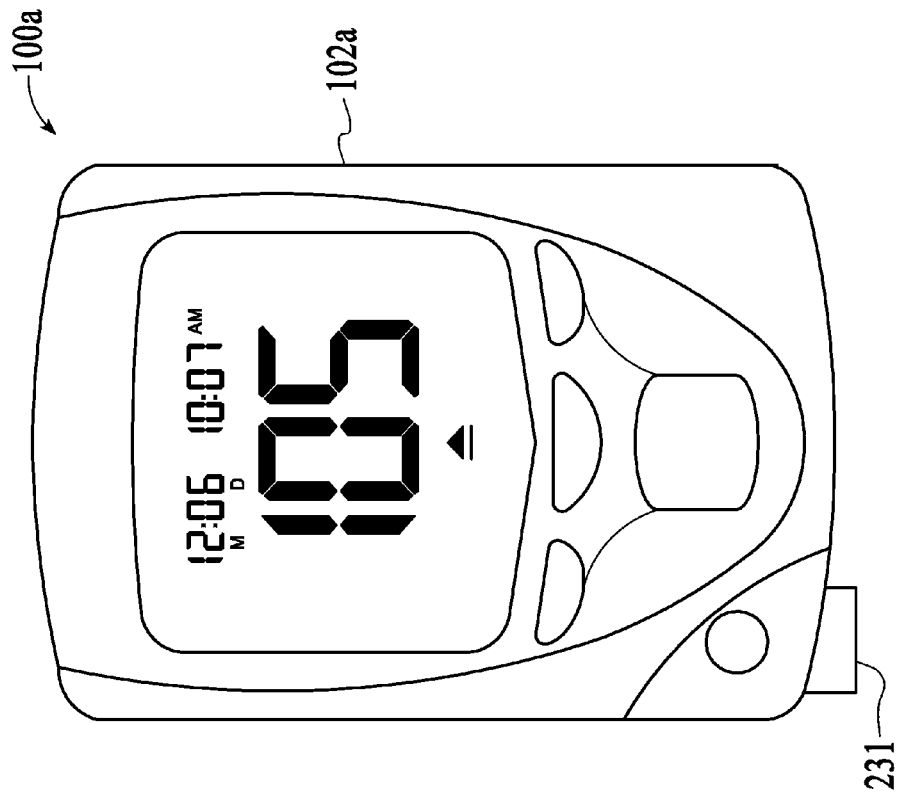
FIG. 2C is a front view illustrating a housing including switches and a display of a user interface of a medical diagnostic apparatus in accordance with an embodiment.
Figure 2B:
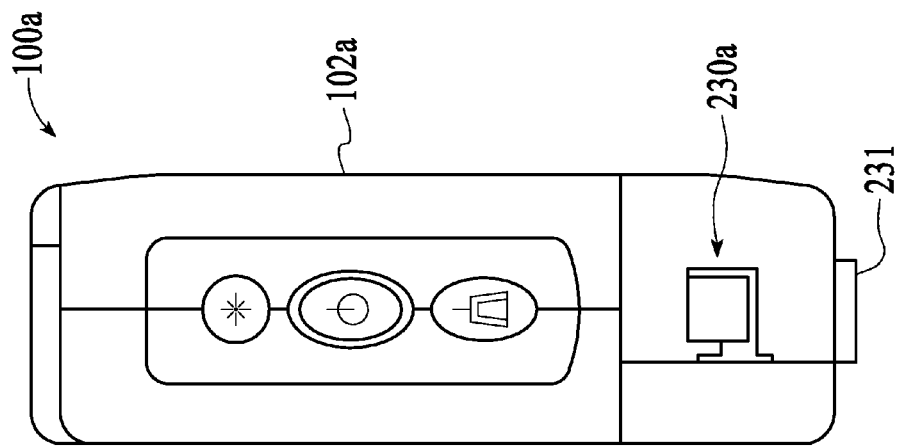
FIG. 2B is a side view illustrating a housing with a port defined therein, and including switches of a user interface, of a medical diagnostic apparatus in accordance with an embodiment.

An ejection port 230 is shown in the illustrations of a medical diagnostic apparatus in accordance with an alternative embodiment FIG. 1 and FIG. 2A, while ejection port 230a is shown in the illustration of the embodiment at FIG. 2B. Although either ejection port 230, 230a may also be used as a lancing and/or testing port, a separate lancing and testing port 231 is provided opening to the bottom of FIGS. 2B and 2C in accordance with an embodiment. In operation (which is described in moiré detail below with reference to FIGS. 7A-7P), the apparatus of an embodiment illustrated at FIGS. 2B-2C lances and tests through port 231, by re-orienting a striplet within the housing 102a after lancing for testing through the same port 231, and then retracting the striplet into the housing after testing, rotating the striplet 90 degrees, re-capping the lancet portion for safety, and ejecting the striplet through ejection port 230a.

As shown in FIGS. 3A-4D, the assembly for storing and dispensing test strips 110, 110a includes a magazine 118, 118a including a plurality of test strips "TS", each test strip comprising a lancet-containing portion and a sensor-containing portion. Test strips that are suitable for use with a medical diagnostic device in accordance with an embodiment are illustrated in FIGS. 26A-33, inclusive, and described in detail in the text accompanying those figures. The magazine 118, 118a has an exterior cover 120, 120a. The purpose of the exterior cover 120, 120a is to maintain the test strips in a substantially moisture-tight, air-tight condition. Materials that are suitable for forming the exterior cover 120, 120a include rubber and other polymeric materials.

Figure 3A:
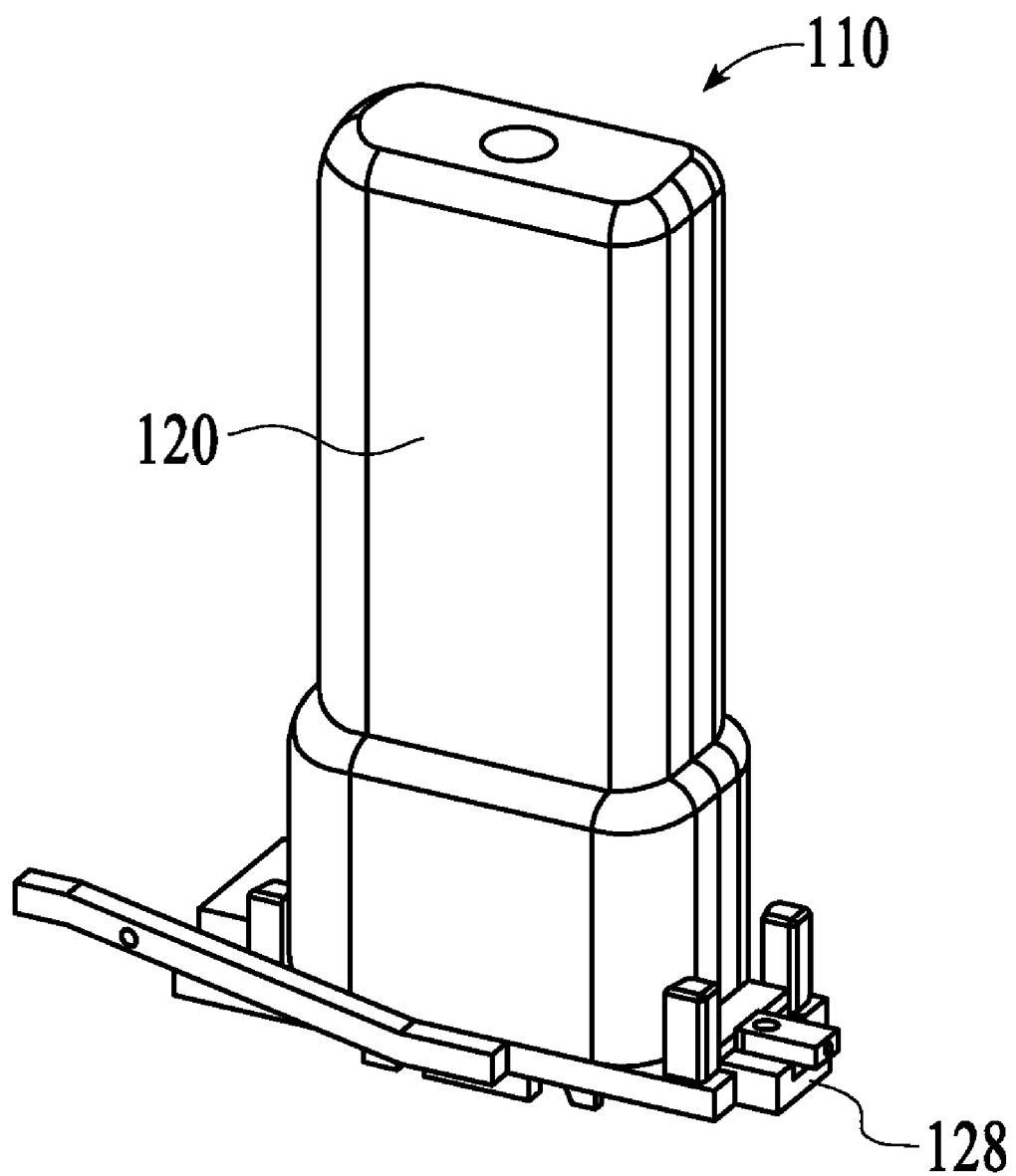
FIG. 3A is a perspective view of one embodiment of an assembly for storing and dispensing the testing striplets suitable for use in the medical diagnostic device in accordance with an embodiment.

Inside the exterior cover 120 of FIGS. 3A and 4A is an interior cover 122, which contains a desiccant. The purpose of the interior cover 122 is to provide a second barrier to maintain the test strips in a substantially moisture-tight, air-tight condition. Materials that are suitable for forming the interior cover 122 include polymeric materials impregnated with a desiccant, e.g., plastic impregnated with desiccant. The structure of the interior cover 122 is substantially congruent with the structure of the exterior cover 120. The desiccant absorbs moisture that evades the exterior cover 120. Inside the interior cover 122 is a platform 124 for containing a biasing element 125, e.g., a constant force spring, for urging test strips toward the location in the magazine 118 from which test strips are fed to the lancing/collecting assembly 112. Also inside the interior cover 122 is an insert 126 for securing the biasing element 125. The platform 124 can be filled with a desiccant, in order to enhance moisture resistance of the test strips stored within the assembly 110.

Figure 3B:
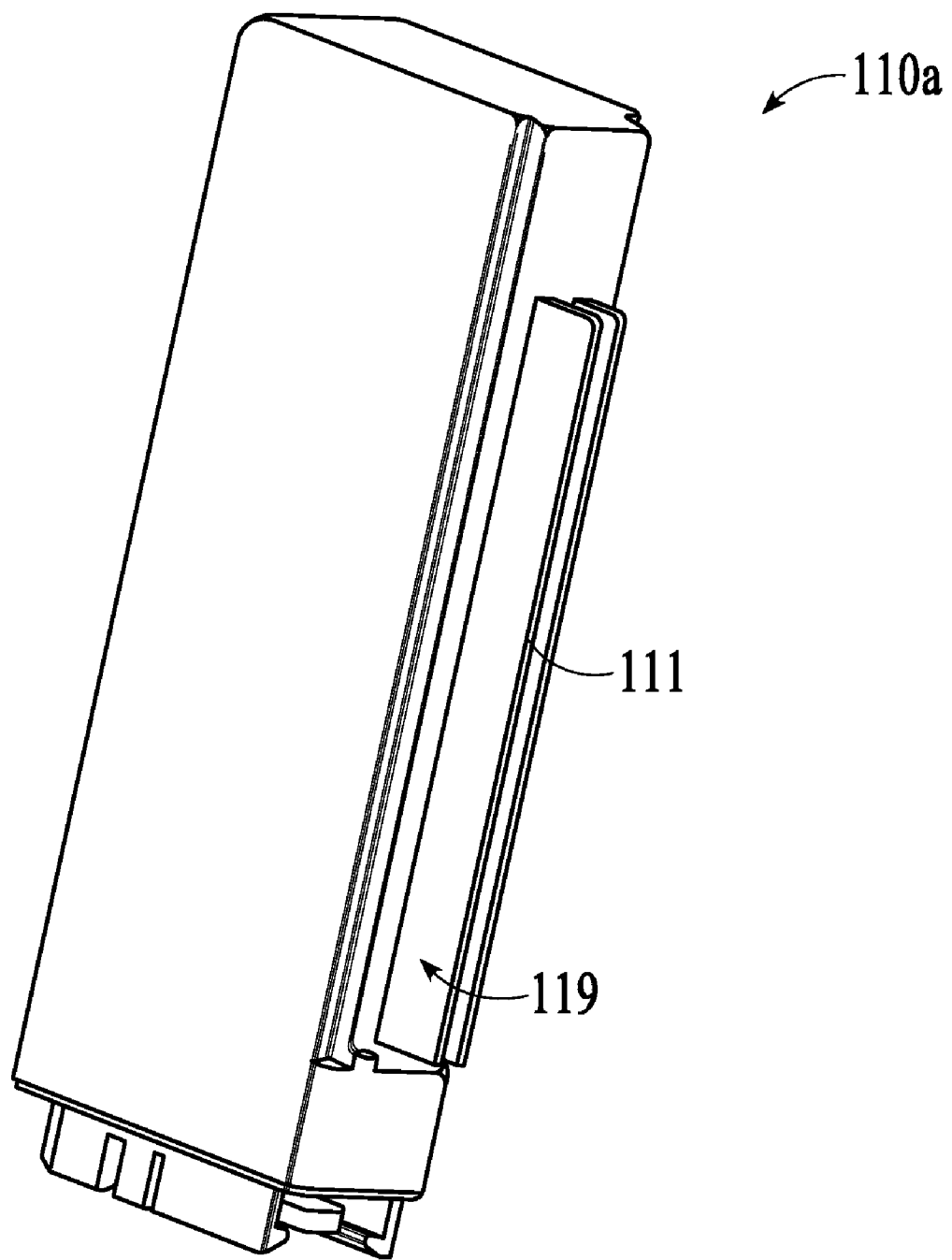
FIG. 3B is a perspective view illustrating another embodiment of a cartridge assembly for storing and dispensing testing striplets.
Figure 6A:
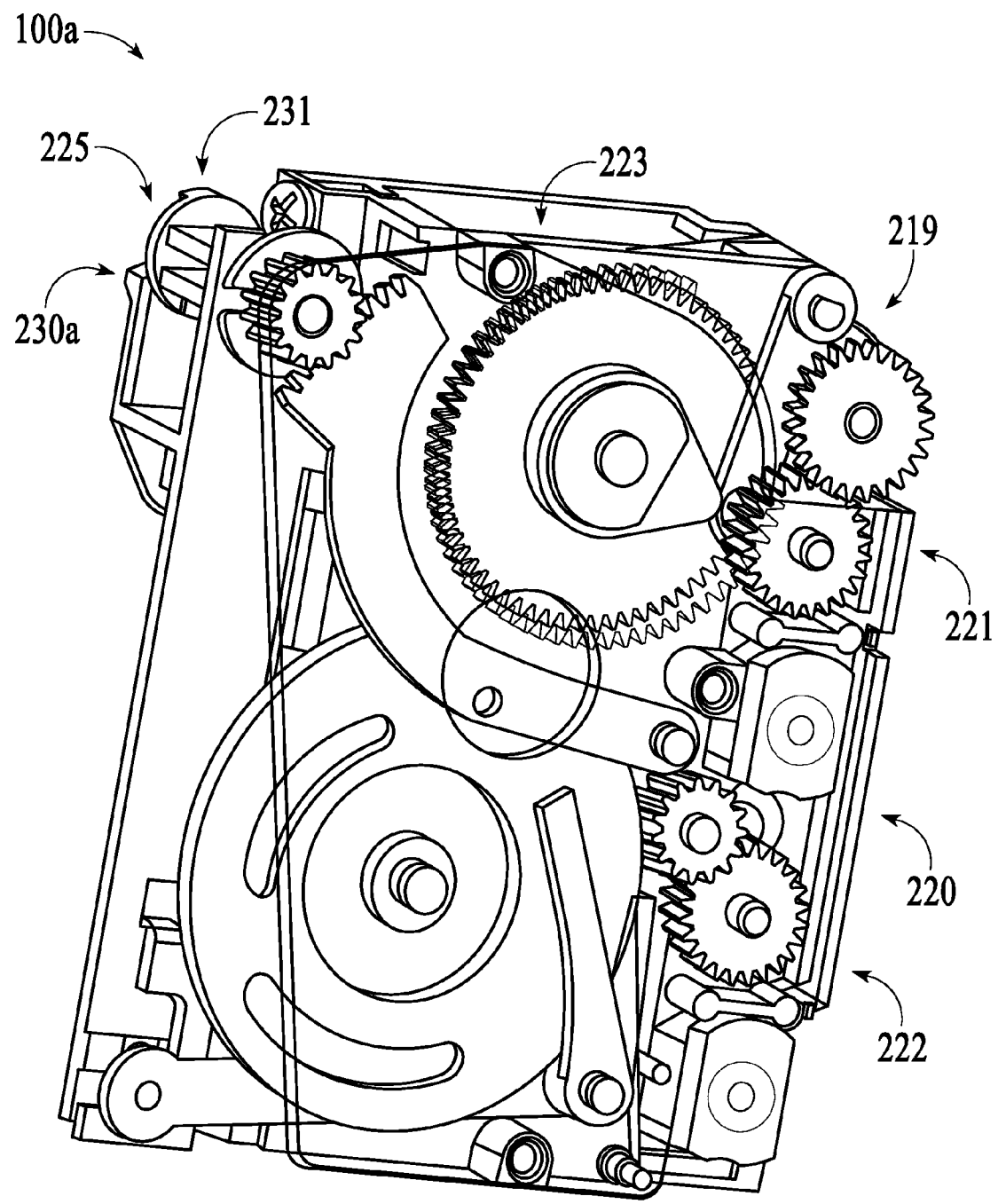
FIG. 6A is a front view of mechanical components of a medical diagnostic apparatus in accordance with an embodiment.

FIG. 3B illustrates a guide rail that moves within a guide track 115 (see FIG. 6C) which is formed as part of the cartridge compartment 123 in the device 100, 100a. The coupling of the guide rail 111 and the guide track 115 permits the cartridge be positioned relative to the device 100, 100a and particularly the mechanical components contained therein which are configured to precisely load, advance and re-orient striplets received from the cartridge. At the end of the guide rail 111 is a stopping point 113. The stopping point meets with a complementary point within the guide track 115 at which point the cartridge 110, 110a cannot be advanced deeper into the cartridge slot 123. The walls of the cartridge slot 123 including the guide track 115 and the stopping point 113 precisely position the cartridge 110, 110a relative to the mechanical components of the medical diagnostic device 100, 100a.

In certain embodiments, the stopping point 113 and complementary point within the track just move apart when the tub T is sealed with the cartridge 110, ensuring a good seal. The cartridge remains substantially stationary relative to the apparatus 100, 100a when the tub T is moved away and unsealed from the cartridge to permit a striplet to be loaded onto a segment of a track leading to turret 225 (see FIGS. 6A and 7B, for example). By "substantially stationary", a small movement actually occurs due to the loss of contact of the cartridge at the stopping point when the tub T is sealed, ensuring a good seal. The small movement of the cartridge occurs when the tub T is moved until the cartridge contacts the stopping point. This small movement may be a far smaller movement than the movement of the tub T to expose a striplet to the guide track segment, which is why the cartridge is deemed to remain "substantially stationary" during the movement of the tub T.

Figure 4B:
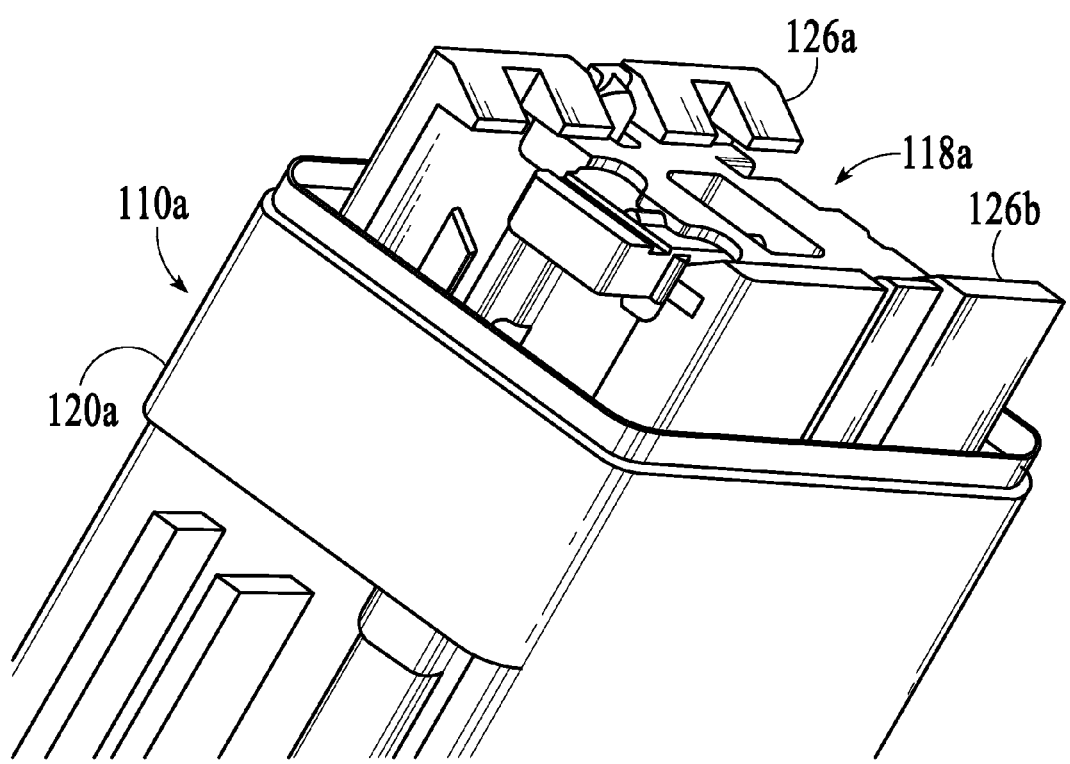
FIG. 4B is a perspective view of a loading end of the cartridge of FIG. 3B.
Figure 4C:
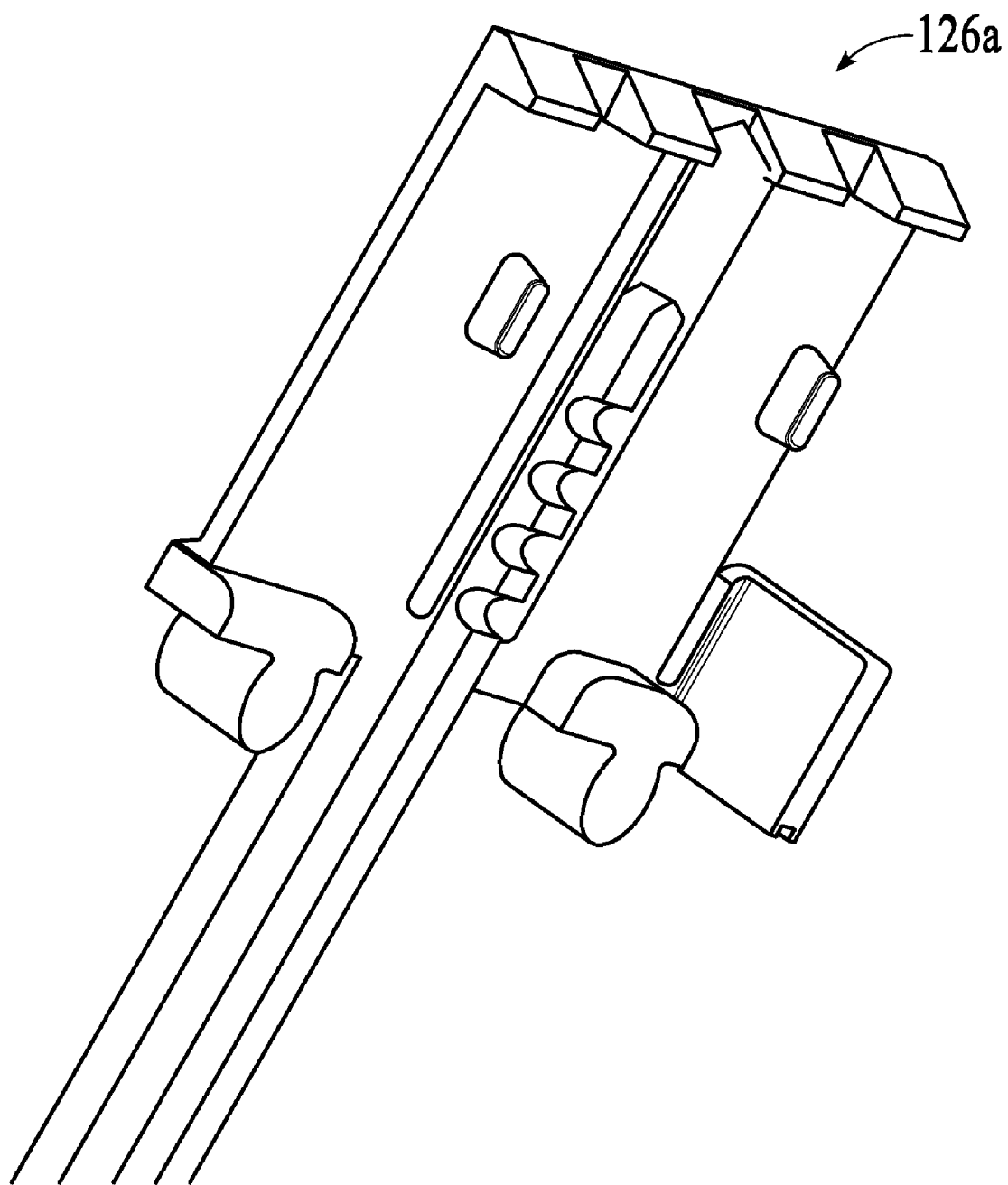
FIG. 4C is a perspective view of an insert or fixed support for structurally supporting and/or desiccating the testing striplets within the cartridge of FIGS. 3B and 4B.
Figure 4D:
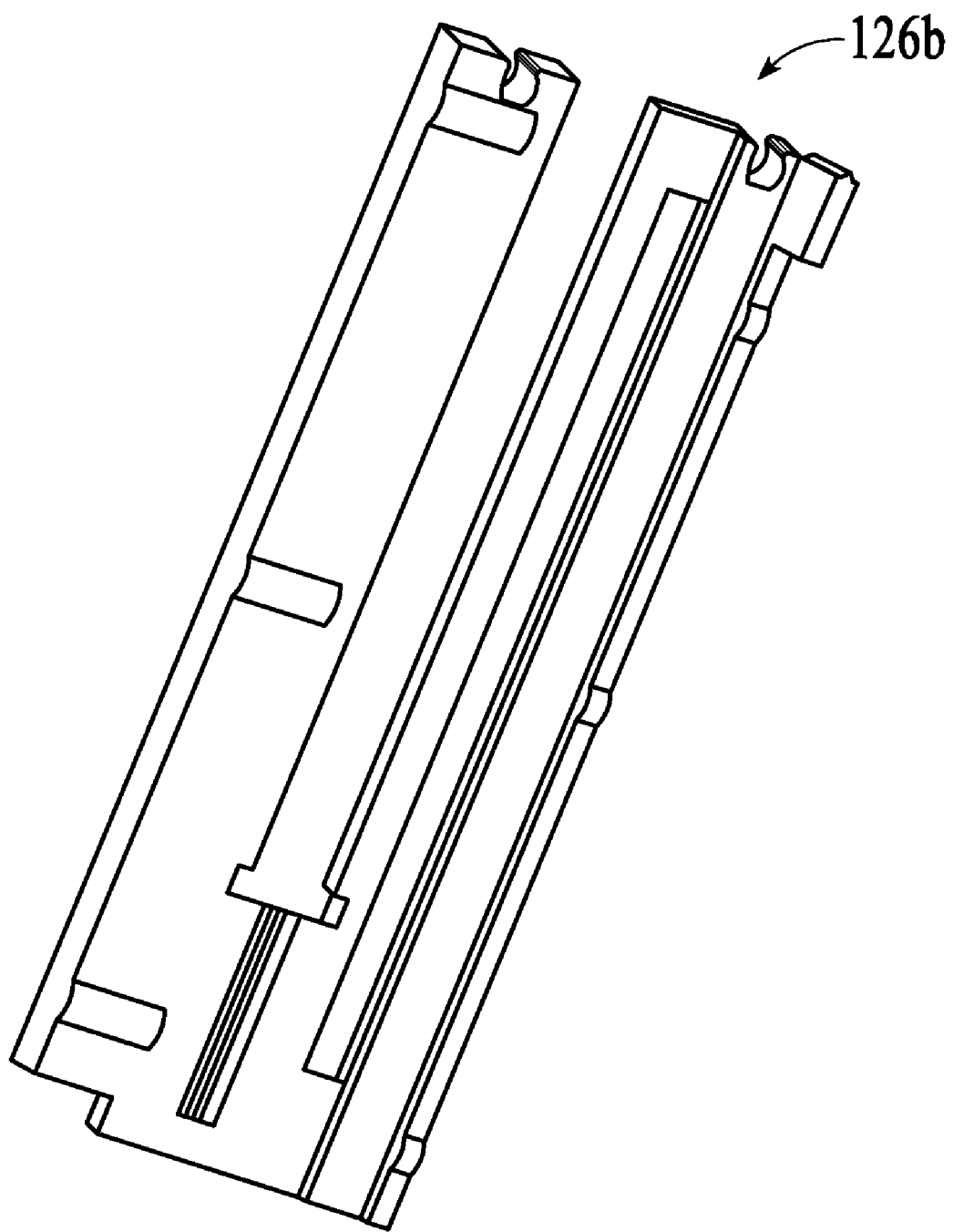
FIG. 4D illustrates a second insert for structurally supporting and/or desiccating the testing striplets within the cartridge of FIGS. 3B and 4B.

The cartridge 110a has inserts or structural supports 126a and 126b in certain embodiments which are illustrated at FIGS. 4C and 4D. The insert 126a of FIG. 4C provides structural support for the testing striplets that are stacked inside the housing cover 120a of cartridge 110a. The other insert 126b of FIG. 4D is made of a desiccating plastic. Insert 126b may provide some structural support or not, and element 126b may provide desiccation without being formed to also provide support, e.g., may be a coating on the wall or a small structure or series of small components interwoven with support 126a, for example. Either or both of the "inserts" 126a and 126b may actually be built-in, e.g., by being molded together with the cartridge body 110, 110a.

Referring back now to FIG. 4A, at least a segment of a test strip track 128 is disposed below the magazine 118, 118a for receiving the test strip from the magazine 118, 118a and for providing a segment of a guide path for a test strip when the test strip is being fed to the lancing/collecting assembly 112. Some of the features shown in FIG. 4A may be present in the embodiment of FIG. 4B even though they are not specifically shown in FIG. 4B. The test strip track 128 also abuts against a seal 130 attached to the bottom end of the magazine 118, 118a. The seal 130 surrounds the bottom end of the magazine 118, 118a and is typically made from a substantially air-impermeable, moisture-impermeable material, such as, for example, rubber or a polymeric material. The combination of the test strip track 128 and the seal 130 provides a substantially moisture-tight, air-tight seal for the magazine 118, 118a. A resilient biasing element 132, e.g., a spring, is positioned exterior to and above the magazine 118, 118a in order to ensure that the magazine 118, 118a can maintain test strips in a substantially moisture-tight, air-tight condition.

Outside of the magazine 118, 118a is a mechanism 134 for feeding test strips to the lancing/collecting assembly 112. This feeding mechanism 134 includes a cam or cam assembly 136 for lifting the magazine 118, 118a, whereby a gap is formed between the seal 130 at the bottom end of the magazine 118, 118a and the test strip track 128. The feeding mechanism 134 further includes a mechanism 138 for advancing a test strip from the magazine 118, 118a to the lancing/collecting assembly 112. The mechanism 138 for advancing a test strip from the assembly for storing test strips and dispensing test strips 110 to the lancing/collecting assembly 112 includes at least one flexible component 140 that translates force applied from a first direction (e.g., vertically) to a force applied in a second direction (e.g., horizontally) to advance a test strip from the magazine 118, 118a to the lancing/collecting assembly 112. Examples of the at least one flexible component 140 include, for example, a flexible strip or flexible strips of a material, e.g., metal or polymeric material, capable of extending around a corner, i.e., an angle of approximately 90°, or a flexible spring or flexible springs, e.g., formed of metal or a polymeric material, capable of extending around a corner, i.e., an angle of approximately 90°. In order to lift the magazine 118, 118a and advance a test strip out of the magazine 118, 118a and into the lancing/collecting assembly 112, the medical diagnostic device 100 is equipped with a slide 142 to which is attached the at least one flexible component 140, either directly, or indirectly by means of an intermediate connector. The slide 142 is positioned to move along a slot 144 in a wall of the housing 102. The user moves the slide 142 in a direction that results in the cam or cam assembly 136 lifting the magazine 118, 118a. After the magazine 118, 118a is lifted to a sufficient extent, whereby the seal 130 separates from the test strip track 128 to temporarily break the substantially moisture-tight, air-tight seal formed by the test strip track 128 and the seal 130, the at least one flexible component 140 pushes a test strip out of the magazine 118, 118a and into the lancing/collecting assembly 112. In an alternative embodiment, the slide 142 can be eliminated and the aforementioned functions can be performed by a motor located within the housing 102.

Figures 5A, 5B:
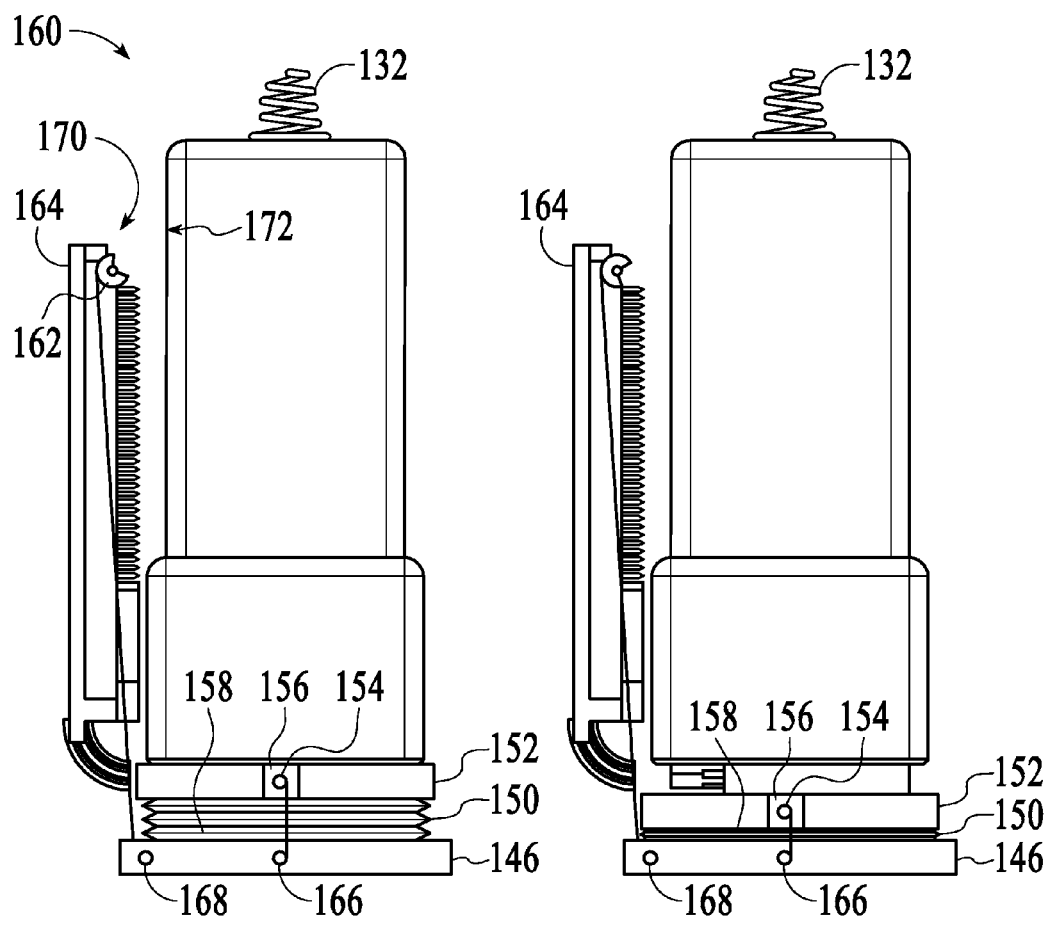
FIGS. 5A and 5B are side views in elevation of one embodiment of an assembly for storing and dispensing the test strips suitable for use in the medical diagnostic device.

FIGS. 5A and 5B illustrate the operation of one alternative for the magazine 118, 118a in which test strips are stored and from which test strips are fed to the lancing/collecting assembly 112. In this embodiment the magazine 118, 118a is mounted on a base 146. The magazine 118, 118a remains immobile throughout the step of feeding a test strip to the lancing/collecting assembly 112. The magazine 118, 118a is not lifted or lowered by a cam or cam assembly to unseal the magazine 118, 118a. An opening in the magazine 118, 118a from which the test strips emerge when fed into the lancing/collecting assembly 112 is maintained in a sealed condition by a bellows 150. The bellows 150 is attached to both the base 146 and a movable element 152, which surrounds the bottom of the magazine 118, 118a. The movable element 152 is of such a shape and dimensions that the movable element 152 fits around the bottom of the magazine 118, 118a to bring about a substantially moisture-tight and air-tight seal of the magazine 118, 118a. The movable element 152 is biased to a position to maintain the substantially moisture-tight, air-tight seal of the magazine 118, 118a. Attached to the movable element 152 is a first post 154, to which is attached one end 156 of a cord 158. The cord 158 is typically made of a metallic material. The other end 160 of the cord 158 is attached to a second post 162, which is attached to a slide 164, which is used for advancing a test strip from the magazine 118, 118a to the lancing/collecting assembly 112. Guide wheels 166, 168 are attached to the base 146 for maintaining the cord 158 in a taut condition. When the slide 164 is in its starting position, the bellows 150 is fully extended, thereby maintaining the magazine 118, 118a in a sealed condition. Furthermore, a pin 170 projecting from the slide 164 orients a recess 172 in the periphery of the second post 162 so as to enable the bellows 150 to be maintained in the fully extended position. When the slide 164 is moved in a direction to advance a test strip from the magazine 118 to the lancing/collecting assembly 112, the pin 170 projecting from the slide 164 orients of the recess 172 in the periphery of the second post 162 so as to cause the movable element 152 to descend and compress the bellows 150, thereby enabling a gap to be formed between the movable element 152 and the bottom of the magazine 118, thereby further enabling a mechanism for advancing a test strip from the assembly for storing test strips and dispensing test strips 110 to the lancing/collecting assembly 112 to advance a test strip through this gap and subsequently into the lancing/collecting assembly 112. Movement of the slide 164 to its starting position raises the movable element 152 to a position whereby the bellows 150 is fully extended so as to maintain the magazine 118 in a substantially moisture-tight, air-tight condition.

Figure 5D:
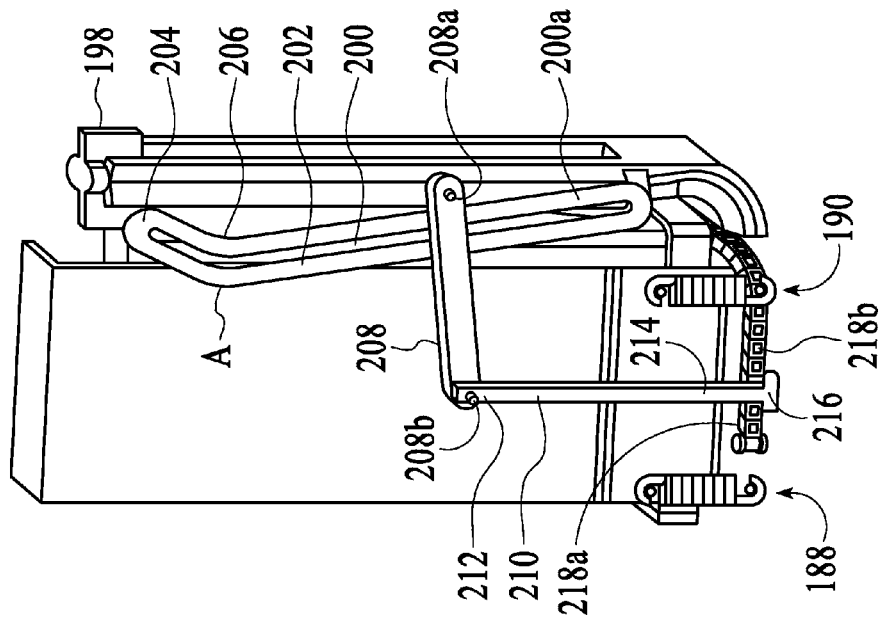
FIG. 5D is a side view in elevation of the other side of the embodiment of the assembly for storing and dispensing the test strips shown in FIG. 7.
Figure 5C:
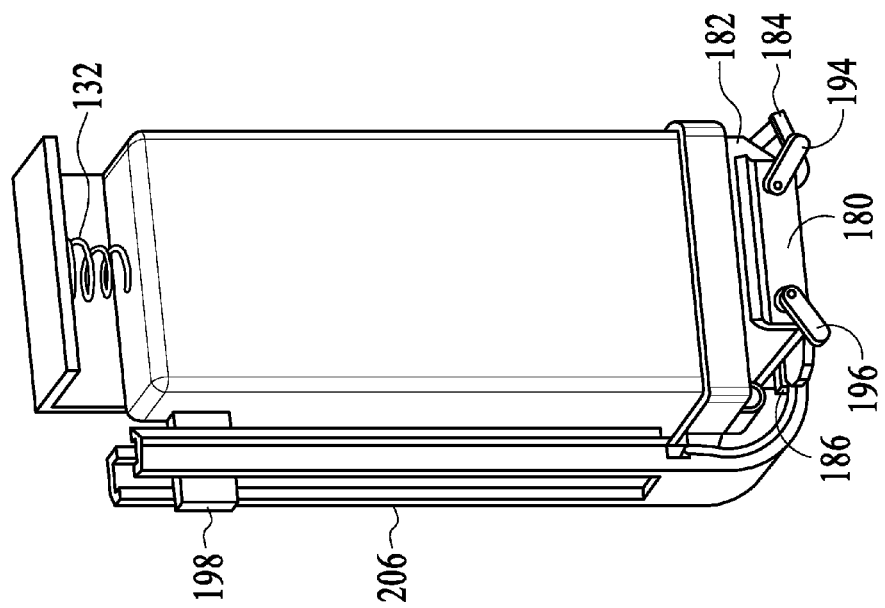
FIG. 5C is a side view in elevation of one side of one embodiment of an assembly for storing and dispensing test strips suitable for use in the medical diagnostic device.

FIGS. 5C and 5D illustrate the operation of another alternative for the magazine 118, 118a in which test strips are stored and from which test strips are fed to the lancing/collecting assembly 112. In this embodiment the magazine 118, 118a is mounted on a base 180. The magazine 118, 118a remains immobile throughout the step of feeding a test strip to the lancing/collecting assembly 112. The magazine 118, 118a is not lifted or lowered by a cam or cam assembly to unseal the magazine 118, 118a. An opening 182 in the magazine 118, 118a from which a test strip emerges when fed into the lancing/collecting assembly 112 is maintained in a sealed condition, i.e., a substantially moisture-tight and air-tight condition, by a set of doors 184 and 186. The door 184 is maintained in a closed position by a resilient biasing element 188, e.g., a spring, which resiliently biases the door 184 to the closed position. The door 186 is maintained in a closed position by a resilient biasing element 190, e.g., a spring, which resiliently biases the door 186 to the closed position. The resilient biasing elements 188 and 190 are extended to cause the doors 184 and 186, respectively, to open, whereby a mechanism for advancing a test strip from the assembly for storing test strips and dispensing test strips 110 to the lancing/collecting assembly 112 can advance a test strip from the magazine 118, 118a through the opening 182 to the lancing/collecting assembly 112. The doors 184 and 186 are attached to the base 180 on which the magazine 118, 118a is mounted by hinges 194, 194a and 196, 196a, which enable the doors 184 and 186 to swing from a closed position to an open position, and vice-versa. The resilient biasing elements 188 and 190 are extended by a three-component assembly linked to a slide 198, which is used to open the doors 184 and 186 to enable the advancement of a test strip from the magazine 118, 118a to the lancing/collecting assembly 112. One component of the three-component assembly is a bi-directional rod 200 having a bi-directional slot 202 formed therein. The bi-directional slot 202 receives the pin 170 attached to the slide 198. The pin 170 moves in a slot 206, which restricts the movement of the pin 204 to a single direction. Attached to the bi-directional rod 200 is the second component of the three-component assembly, a rod 208 that extends in a direction substantially perpendicular to the lower end 200a of the bi-directional rod 200. The first end 208a of the rod 208 is securely attached to the bi-directional rod 200, and can only move when the bi-directional rod 200 moves. The third component of the three-component assembly is a rod 210 having a first end 212 pivotally connected to the second end 208b of the rod 208 and a second end 214 having a T-shaped projection 216 thereon that exerts a negligible force upon the resilient biasing elements 188 and 190 when the slide 198 is in its uppermost, or starting, position. In order to cause the doors 184 and 186 to open so that a mechanism for advancing a test strip from the assembly for storing test strips and dispensing test strips 110 to the lancing/collecting assembly 112 can advance a test strip from the magazine 118, 118a to the lancing/collecting assembly 112, the slide 198 is pushed in a direction to cause the pin 170 to move until it reaches a position "A", at which point the bi-directional feature of the bi-directional rod 200 causes the second end 208b of the rod 208 to move upwardly, which, in turn, causes the rod 210 to rise slightly, thereby causing the T-shaped projection 216 to raise an extension 218a of the door 184 and an extension 218b of the door 186, which extends the resilient biasing elements 188 and 190, respectively, thereby causing the doors 184 and 186 to open. When the doors 184 and 186 are open, the mechanism for advancing a test strip from the assembly for storing test strips and dispensing test strips 110 to the lancing/collecting assembly 112 causes a test strip to be fed from the magazine 118, 118a to the lancing/collecting assembly 112. When the slide 198 returns to its starting position, the resilient biasing elements 188 and 190 retract, thereby causing the doors 184 and 186 to close, and, consequently restoring the substantially air-tight, moisture-tight seal between the doors 184 and 186 and the magazine 118, 118a.

For the latter two embodiments, the mechanism for advancing a test strip from the assembly for storing test strips and dispensing test strips 110 to the lancing/collecting assembly 112 can be similar to that shown and described for the first embodiment. In the three embodiments described herein, the mechanism for advancing a test strip from the assembly for storing test strips and dispensing test strips 110 to the lancing/collecting assembly 112 can be separate from the mechanism for unsealing of the magazine 118, 118a or the mechanism for advancing a test strip from the assembly for storing test strips and dispensing test strips 110 to the lancing/collecting assembly 112 can be integrated with the mechanism for unsealing of the magazine 118, 118a.

Figure 23:
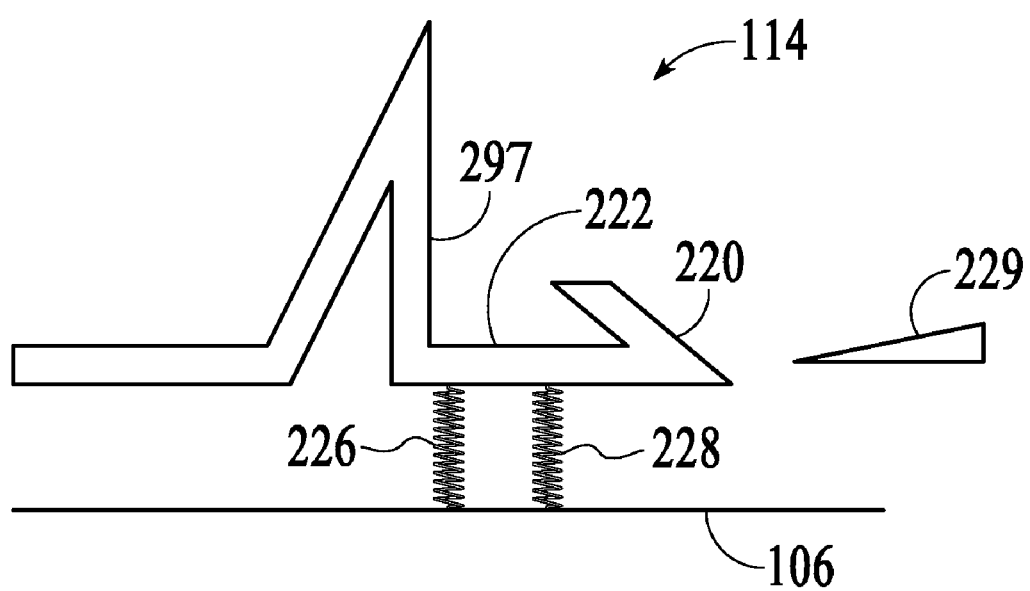
FIG. 23 is a schematic view of a mechanism suitable for use in a medical diagnostic apparatus of an alternative embodiment for removing a protective cover from a lancet and re-attaching the protective cover to the lancet.

Because the lancet of the lancet-containing portion of the test strip is furnished with a protective cover, the protective cover must be removed or displaced from the tip of the lancet before the lancet can be used to form an opening in the skin of the patient. Accordingly, the assembly 114 for removing a protective cover from the tip of a lancet and re-attaching the protective cover to the tip of a used lancet is located in a position whereby the assembly 114 can remove the protective cover from the tip of the lancet of the lancet-containing portion of the test strip prior to the lancing step and re-attach the protective cover to the tip of the lancet of the lancet-containing portion of the test strip prior to disposal of the test strip after the test strip has been used. As shown schematically in FIG. 23, the assembly 114 includes a strip of flexible metal comprising a cover-snagging portion 220, a cover-storing portion 222, and a cover-stopping portion 297. The assembly 114 can be positioned between the magazine 118, 118a and the lancing/collecting assembly 112. The assembly 114 is mounted to the tub 106 by one or more resilient biasing elements 226 and 228, e.g., springs, which enable upward and downward movement of the assembly 114. As a test strip is being advanced from the magazine 118, 118a, the test strip slides over the cover-stopping portion 297 and the cover-storing portion 222 until the protective cover is snagged by the cover-snagging portion 220. As the test strip continues to advance to the lancing/collecting assembly, the lancet of the lancet-containing portion of the test strip is separated from the protective cover and the test strip enters the lancing/collecting assembly 112. The protective cover is retained in the cover-storing portion 220. At the completion of the testing procedure, the protective cover is re-attached to the tip of the lancet by moving the test strip toward the assembly 114 or by moving the assembly 114 toward the test strip, whereby the tip of the used lancet re-enters the protective cover. The protective cover is made from a material that can receive the sharp tip of a lancet. The cover-stopping portion 297 stops the protective cover from sliding during re-attachment of the protective cover to the tip of the lancet to facilitate the step of re-attachment. The resilient biasing elements 226 and 228 enable the assembly 114 to move upwardly and downwardly, as required, to remove the protective cover from the tip of the lancet or to re-attach the protective cover to the tip of the lancet. The cover-snagging portion 220 is moved downwardly by a compressing element 229 after the protective cover is re-attached to the tip of the lancet to allow the re-covered test strip to be ejected from the medical diagnostic device 100. A pushing device can be used to push the re-covered test strip to force the used, re-covered test strip out of an ejection port 230 in the housing 102.

Referring again to FIGS. 1 and 2A-2C, a printed circuit board (PCB) assembly 232 for controlling the electromechanical components and the electronic components of the medical diagnostic device 100, 100a is positioned in the housing 102, 102a. At least one battery 234 is included in the housing 102, 102a to provide a source of power for at least one motor 236 that will drive the lancing/collecting assembly 112 and, optionally, to drive one or more additional functional components of the medical diagnostic device 100, including, but not limited to, the assembly 110, 110a for advancing test strips from the magazine 118, 118a to the lancing/collecting assembly 112, the system for arming the lancet, the system for triggering the lancet, and to provide power for the analyzer 116 for determining the parameter of the biological liquid to be measured, storing data collected, activating the display, and other features of the analyzer 116. More than one motor can be employed for carrying out the various mechanical functions described herein. The medical diagnostic device 100, 100a has a display 238, typically a liquid crystal display, for showing the results of the determinations of analytes. The medical diagnostic device 100, 100a typically includes one or more flexible circuits for connecting the PCB assembly 232 to the analyzer 116 and connecting the PCB assembly 232 to the motor or motors. The medical diagnostic device 100 can also include flexible circuits to connect the PCB assembly 232 to one or more sensors to determine the status of the medical diagnostic device 100, 100a. The medical diagnostic device 100, 100a also has various activation buttons 240a, 240b, 240c, and 240d for actuation of various functions of the medical diagnostic device 100, 100a. The medical diagnostic device 100, 100a can also have an alphanumeric keypad for manual input of various parameters related to determination of analytes.

The medical diagnostic device 100, 100a has a depth adjustment control 242. A particularly useful depth adjustment control employs a knob that is rotated to control movement of the end cap 104 or a portion thereof so that the depth of penetration of the lancet of the lancet-containing portion of the test strip can be specified. In another embodiment, a series of caps of different sizes are affixed to the housing at the lancing and testing port to accommodate the different lancing depths that are preferred by different patients or users.

Figure 6B:
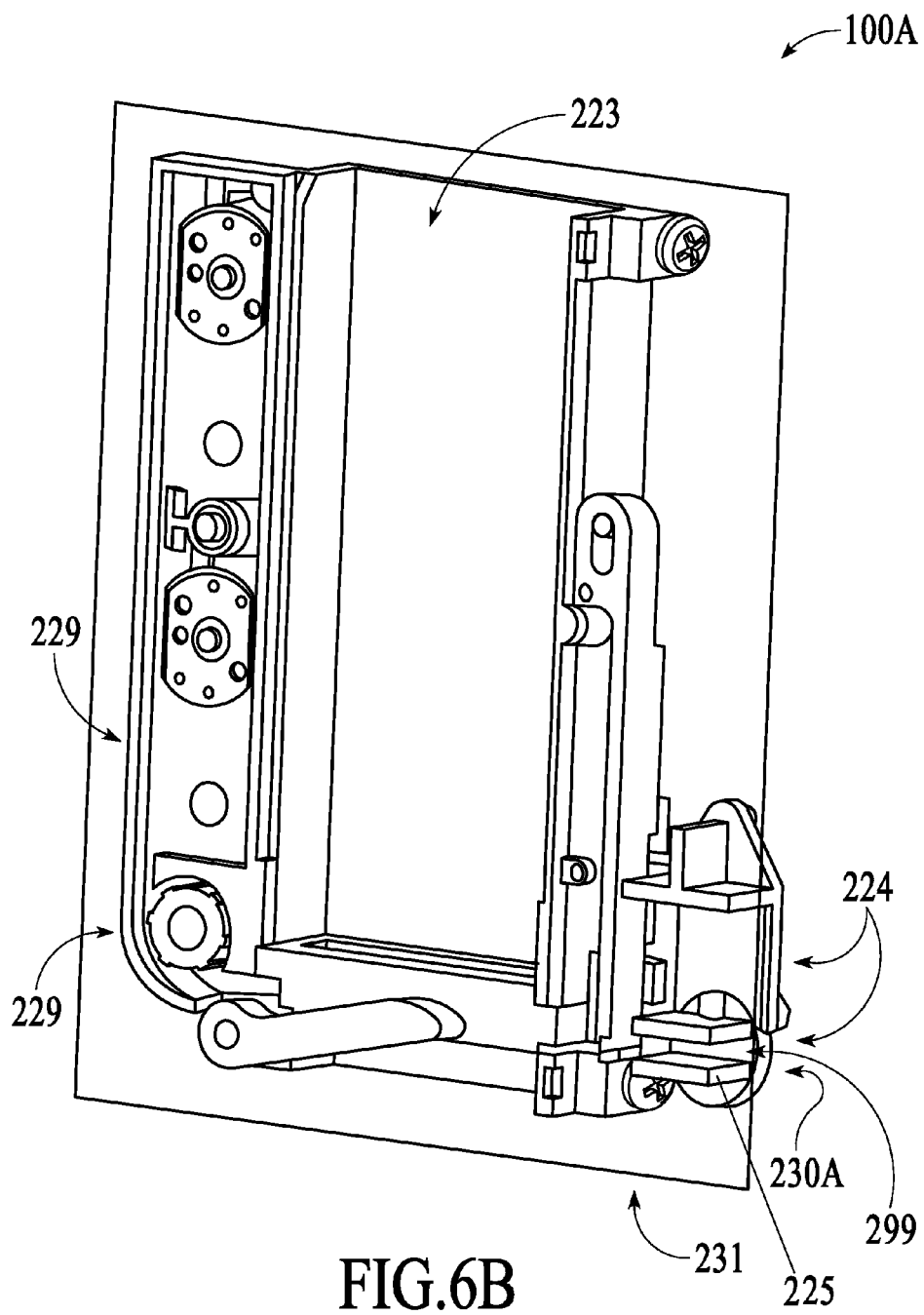
FIG. 6B is a back view of mechanical components of a medical diagnostic apparatus in accordance with an embodiment.
Figure 6C:
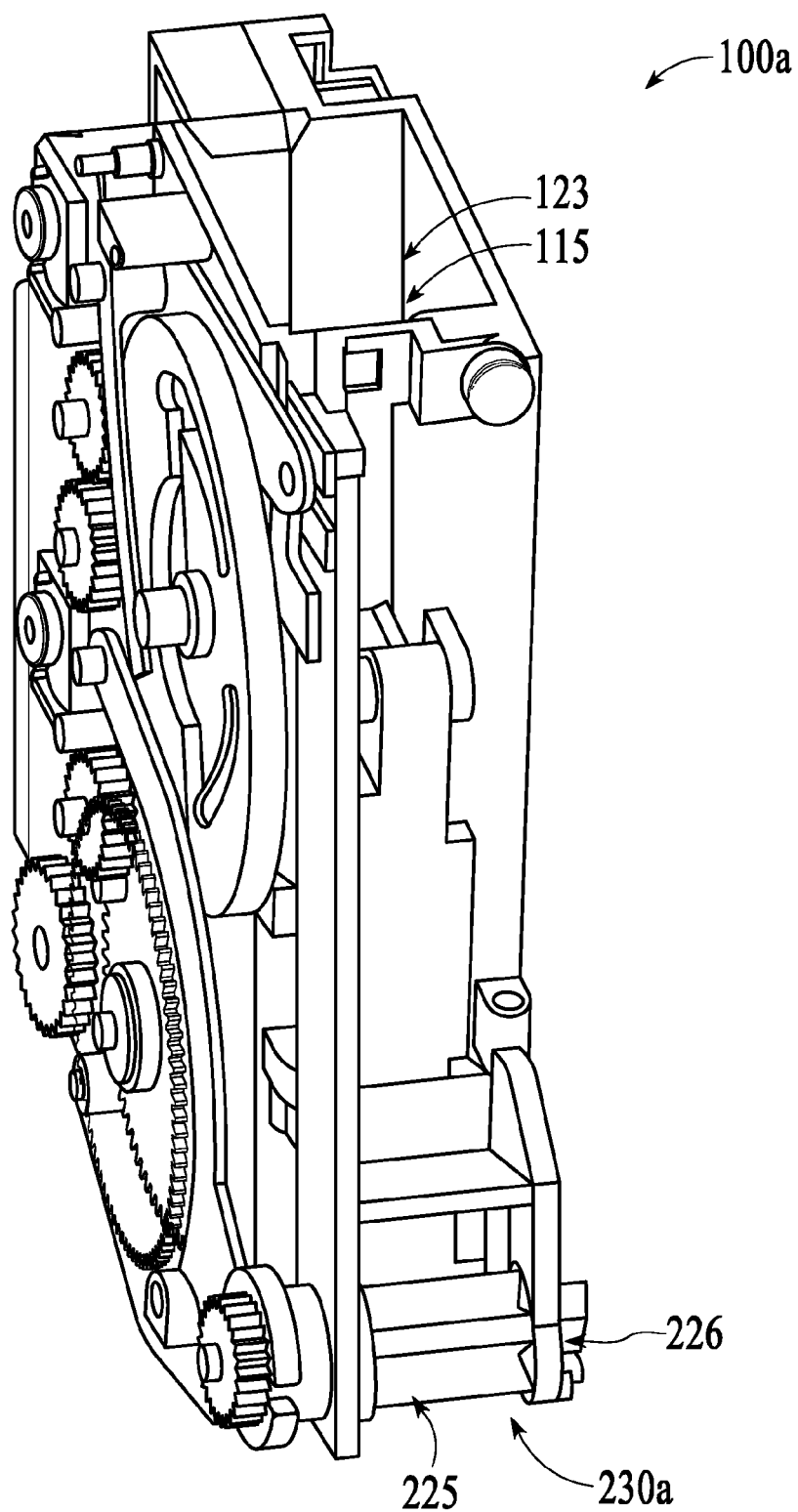
FIG. 6C is a side view of mechanical components of a medical diagnostic apparatus in accordance with an embodiment.
Figure 6D:
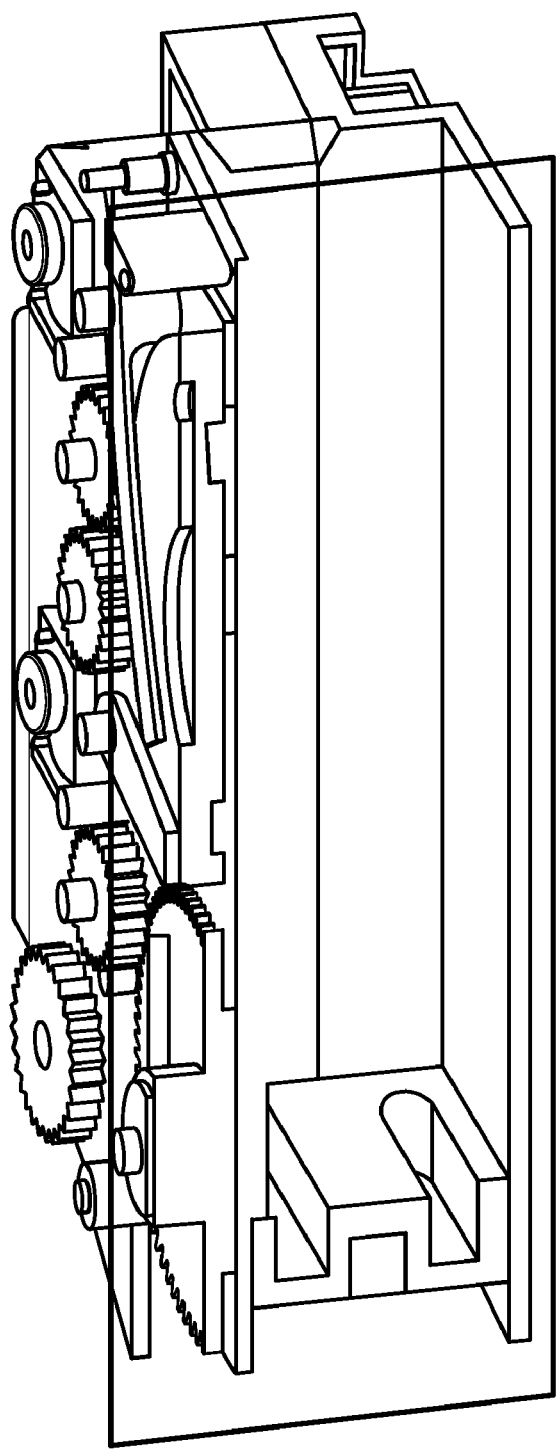
FIG. 6D is an opposite side view to FIG. 6C of mechanical components of a medical diagnostic apparatus in accordance with an embodiment.
Figure 6E:
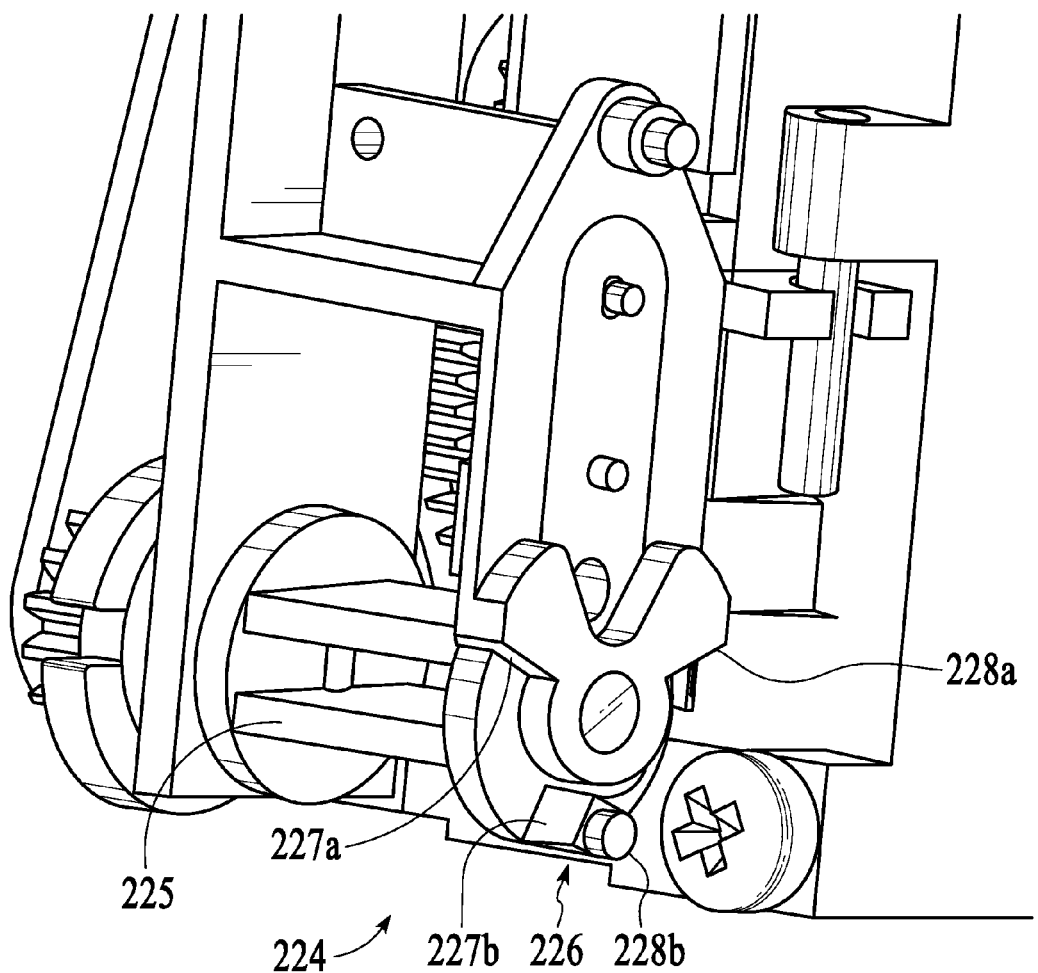
FIG. 6E is a perspective view of a rotatable slot for re-orienting a testing striplet within a medical diagnostic apparatus in accordance with an embodiment.

FIGS. 6A-6D are front, back, side and opposite side views, respectively, of mechanical components of a medical diagnostic apparatus 100, 100a in accordance with an embodiment, while FIG. 6E is a perspective view of a rotatable turret 225 including a striplet slot 299 for re-orienting a testing striplet within a medical diagnostic apparatus 100, 100a in accordance with an embodiment.

The apparatus shown functions substantially mechanically according to first and second mechanical subsets 219 and 220, respectively, which includes first and second sets of gears 221 and 222, in addition to various cams and levers. There is a cartridge slot defined down the center of the long dimension of the apparatus 100a. A re-orientation carriage 224 is shown including turret 225 that rotates according to the movement of a cam 226 that oscillates between points, for example around an unstable equilibrium or other mechanism for urging the rotation of the turret 225 for re-orienting the striplet between lancing and testing via port 231 and ejecting via port 230a. In an embodiment, the turret 225 is rotated 90 degrees, from an original position that the turret 225 is in when the striplet 1000a is loaded, prior to translation through the port 231 of FIG. 6B for lancing, 180 degrees prior to translation through the port 231 for testing, and 90 degrees prior to ejection through port 230a of FIG. 6B. Referring to FIG. 6E, the striplet is oriented in a first direction when surfaces 227a and 227b meet for lancing, and the striplet is oriented in a second direction for testing, rotated approximately 180 degrees or another angle equal to the angular displacement of the lancet and reagent area of the striplet, or flipped relative to the first direction, when surfaces 228a and 228b meet. When the striplet is in the first direction, it is armed for lancing such that upon advancement through port 231, a lancing site can be pierced. When the striplet is re-oriented as a result of the functioning of cam 226, the striplet is ready to be advanced through the port 231 in the new orientation, so that a test sensor this time extends to touch the bodily fluid exposed at the lancing site due to the lancing. In the position shown in FIG. 6E, a fresh striplet may be loaded into the turret 225 from the cartridge, and a used striplet may be discarded through ejection port 230a.

Figure 6F:
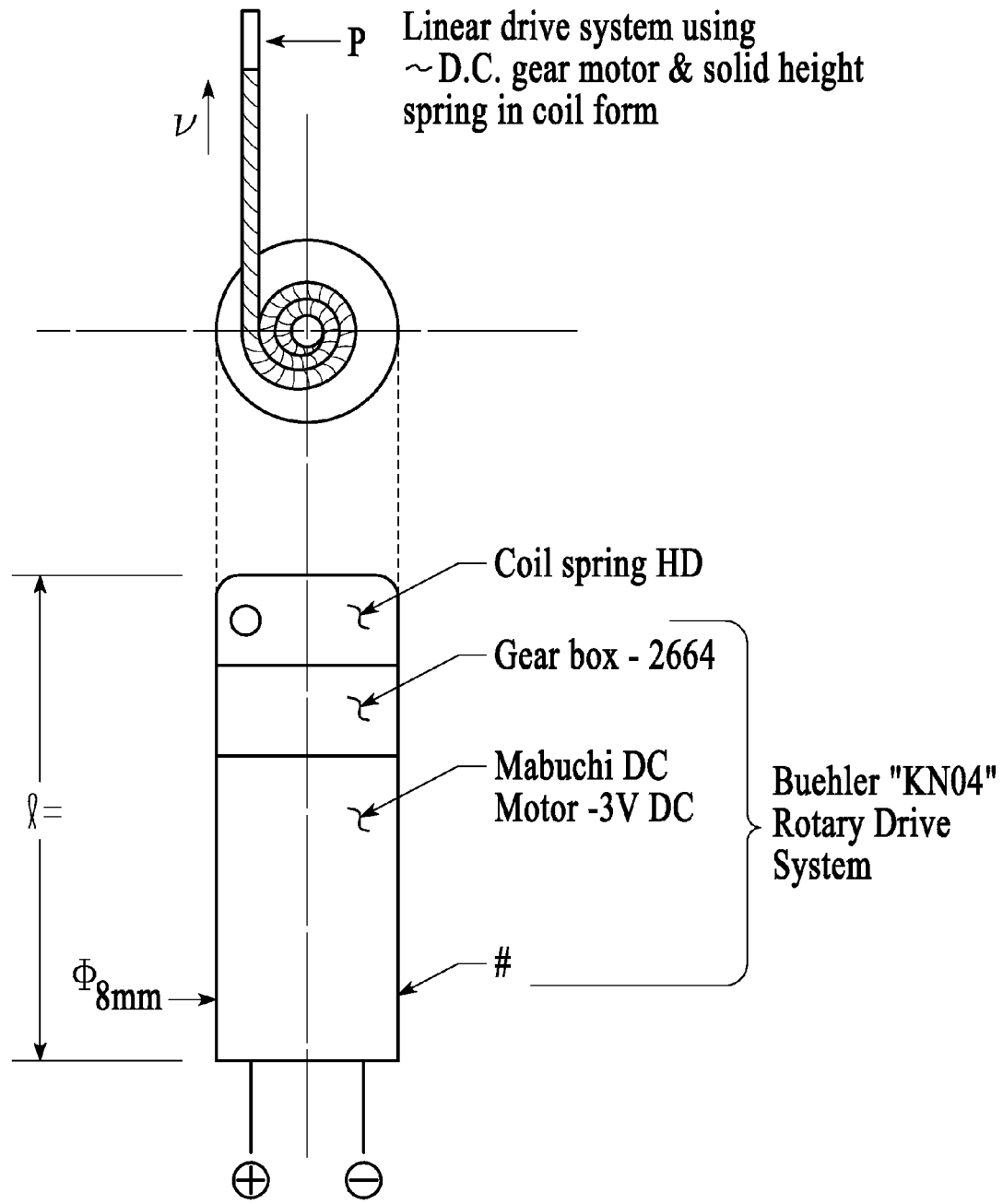
FIG. 6F is a exemplary embodiment illustrating how a pusher P may be advanced and retreated along a guide track for advancing the striplet to the turret and arming the lancet, respectively.
Figure 7A:
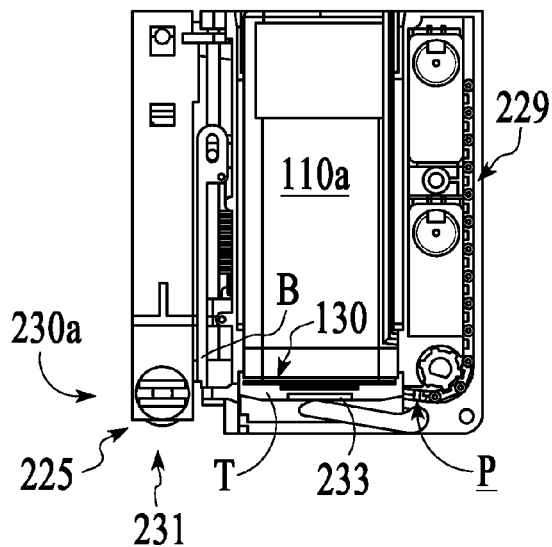
FIGS. 7A-7P illustrate an operational sequence of a medical diagnostic apparatus in accordance with an embodiment.
Figure 7B:
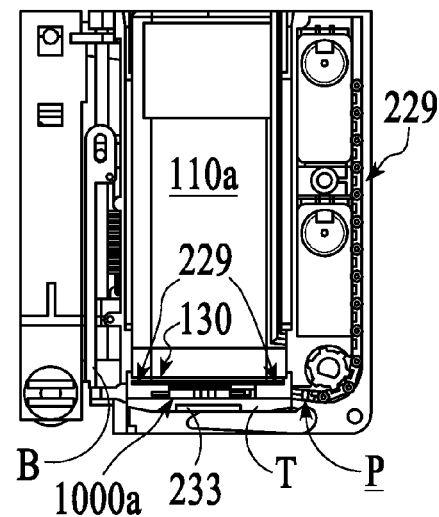
Figure 7C:
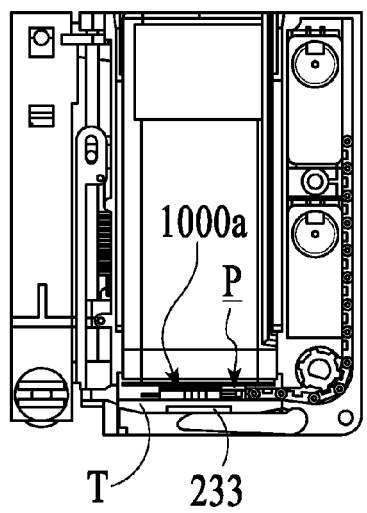
Figure 7D:
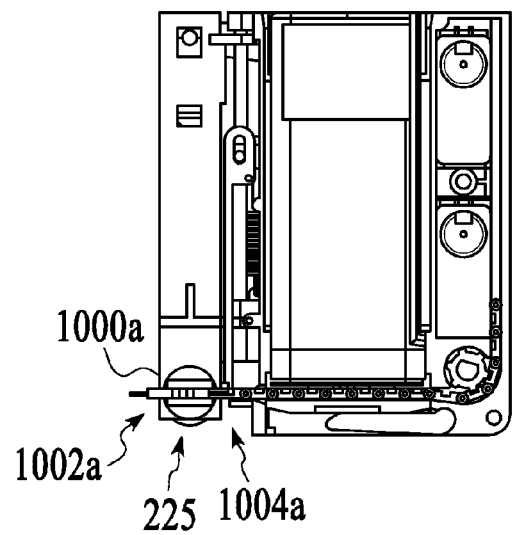
Figure 7E:
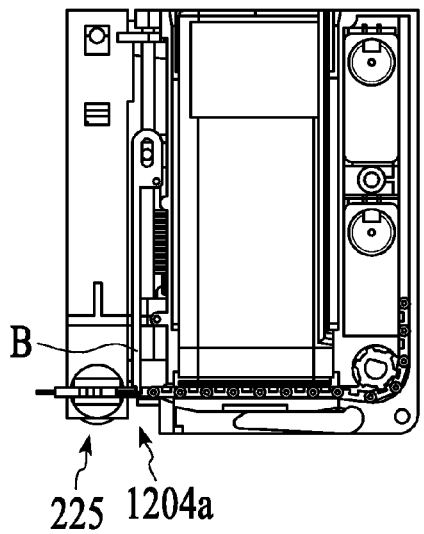
Figure 7F:
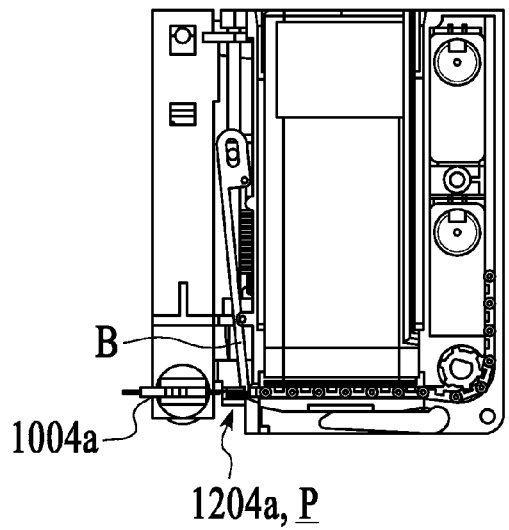
Figure 7G:
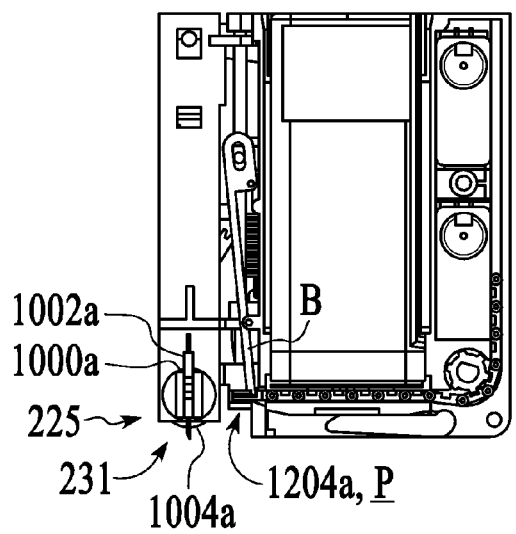
Figure 7H:
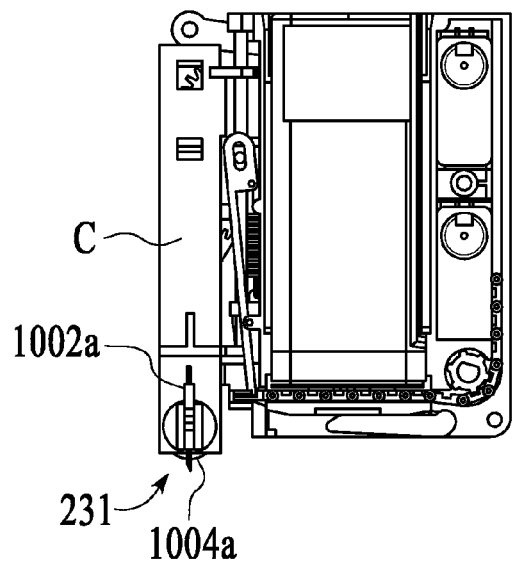
Figure 7I:
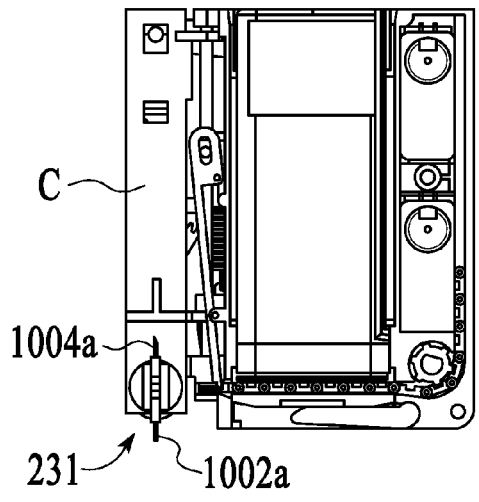
Figure 7J:
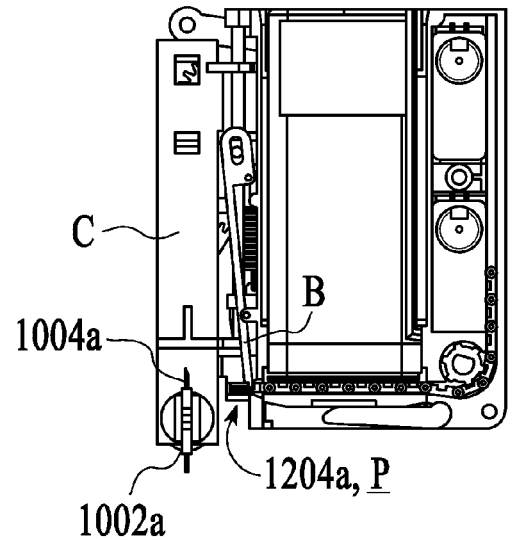
Figure 7K:
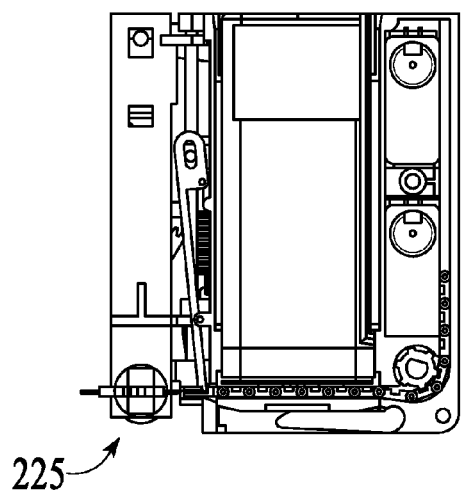
Figure 7L:
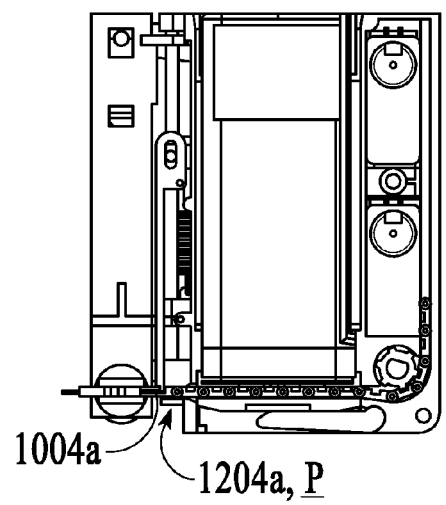
Figure 7M:
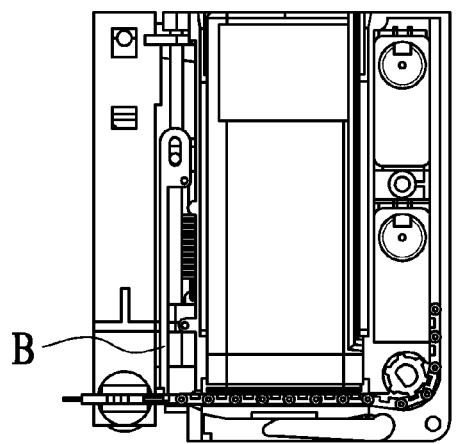
Figure 7N:
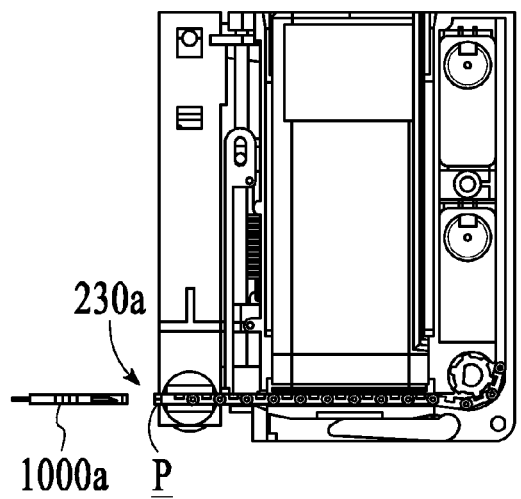
Figure 7O:
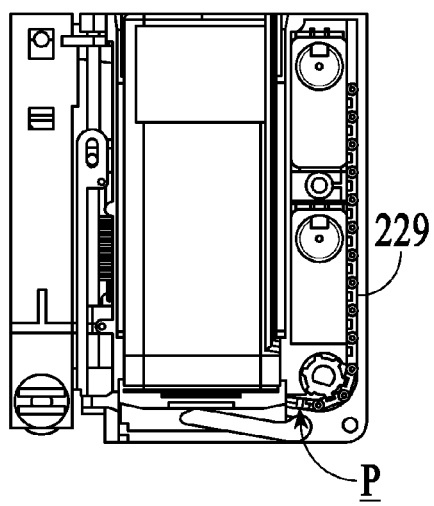
Figure 7P:
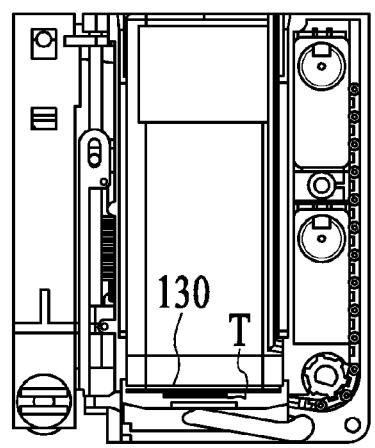
Figure 8:
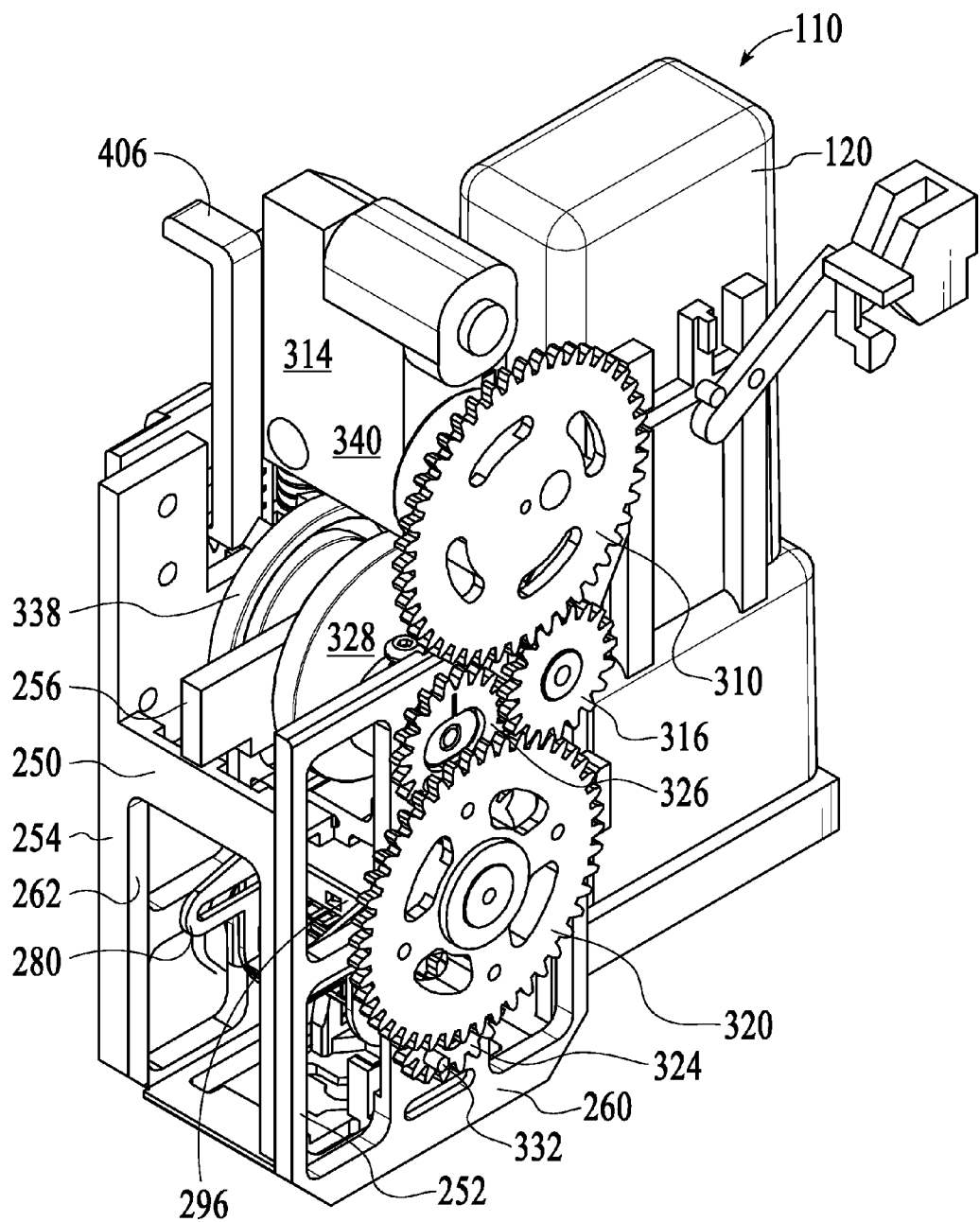
FIG. 8 is a perspective view of the lancing/collecting assembly of a medical diagnostic apparatus in accordance with an alternative embodiment.
Figure 9:
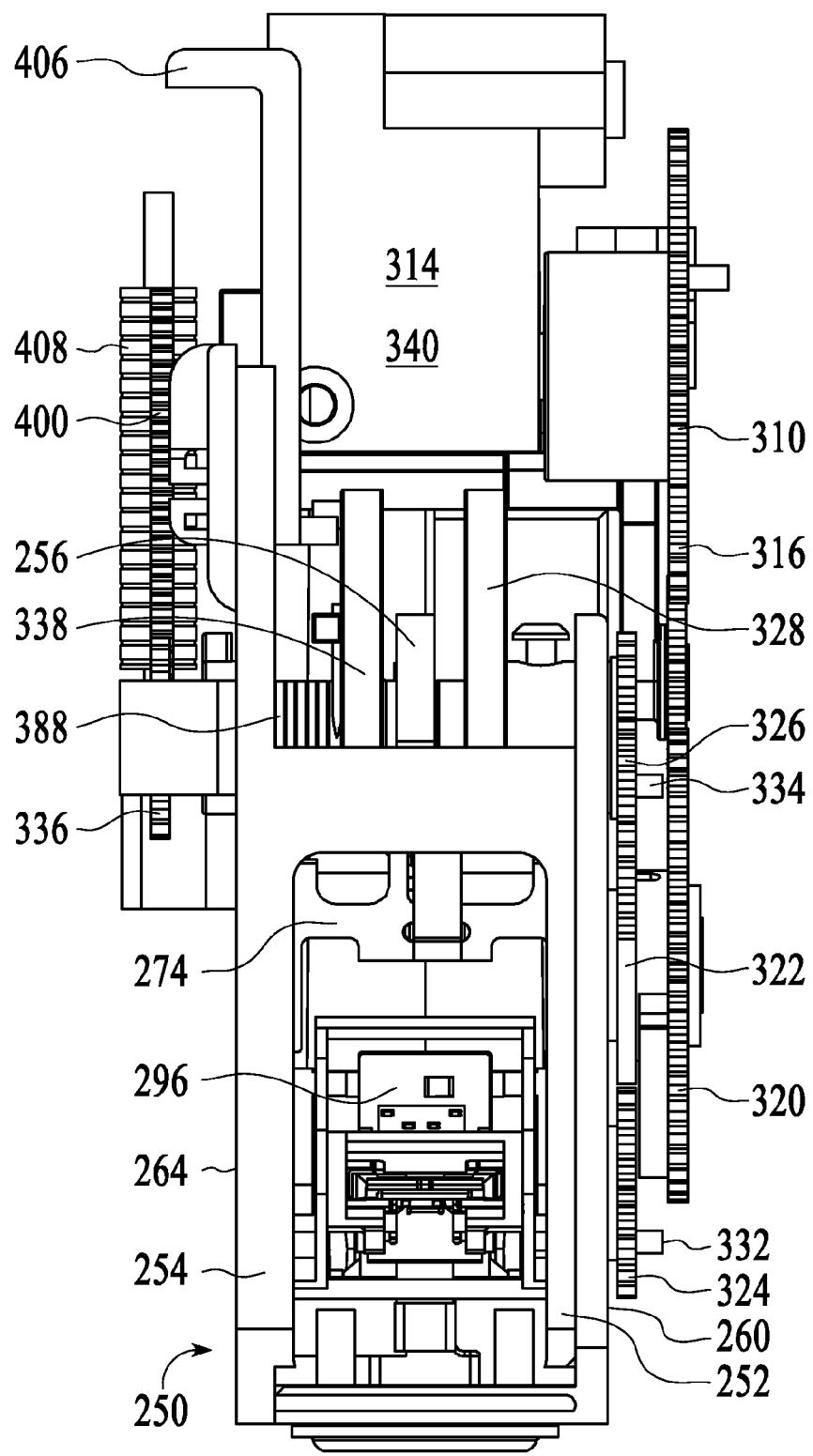
FIG. 9 is a front view in elevation of a medical diagnostic apparatus with a housing shown attached to an end cap and a tub.
Figure 10A:
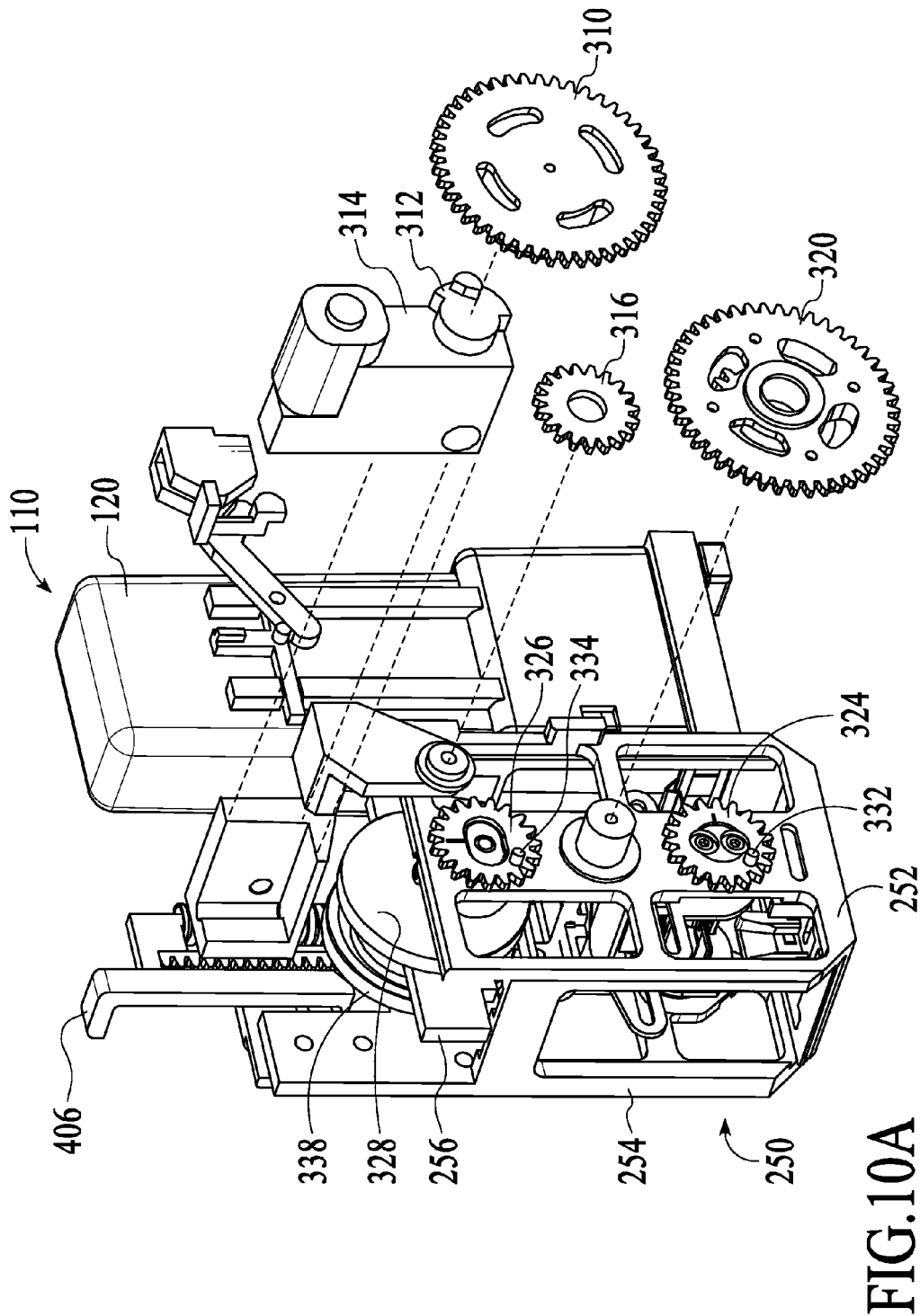
FIGS. 10A and 10B are exploded perspective views of the lancing/collecting assembly of the medical diagnostic apparatus in accordance with an alternative embodiment.
Figure 10B:
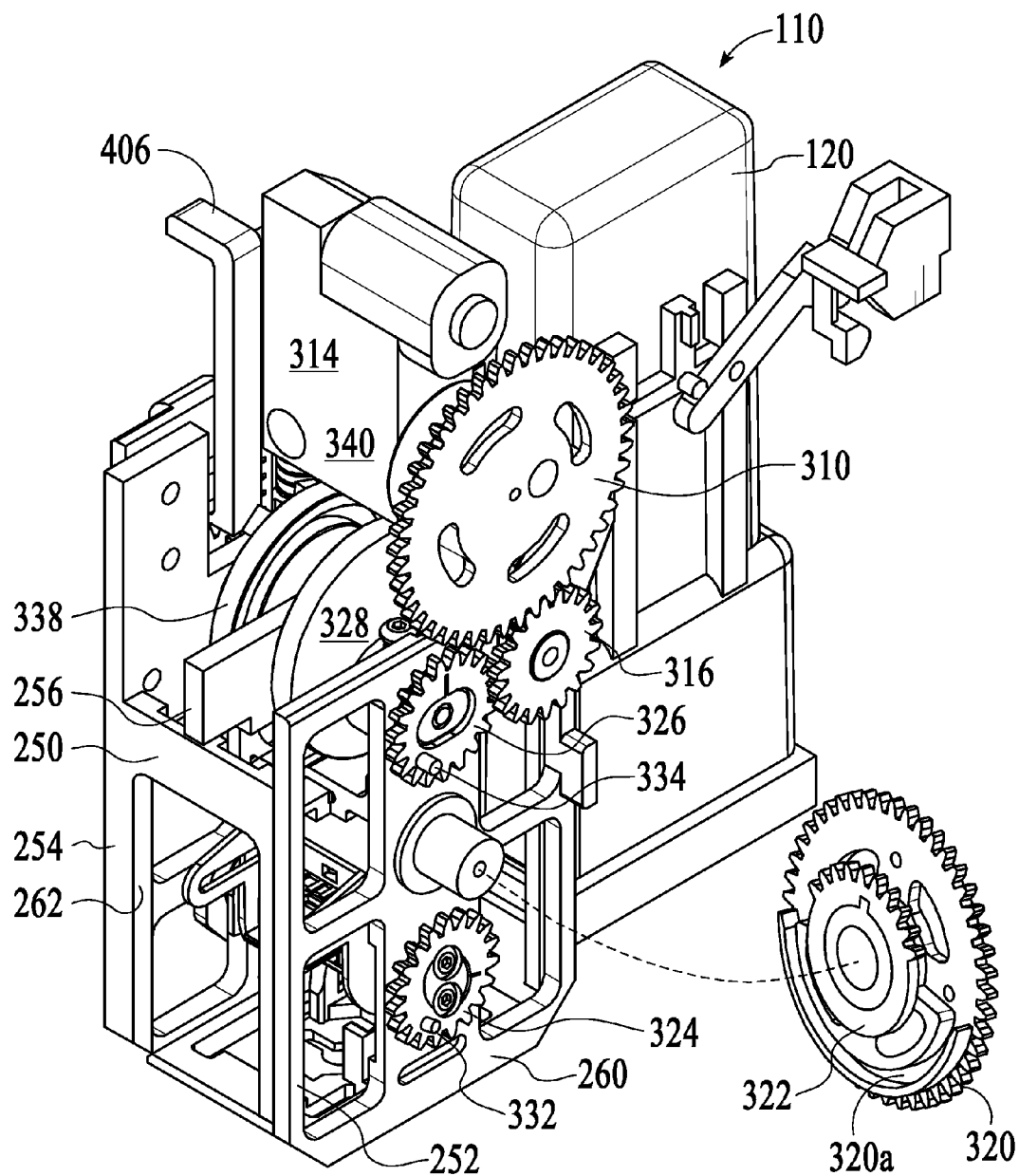
Figure 11:
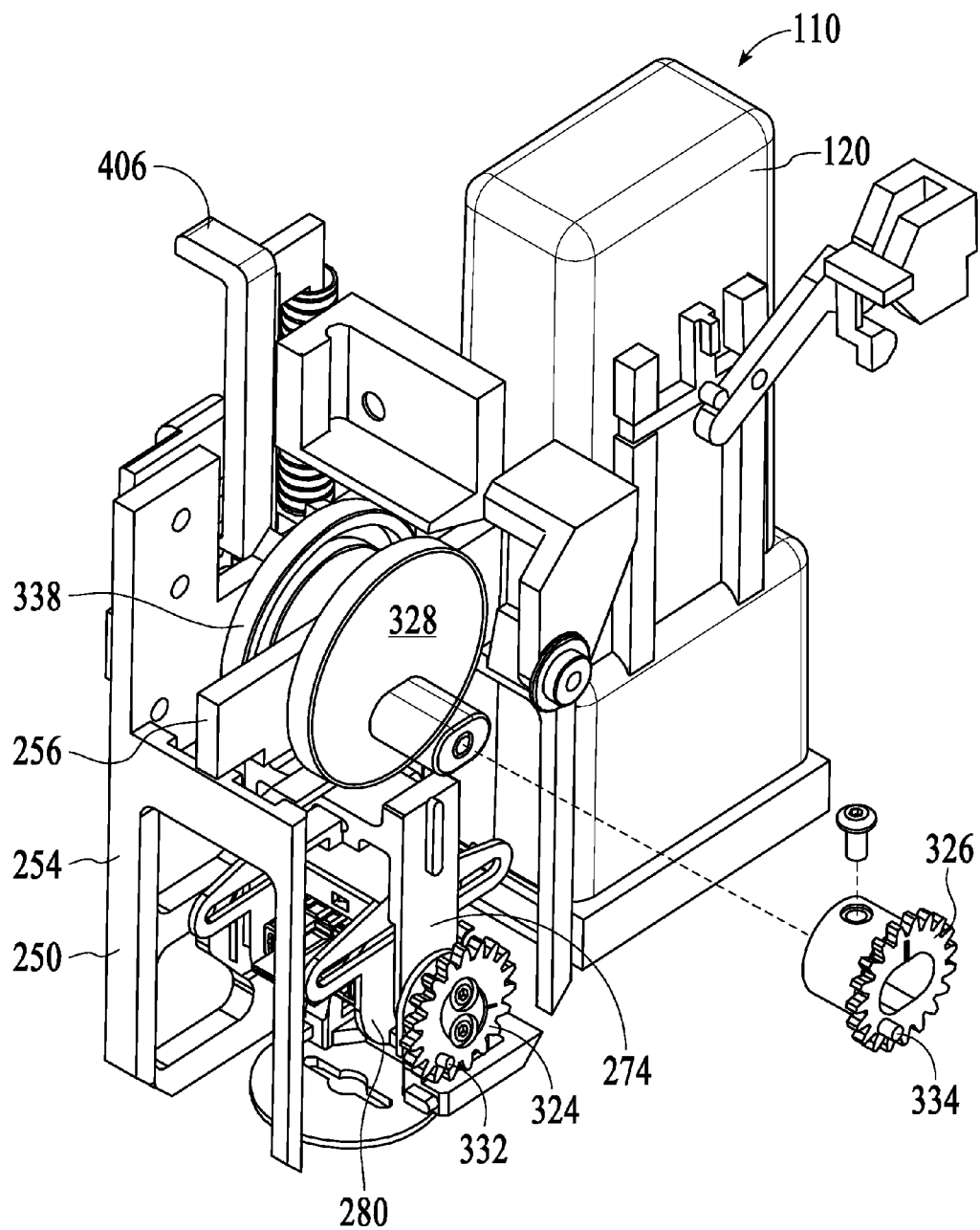
FIG. 11 is another exploded perspective view of a lancing/collecting assembly of a medical diagnostic apparatus in accordance with an alternative embodiment. In this view, part of the frame is shown as being broken away.
Figure 12:
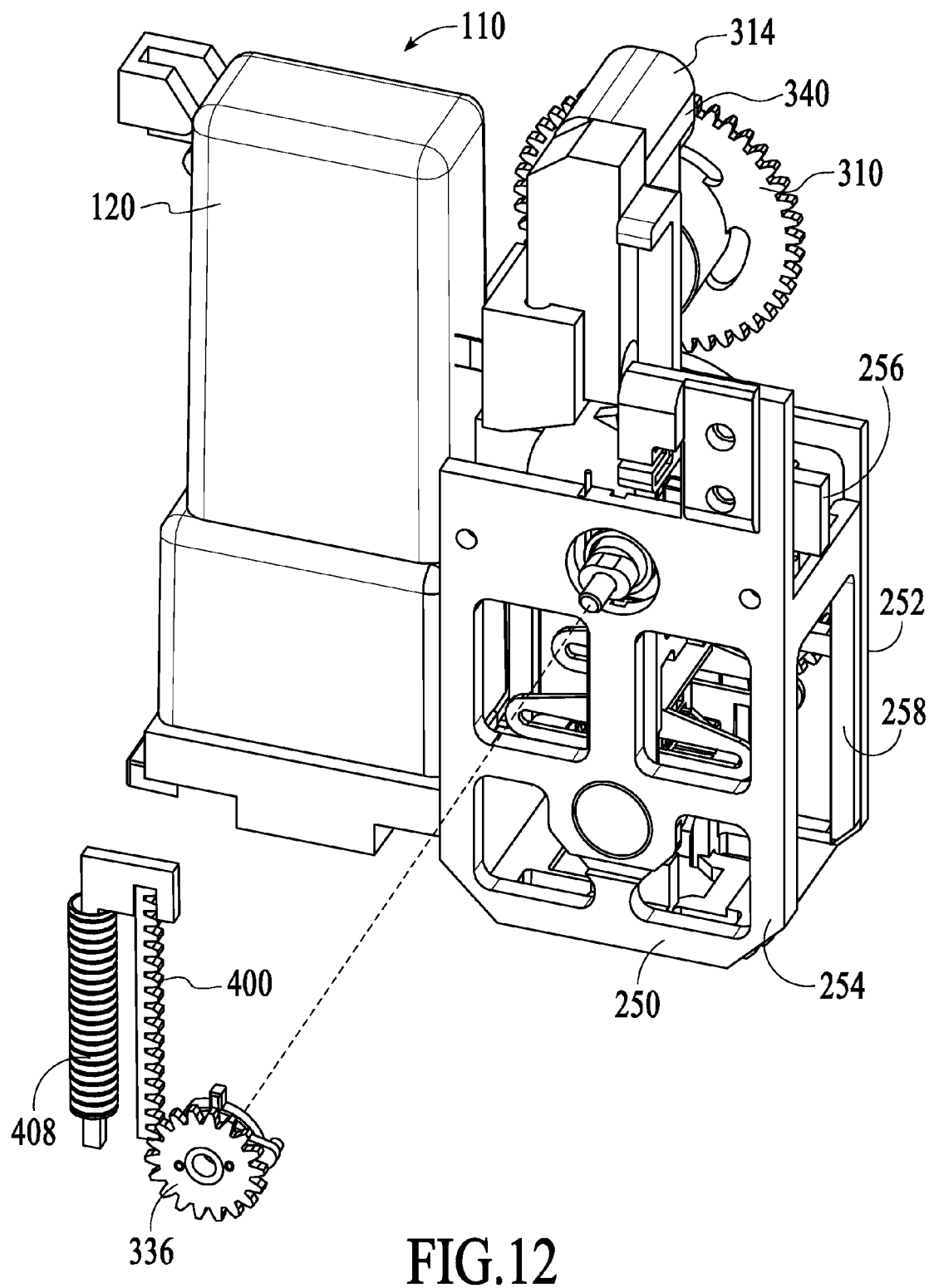
FIG. 12 is another exploded perspective view of a lancing/collecting assembly of a medical diagnostic apparatus of an alternative embodiment. This view shows a side of the lancing/collecting assembly not shown in FIGS. 8, 10A, 10B, and 11.
Figure 13:
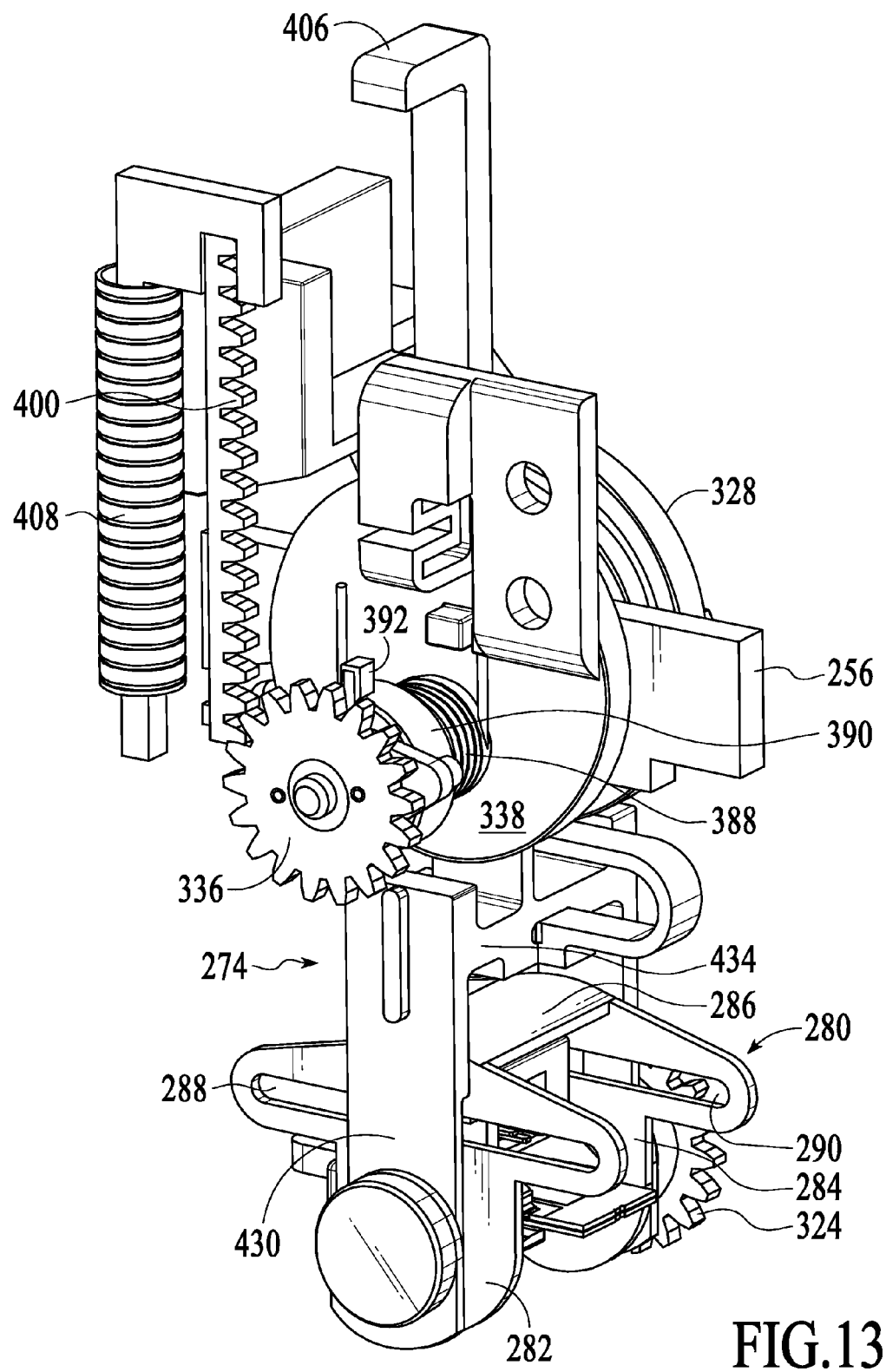
FIG. 13 is another exploded perspective view of a lancing/collecting assembly of a medical diagnostic apparatus of an alternative embodiment. This view shows a side of a lancing/collecting assembly not shown in FIGS. 8, 10A, 10B, and 11. In this view, the frame has been removed.
Figure 14:
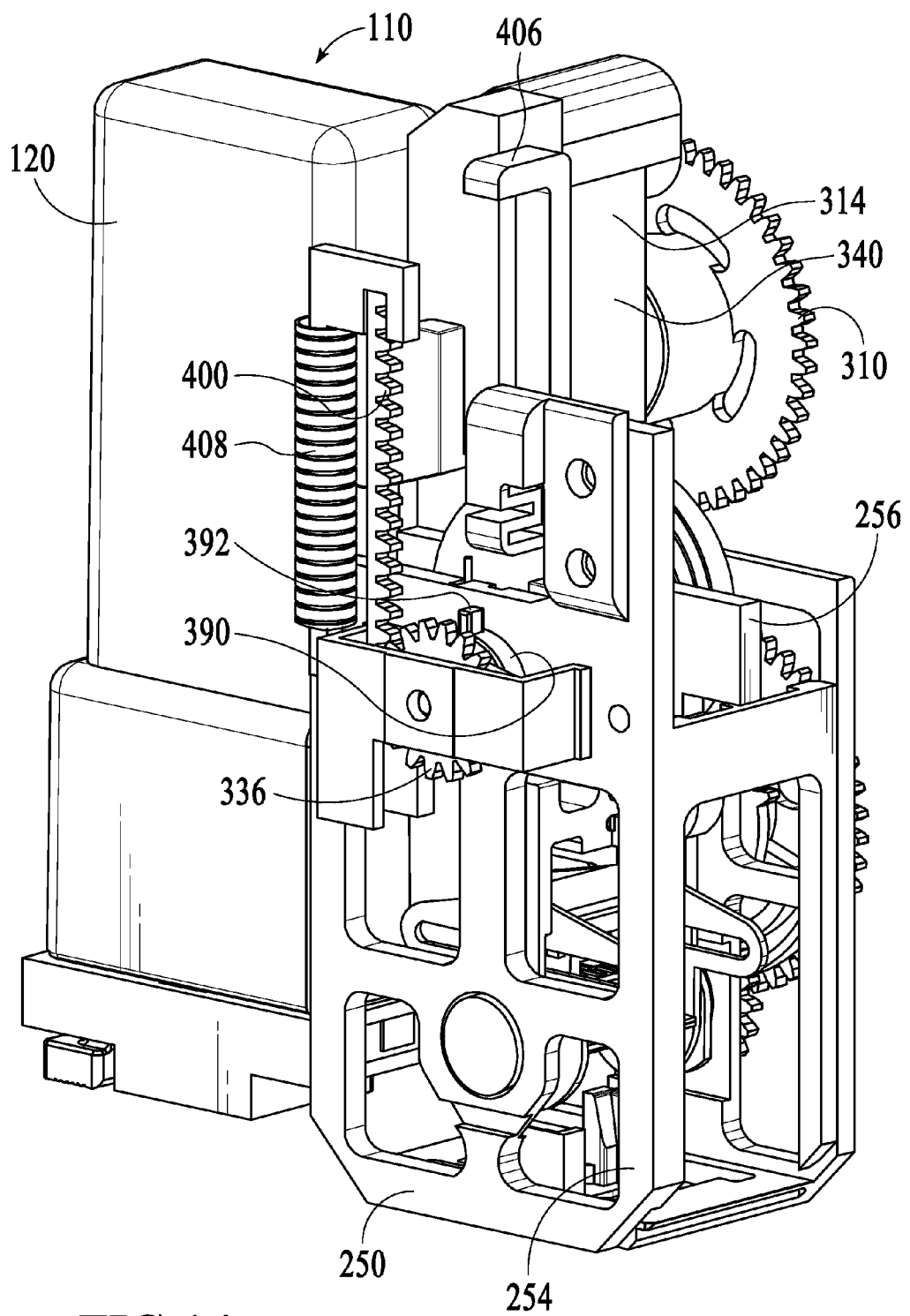
FIG. 14 is a perspective view of a side of a lancing/collecting assembly of a medical diagnostic apparatus of an alternative embodiment not shown in FIGS. 8, 10A, 10B, and 11. In this view, the frame is included.
Figure 15:
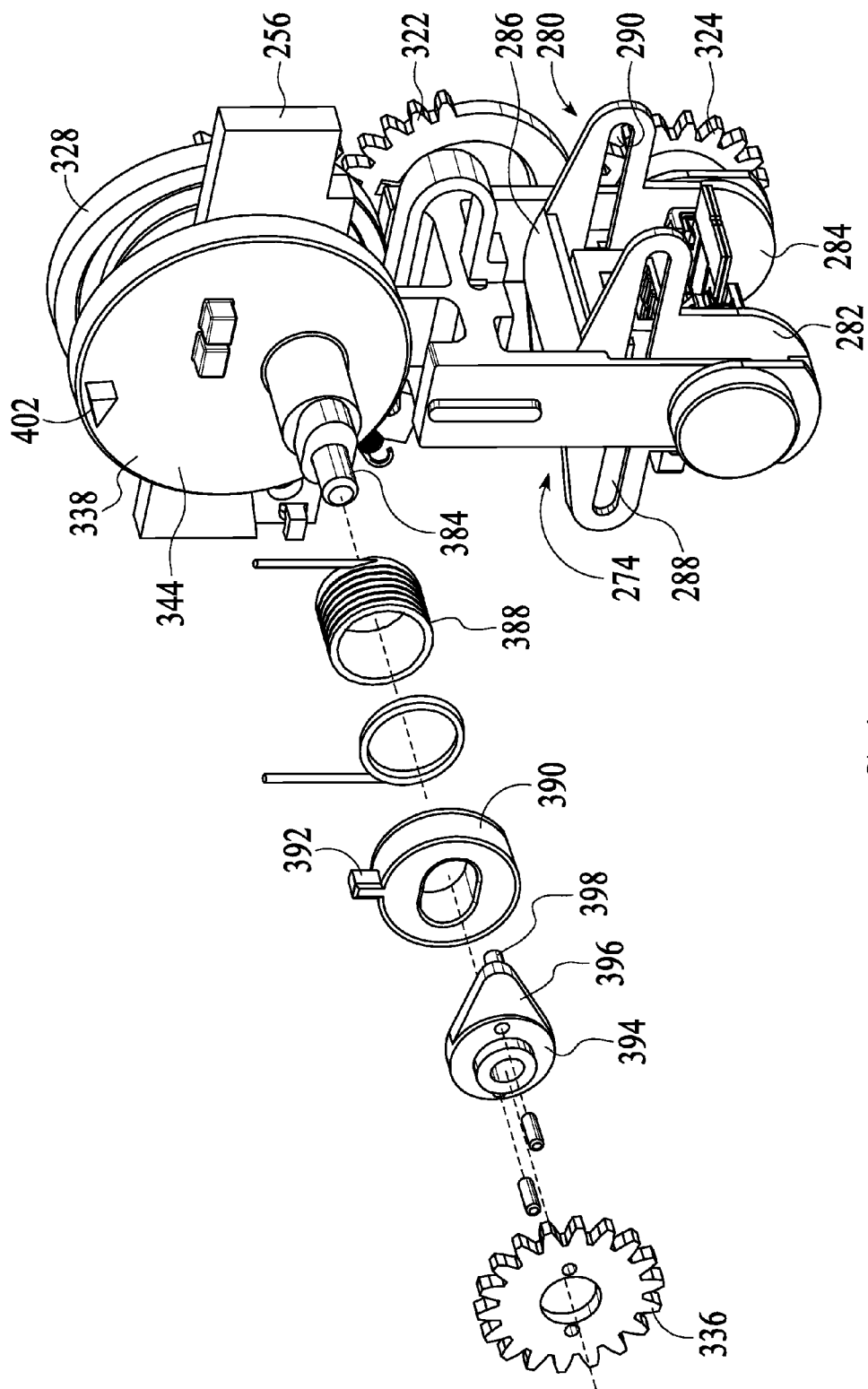
FIG. 15 is an exploded perspective view of one side of a lancing/collecting assembly of a medical diagnostic apparatus of an alternative embodiment. In this view, the components required for arming the lancet are displayed without any obscuring barrier.
Figure 16:
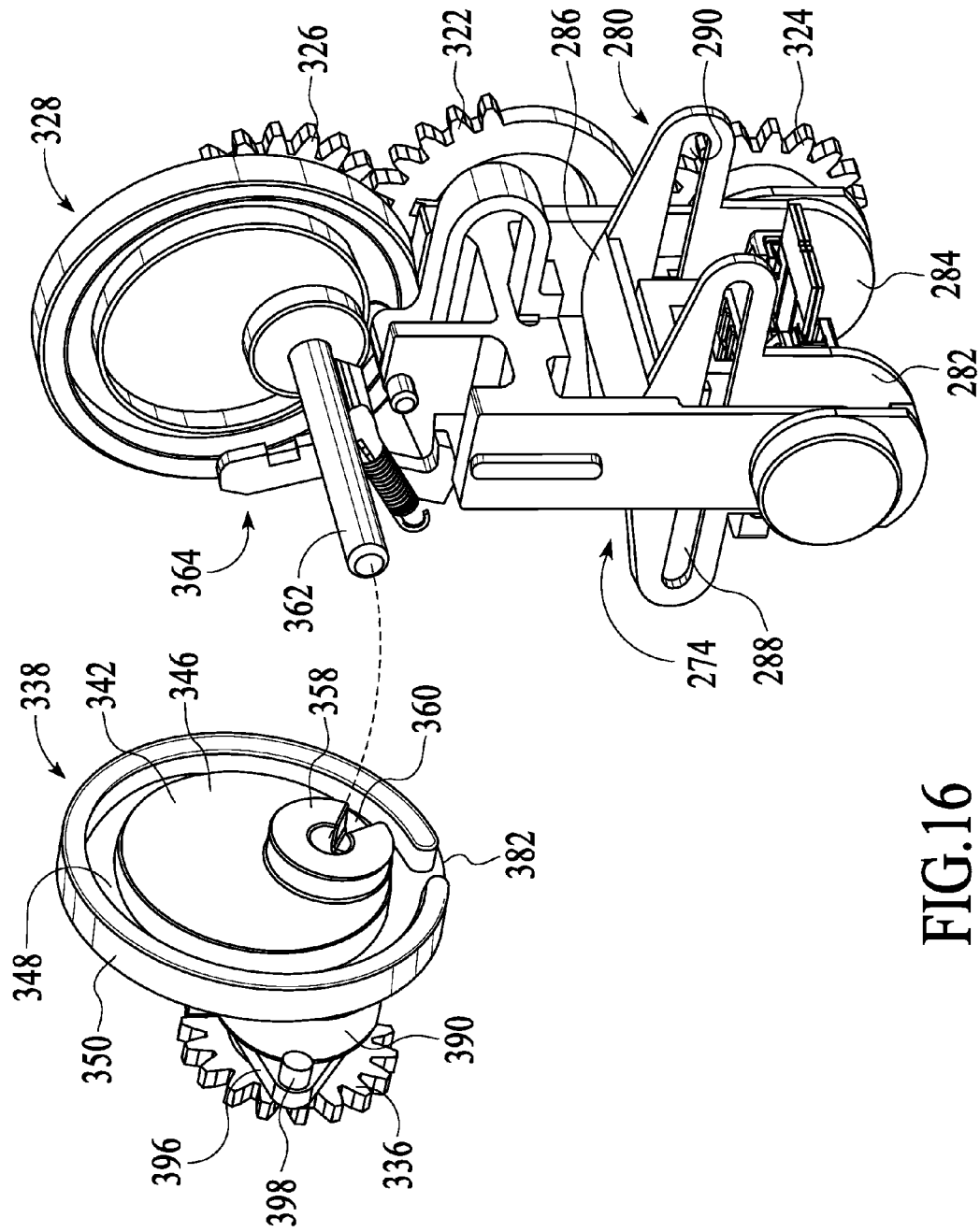
FIG. 16 is an exploded perspective view of selected components of a lancing/collecting assembly of a medical diagnostic apparatus of an alternative embodiment.

A track 229 is shown in FIG. 6B along which a pusher P, not shown but which may be a flexible piece such as a uniformly flexible plastic or a chain with a suitable end piece for contacting the striplet, see FIGS. 7A-7P, moves to advance the striplet into the turret 225, or permit it to retreat into the housing 110, 110a. The pusher P may lead a chain drive, or a highly flexible uniform plastic and/or another flexible material such as a metal such as stainless steel. The pusher P and drive mechanism may itself be a single piece or multiple pieces like a chain drive. The flexible pusher mechanism, including the pusher P and the drive mechanism, may wind and unwind from a coil to advance when it unwinds and retreat when it winds. FIG. 6F illustrates this feature. The unwinding coil may follow the track 229 to push the striplet through port both when the striplet is in a lancing orientation and when the striplet is re-oriented for testing. FIG. 6F illustrates a Buehler KNO4 rotary drive system, which can be used to provide a linear drive mechanism for advancing a striplet. The system shown in FIG. 6F includes a DC gear motor (e.g., Mabuchi DC motor-3V DC) and solid height spring in coil form.

The pusher P may also simply extend along a long dimension of the housing and turn at a corner, with the help of a curved inner wall surface such that the track 229 is formed between an outer wall of the housing or a proximate attachment thereto and the curved inner wall surface. The pusher P may even bend around two or three corners of the housing, and may be condensed in various ways when it is in the retreated position so that it is long enough to extend sufficiently when advancing the striplet and yet is maintained inside the housing out of the way of other components when retreated.

In operation, the pusher P moves along track 229 and meets with a loaded striplet pushing it into the turret 225. The striplet is rotated 90 degrees and advanced through port 231 for lancing. The striplet retreats some and is rotated or flipped by re-orientation mechanism 224, including cam 226, as the striplet remains within slot 299 of turret 225. The striplet is re-oriented by 180 degrees, or another angle equal to the angle between the lancet and testing area of the strip portion of the striplet, so that it can advanced again through the port 230a so that test sensor end 1002 of the striplet now exits port 230a and bodily fluid, e.g., blood, is applied for testing a body analyte, e.g., glucose, level such as a blood glucose, or ketone or other analyte level. After testing, the striplet is rotated 90 degrees or whatever the angle between the ejection port and the lancing and testing port relative to the turret's or striplet's rotational center, and is ejected through port 231 with lancet cap covering lancet for safety. The pusher P may be used a second time for assisting in the ejecting of the used and recapped striplet 1000a.

Figure 6G:
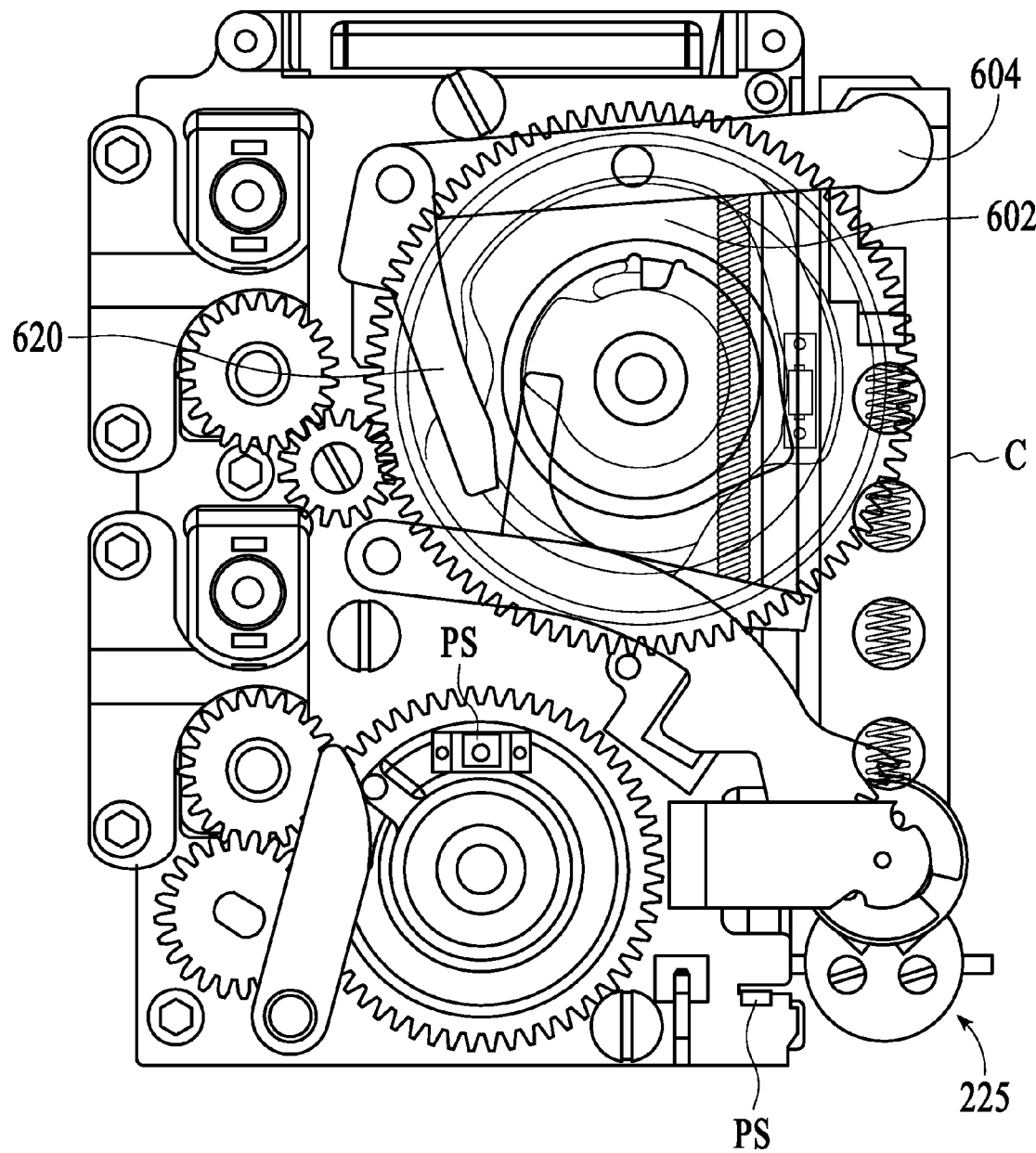
FIG. 6G illustrates an exemplary embodiment showing a side view with some transparencies of mechanical components of an integrated meter.

FIG. 6G illustrates an exemplary embodiment showing a side view with some transparencies of mechanical components of an integrated meter. A main gear 602 or drive gear 602 is shown partially transparent for illustration. Gear 602 is coupled with a cam which is not visible in FIG. 6G, but which controls cam follower 604. A carriage C is shown including a turret 225, and these components are further illustrated at FIGS. 7A-7P and described below. FIG. 6G also illustrates multiple photosensors PS that are used for monitoring various movements and status of a lancing and testing process performed with the integrated meter. Optical signals are received at photosensors PS, which may or may not also emit optical signals that are reflected back, for providing information to a microprocessor and/or other meter control circuitry.

Figure 6H:
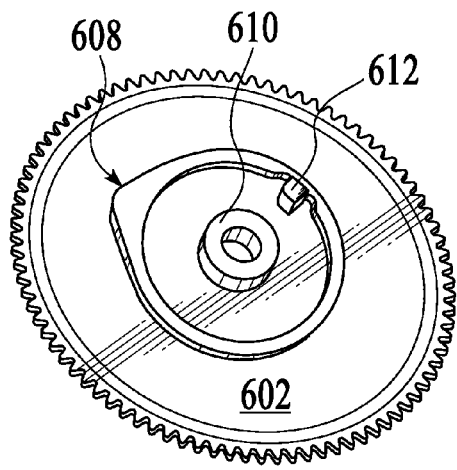
FIGS. 6H-6I illustrate front and back views of a main drive gear of an integrated meter according to an embodiment.
Figure 6I:
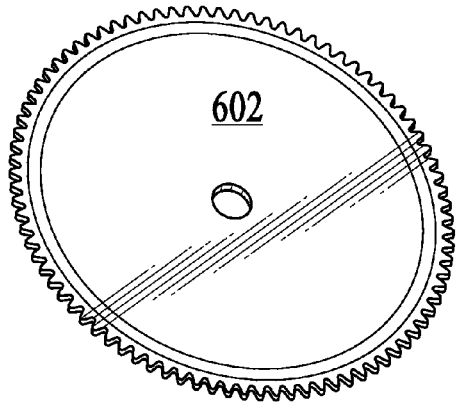

FIGS. 6H-6I illustrate front and back views of a main drive gear of an integrated meter according to an embodiment. The front of the main gear 602 includes a central ring-like portion that has a nub 608, and a hook 610 and post 612 for a clock spring (not shown). When the nub 608 is at about the 7 o-clock position, nub 608 causes lever 620 to rotate clockwise releasing a disk gear 630 or cam gear 630.

Figure 6L:
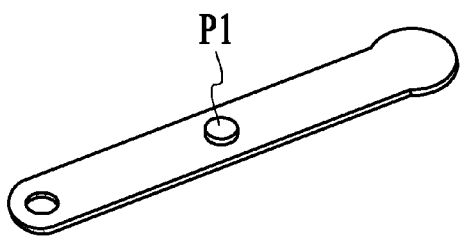
FIGS. 6L-6M illustrates front and back views of cam follower of an integrated meter according to an embodiment.
Figure 6M:
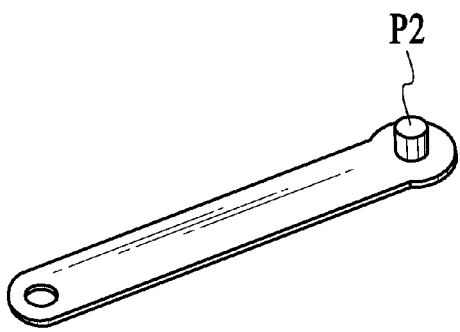
Figure 6J:
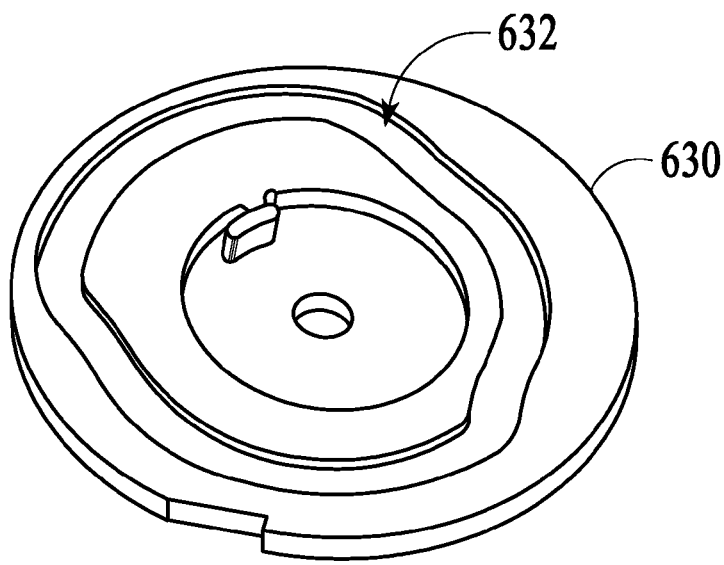
FIGS. 6J-6K illustrate front and back view of a disk or cam gear of an integrated meter according to an embodiment.
Figure 6K:
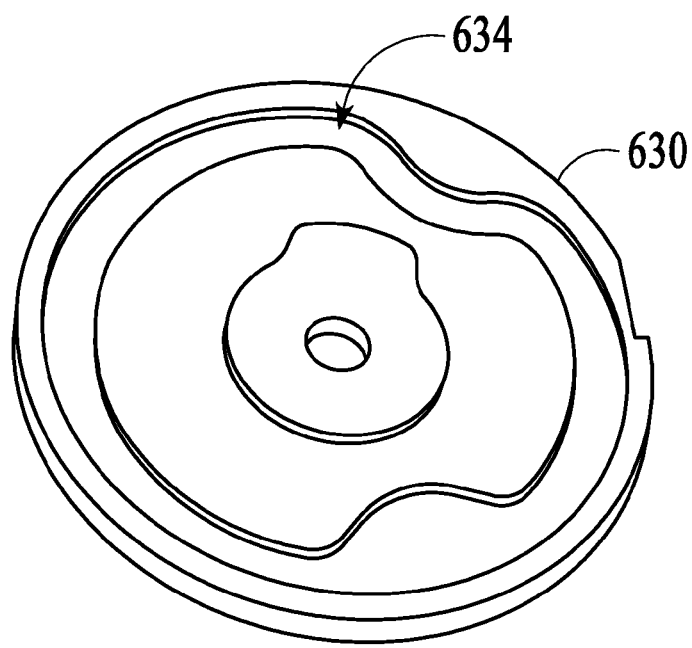

FIGS. 6J-6K illustrate front and back views of the disk gear 630 or cam gear 630 of an integrated meter according to an embodiment. The clock spring interfaces between the main gear 602 and the cam gear 630. Two cam paths 632 and 634 are defined in the cam gear, one or either side.

FIGS. 6L-6M illustrates front and back views of cam follower 604 of an integrated meter according to an embodiment. Cam follower 604 includes pivots P1 and P2 which follow cam paths 632 and 634.

FIGS. 7A-7P illustrate an operational sequence of a medical diagnostic apparatus in accordance with an embodiment. FIG. 7A shows the medical diagnostic apparatus of this embodiment. The turret 225 is shown with the positions of lancing and testing port 231 and ejection port 230a pointed out. Track 229 has a chain therein which is led by pusher P. The cartridge 110a is closed with seal 130 in place sealed with a tub T. Seal 130 may utilize an o-ring type seal. Tub T includes centering element 233, which centers a next striplet for precision loading onto track 229 for permitting the striplet and pusher P to be precisely relatively disposed. A blade B is also illustrated awaiting its time to move downwardly for uncapping a lancet of a striplet 1000a.

FIG. 7B shows the tub T moved down breaking the seal 130 with tub T to expose a striplet 1000a. The striplet 1000a is loaded from the cartridge 110a onto track 229 guided by centering element 233.

The tub T may include a guide platform for positioning a striplet while retreating from the cartridge 110a. The striplet may therefore be loaded with precision onto the guide track segment from which a pusher P matches a contour of the lancet end of the striplet and advance the striplet into the turret 225.

FIG. 7C shows the pusher P advanced to meet the striplet 1000a. The tub T continues to be in the downward position while the track 229 is exposed.

FIG. 7D shows the pusher P after having pushed the striplet 1000a into turret 225. The strip end 1002a of the striplet 1000a is pushed through first, while the lancet end 1004a of the striplet 1000a is behind.

At FIG. 7E, a blade B or decapping lever moves down to engage the lancet cap 1204a. A ridge on the lancet cap 1204a allows a contour of the blade B to couple therewith.

The chain retracts as shown in FIG. 7F rotating the blade B slightly to permit the lancet cap 1204a to move rearward along with the chain and pusher P so that the lancet cap 1204a becomes removed from the lancet end 1004a of the striplet 1000a which remains in position in the turret 225.

Referring to FIG. 7G, now that the lancet cap 1204a is removed and retracted fully from the striplet 1000a, the turret 225 is rotated 90 degrees. This 90 degree rotation of the striplet 1000a orients the striplet 1000a with lancet 1004a first and strip 1002a behind, for being advanced through port 231 for lancing.

FIG. 7H illustrates a lancing position as the carriage C is moved relative to the rest of the meter apparatus for lancing. Alternatively, a mechanism for pushing only the striplet downward or only a turret section of the carriage downward may be provided.

Referring to FIG. 7I, the carriage C is moved back upward after the lancing or piercing of the skin of a diabetic at a lancing site. The turret 225 is rotated 180 degrees preparing for sensing. Note that the strip end 1002a is shown in FIG. 7I pointing toward port 231, while in FIGS. 7G and 7H, the lancet end 1004a was pointing toward port 231.

FIG. 7J illustrates how the carriage C is again moved downward this time for permitting body fluid appearing at the lancing site to be applied to the strip 1002a. Note that the lancet cap 1204a, blade B, and pusher P each remain in position while the lancing and testing occurs. The pusher P is overlapped with the cap 1204a, such that the blade holds both the cap 1204a and pusher P in place.

FIG. 7K shows the carriage C moved back upward, and the turret 225 having been rotated 90 degrees from when the body fluid was being applied to the strip 1002a. Now at FIG. 7L, the pusher P pushers the cap 1204a back onto the lancet end 1004a.

The striplet may protrude from the housing when loaded into the turret 225. The port 231 and 230a may be configured with a slot or may be two ends of a same cavity that curves around the two sides of the housing shown. In this way, the carriage C. advances the striplet for lancing and testing, and the turret 225 may remain translationally fixed relative to the carriage C. The turret 225 may alternatively move to expose either end of the striplet through either port. In another embodiment, the carriage C does not move, while the turret 225 translates to expose the ends of the striplet in turn through port 231.

FIG. 7M shows the decapping lever or blade B moved back up disengaging from the lancet cap 1204a and pusher P. FIG. 7N shows the ejecting of the striplet 1000a. The pusher P is shown after having advanced to push the striplet 1000a through port 230a.

At FIG. 7O, the pusher P is retracted back to the start position on the track 229 that it was in at FIG. 7A. Now the pusher P is out of the way of the tub T, which can move back up as shown at FIG. 7P and meet again with seal 130 to protect the striplets from ambient air and moisture until a next testing is to be performed.

Referring now to FIGS. 8-12, inclusive, the lancing/collecting assembly 112 includes a frame 250 having two upright members 252 and 254 and a horizontal member 256. The upright member 252 has an inner face 258 and an outer face 260. The upright member 254 has an inner face 262 and an outer face 264. The inner face 258 and the outer face 260 are bounded by a top edge 266a, a bottom edge 266b, and two side edges 266c and 266d. The inner face 262 and the outer face 264 are bounded by a top edge 268a, a bottom edge 268b, and two side edges 268c and 268d. The inner face 258 has a track 270 and the inner face 262 has a track 272 for guiding the movement of a cam follower 274. The inner faces 258 and 262 of the upright members 252 and 254, respectively, of the frame 250 face one another. The horizontal member 256 of the frame 250 has a top edge 276a, a bottom edge 276b, two side edges 276c, 276d, and two faces 276e, 276f. One of the faces 276e of the transverse member 256 of the frame 250 faces one of the upright members 252 of the frame 250 and the other face 276f of the horizontal member 256 of the frame 250 faces the other of the upright members 254 of the frame 250.

Referring now to FIGS. 11, 13, and 15-22, inclusive, the lancing/collecting assembly 112 includes a cradle 280. The purpose of the cradle 280 is to hold a test strip during both the lancing step and the sample collecting step, which are carried out by the medical diagnostic device 100. Another purpose of the cradle 280 is to orient a test strip during the lancing step and the sample collecting step so that the lancet of the lancet-containing portion of the test strip can form an opening in the skin of the patient during the lancing step and the sensor of the sensor-containing portion of the test strip can collect the sample of biological liquid emerging from the opening in the skin of the patient during the sample collecting step. In the embodiment shown in FIGS. 1-22, inclusive, the cradle 280 also holds the test strip during the analyzing step. The cradle 280 includes two upright members 282 and 284 and a transverse member 286. The transverse member 286 of the cradle 280 connects the two upright members 282 and 284 of the cradle 280. The upright member 282 of the cradle 280 has a slot 288 formed therein, and the upright member 284 of the cradle 280 has a slot 290 formed therein. The slots 288 and 290 receive an L-shaped element 292 and 294, respectively, formed on a carrier 296. The L-shaped element 292 has a foot 292a and a leg 292b. The L-shaped element 294 has a foot 294a and a leg 294b. The foot 292a of the L-shaped element 292 and the foot 294a of the L-shaped element 294 are capable of sliding in the slots 288 and 290, respectively, of the cradle 280 during the lancing step and the sample collecting step so that the lancet of the lancet-containing portion of the test strip can form an opening in the skin of the patient during the lancing step and the sensor of the sensor-containing portion of the test strip can collect the sample of biological liquid emerging from the opening in the skin of the patient during the collecting step. The sliding motion of the foot 292a and the foot 294a is brought about by the movement of the cam follower 274 during the lancing step and during the sample collecting step. The upright member 282 of the cradle 280 further contains a track 298 formed therein, and the upright member 284 of the cradle 280 further contains a track 300 formed therein, each of which tracks 298 and 300 is of a size suitable for holding a test strip during the lancing and collecting functions of the medical diagnostic device, and in the embodiment shown in FIGS. 1-22, inclusive, the analyzing function.

The function of the carrier 296 is to house the electrical components and electronic components for completing a circuit when the test strip has received a sample of biological liquid from the patient. FIGS. 19-22, inclusive, shows how the carrier 296 receives and holds a test strip. The carrier 296, which is shown as a six-sided element, has a first L-shaped element 292 formed in one side 296a and a second L-shaped element 294 formed in an opposing side 296b, which L-shaped elements 292 and 294 are received by the slots 288 and 290, respectively, in the cradle 280. The leg 292b of the L-shaped element 292 and has a pin 292c, which pin 292c fits into and rotates in an aperture of the cam follower 274. Similarly, the leg 294b of the L-shaped element 294 and has a pin 294c, which pin 294c fits into and rotates in an aperture of the cam follower 274. The electrical and electronic components of the carrier 296, and the types of analyses that can be performed by the carrier 296 are described in detail in U.S. Pat. Nos. 6,299,757 and 6,616,819, the entireties of which are incorporated herein by reference.

Referring now to FIGS. 8-22, inclusive, the lancing/collecting assembly 112 includes a transmission system, including gears for (1) enabling operation of components required for a lancing operation for forming an opening in the skin of a patient, (2) collecting the sample of biological liquid emerging from the opening in the skin of the patient formed by the lancing operation, and (3) positioning a test strip during the analyzing operation. It should be noted that other configurations of gears, racks, can be used in place of the configuration shown in FIGS. 8-22, inclusive. It should be noted that transmission systems that utilize components other than gears can be used. The transmission system of the lancing/collecting assembly comprising the gears shown in FIGS. 8-22, inclusive, can be replaced in whole or in part by subsystems involving one or more racks and one or more pinions. Two important features of the medical diagnostic device 100 are that movement of the cam follower 274 can be effected in two directions, the directions being separated by approximately 180°, and that the cradle 280 or equivalent be capable of being rotated approximately 180° from a first position to a second position, the first position and the second position being separated by approximately 180°. As used herein, the expression "approximately 180°" means an angle ranging from about 160° to 200°, such as angles equal to or close to 180°.

Devices for mechanical transmission of power, or "mechanisms", constitute the basic units from which all kinds of devices are built. Every mechanism consists of individual elements whose movements in relation to one another are "positive", i.e., the motion of one element produces an accurately determinable and definable motion of every individual point of the other elements of that mechanism. Numerous combinations and modifications are possible, but only certain basic types of mechanisms will be noted here:

(1) Screw mechanism: When a screw spindle is rotated, the element attached to the nut will move in the longitudinal direction of the screw. Conversely, if the nut is rotatably mounted in the frame of the mechanism and driven, the screw spindle will move longitudinally.

(2) Linkage or crank mechanism: The characteristic element is the crank, which is rotatably mounted on a frame and is usually so designed that it can perform complete revolutions. Its motion is transmitted through the coupler (or connecting rod) to the lever (or rocker arm), likewise rotatably mounted, but not performing complete revolutions. Alternatively, instead of being connected to a lever, the coupler may be attached to a sliding element—e.g., a piston.

(3) Pulley mechanism: Connection between pulleys on their respective shafts is effected by flexible elements (belts, ropes).

(4) Ratchet mechanism: This serves to arrest a motion or to produce an intermittent rotation in the driven element. The pawl allows the ratchet wheel to rotate in one direction only, preventing rotation in the opposite direction by engaging the specially shaped teeth on the wheel.

(5) Gear mechanism: This type of mechanism, which is used extensively herein, transmits rotary motion from one shaft to another, usually in conjunction with a change in rotational speed and torque. In a gear mechanism of the usual type, the transmission is effected by the meshing of gear teeth, but in a friction-gear mechanism, this positive drive is replaced by frictional contact of wheels or rollers.

(6) Cam mechanism: This type of mechanism, which is used extensively herein, involves a cam mounted on a frame. The cam is driven and thereby moves a follower, which performs a desired predetermined motion depending on the shape of the cam.

Further information relating to the foregoing mechanisms can be found in *The Way Things Work*, Volume 2, Simon and Schuster (New York: 1971), pages 198-217, incorporated herein by reference.

Referring now to FIGS. 8-22, inclusive, a motor gear 310 is attached to a gear shaft 312 from the motor 314. The motor gear 314 drives an idler gear 316. The combination of motor gear 310 and idler gear 316 drives a first drive gear 320, which is attached to a second drive gear 322. As shown in FIGS. 8-22, inclusive, the first drive gear 320 is circular and has a greater diameter than the second drive gear 322. The second drive gear 322 is capable of driving both a gear 324 for rotating the cradle 280 and a gear 326 for rotating an index cam 328. The first drive gear 320 has teeth surrounding the entire periphery thereof. The second drive gear 322 is a sector gear, and contains teeth on only a portion of the periphery thereof. The first driven gear 324 is included for rotating the cradle 280. The second driven gear 326 is included for rotating the index cam 328. Both the first driven gear 324 and the second driven gear 326 have teeth surrounding the entire periphery thereof. The first driven gear 324 has a locking pin 332 projecting from the major surface thereof that faces the first drive gear 320. Similarly, the second driven gear 326 has a locking pin 334 projecting from the major surface thereof that faces the first drive gear 320. The locking pins 332 and 334 perform a variety of locking functions during the operation of the lancing/collecting assembly 112. The first drive gear 320 has a slot 320a formed therein for retaining the locking pins 332 and 334 during the operation of the lancing/collecting assembly 112. FIGS. 25A-25J, inclusive, show and TABLE 1 describes the positions of the locking pins 332 and 334 during one cycle of the medical diagnostic device 100.

TABLE 1

| FIG. | Activity | Position of cradle | Position of locking pin 332 of first driven gear 324 | Position of locking pin 334 of second driven gear 326 |
|---|---|---|---|---|
| 25A | Loading test strip | Horizontal | Free of slot 320a in drive gear 320 | In slot 320a in drive gear 320 |
| 25B | Lancing | Vertical (lancet facing down) | Free of slot 320a in drive gear 320 | In slot 320a in drive gear 320 |
| 25C | Disengaging first driven gear 324 | Substantially vertical (sensor facing down) | Entering slot 320a in drive gear 320 | In slot 320a in drive gear 320 |
| 25D | Capturing locking pin 334 of second driven gear 326 | Substantially vertical (sensor facing down) | Entering slot 320a in drive gear 320 | In slot 320a in drive gear 320 |
| 25E | Engaging second driven gear 326 | Substantially vertical (sensor facing down) | In slot 320a in drive gear 320 | Exiting slot 320a in drive gear 320 |
| 25F | Indexing (maximum depth) | Substantially vertical (sensor facing down) | In slot 320a in drive gear 320 | Free of slot 320a in drive gear 320 |
| 25G | Disengaging second driven gear 326 | Substantially vertical (sensor facing down) | In slot 320a in drive gear 320 | Entering slot 320a in drive gear 320 |

TABLE 1-continued

| FIG. | Activity | Position of cradle | Position of locking pin 332 of first driven gear 324 | Position of locking pin 334 of second driven gear 326 |
|---|---|---|---|---|
| 25H | Capturing locking pin 334 of second driven gear 326 | Substantially vertical (sensor facing down) | In slot 320a in drive gear 320 | Entering slot 320a in drive gear 320 |
| 25I | Engaging first driven gear 324 | Substantially vertical (sensor facing down) | Exiting slot 320a in drive gear 320 | In slot 320a in drive gear 320 |
| 25J | Loading test strip | Horizontal | Free of slot 320a in drive gear 320 | In slot 320a in drive gear 320 |

A lancing gear 336 is included for arming and firing a lancing cam 338. A gearbox 340 is also shown. The gearbox 340 contains those components that enable the second drive gear 322 to switch from driving the first driven gear 324, i.e., the gear for rotating the cradle 280, to driving the second driven gear 326, i.e., the gear for rotating the index cam 328. The gearbox 340 also contains those components that enable the drive gears to reverse their direction of rotation.

The lancing cam 338 is shown as having major surfaces that are circular in shape. The lancing cam 338 has an inner face 342 and an outer face 344. The inner face 342 contains a cylindrical element 346 formed thereon in such a manner that a circular path 348 is formed between the cylindrical element 346 and the peripheral edge 350 of the lancing cam 338. A pin 352 formed on a projection 354 on the cam follower 274 travels along this circular path 348 in order to enable the cam follower 274 to move in the direction desired for the particular operation being undertaken. Further projecting from the cylindrical element 346 of the inner face 342 is a substantially cylindrical projection 358 having a recess 360 formed in the periphery thereof. The purpose of the cylindrical projection 358 is to support one end of an axle 362 that traverses the distance between the lancing cam 338 and the index cam 328.

The purpose of the recess 360 in the cylindrical projection 358 is to receive a lock 364 to prevent the force of gravity from drawing the lancing cam 338 and the index cam 328 downwardly when the lancing cam 338 and the index cam 328 are not being operated. The lock 364 includes a hook portion 366, a resilient biasing element-retaining portion 368, and a cam-supporting portion 370. A resilient biasing element 372, e.g., a spring, one end of which is secured to the resilient biasing element-retaining portion 368 and the other end of which is secured to the frame 250, biases the lock 364 to the locked position. The lock 364 is released to enable movement of the lancing cam 338 and the index cam 328 merely by causing either the lancing cam 338 or the index cam 328 to be rotated a few degrees. The force generated by such rotation is sufficient to overcome the biasing force of the resilient biasing element 372.

The peripheral edge 350 of the lancing cam 338 has a portion 382 cut out to enable the pin 352 formed on the projection 354 of the cam follower 274 to enter the circular path 348 surrounding the cylindrical element 346 on the inner face 342 of the lancing cam 338. The lancing cam 338 has a lancing camshaft 384 projecting from the outer face 386 of the lancing cam 338. The lancing camshaft 384 is positioned eccentrically with respect to the outer face 386 of the lancing cam 338. Positioned on the lancing camshaft 384 is a torsion spring 388, which has the function of storing sufficient energy to enable the lancet of the lancet-containing portion of the test strip to be fired with sufficient force to form an opening in the skin of the patient. Located on the lancing camshaft 384, but facing the outer face 264 of the upright member 254 of the frame 250 is a ring 390 having a pin 392 projecting from the peripheral surface thereof. Adjacent to the ring 390 is a spring winder 394, which is permanently attached to the lancing gear 336. The spring winder 394 is cylindrical in shape and has an element 396 projecting from the periphery thereof. A pin 398 for contacting the pin 392 projecting from ring 390 projects from the end of the element 396. Upon rotation of the lancing gear 336 by a lancing rack 400, the lancing gear 336 drives the spring winder 394, whereby the element 396 brings about rotation of the ring 390 by means of rotating the pin 392 projecting from the periphery of the ring 390. After the ring 390 is rotated approximately 340-360°, a locking tab 402 on the face 344 of the lancing cam 338 abuts a locking tab 404 positioned on a trigger 406, thereby arming the medical diagnostic device 100. The teeth of the lancing gear 336 are capable of meshing with the teeth of the lancing rack 400.

In order to trigger the medical diagnostic device 100 so that the lancet of the lancet-containing portion of the test strip can form an opening in the skin of the patient and can subsequently be retracted from the opening so formed, the user merely actuates the trigger 406, such as, for example, by pushing a button, whereby the locking tab 404 disengages from the locking tab 402, and the energy stored in the torsion spring 388 causes the lancet of the lancet-containing portion of the test strip to be fired and subsequently retracted. Attached to one end of the lancing rack 400 is a lance return spring 408. During the lancing step, as the lancing rack 400 drives the lancing gear 336, the lance return spring 408 is expanded. The energy stored in the expanded lance return spring 408 is sufficient to enable retraction of the lancet of the lancet-containing portion of the test strip.

As described earlier with respect to the interaction between the cradle 280, the carrier 296, the L-shaped elements 292 and 294, the lancet-containing portion of the test strip, and the sensor-containing portion of the test strip, the lancet of the lancet-containing portion of the test strip is moved toward the skin of the patient to form an opening in the skin of the patient by means of movement of the cam follower 274, which causes the foot 292a of the L-shaped element 292 and the foot 294a of the L-shaped element 294, both of which are attached to the carrier 296, to slide in the slots 288 and 290, respectively, of the cradle 280. In the lancing step, the cam follower 274 is driven by the lancing cam 338.

The lancing cam 338 engages a pin 352 on the cam follower 274 when the cradle 280 is in either of two vertical positions (the position required for lancing the skin of a patient and the position required for collecting a sample of biological liquid from the patient). Because these positions are 180° apart, there are two engagement surfaces on opposite ends of the cradle 280. The sliding of the L-shaped elements 292 and 294 of the carrier 296 in slots 288 and 290 of the cradle 280 produces the required motions for forming an opening in the skin of the patient and collecting a sample of biological liquid from the opening formed in the skin of the patient.

The index cam 328 is shown as having major surfaces that are circular in shape. The index cam 328 has an inner face 410 and an outer face 412. The inner face 410 contains a cylindrical element 414 formed thereon in such a manner that a circular path 416 is formed between the cylindrical element 414 and the peripheral edge 418 of the index cam 328. A pin 420 formed on a projection 422 on the cam follower 274 travels along this circular path 416 in order to enable the cam follower 274 to move in the direction desired for the particular operation being undertaken. Further projecting from the cylindrical element 414 of the inner face 410 is a substantially cylindrical projection 424 having a recess 426 formed in the periphery thereof. The purpose of this cylindrical projection 424 is to support one end of an axle 362 that traverses the distance between the lancing cam 338 and the index cam 328. The index cam 328 has an index camshaft 428. The index camshaft 428 is positioned eccentrically with respect to the outer face 412 of the index cam 328.

After an opening is formed in the skin of the patient during the lancing step, and after the lancet-containing portion of the test strip is retracted, the test strip is oriented so that the sensor-containing portion of the test strip can collect a sample of biological liquid emerging from the opening in the skin of the patient. In the embodiment of the lancing/collecting assembly 112 shown herein, the mechanical transmission system orients the test strip by rotating the cradle 280 approximately 180° so that the sensor-containing portion of the test strip faces the opening in the skin of the patient. The mechanical transmission system then causes the index cam 328 to advance the test strip to the opening in the skin of the patient through the opening 117 in the end cap 104. Unlike the lancing step, no arming step or trigger step is required. However, the test strip moves in the same manner as it did during the lancing step, namely, the mechanical transmission system causes the index cam 328 to move the cam follower 274, which in turn causes the L-shaped elements 292 and 294 to slide in the slots 288 and 290 in the cradle 280, thereby enabling the sensor of the sensor-containing portion of the test strip to contact the sample of biological liquid emerging from the opening in the skin of the patient. The sensor of the sensor-containing portion of the test strip receives a sufficient quantity of the sample to carry out a determination of the analyte. In the embodiment of the lancing/collecting assembly 112 shown herein, the carrier 296 is designed to carry out the determination of the analyte. During the assay or after the completion of the assay, the cradle 280 is rotated 90° by the mechanical transmission system to position the test strip for re-attaching the protective cover to the used lancet of the lancet-containing portion of the test strip, removing the used test strip from the lancing/collecting assembly 112, and disposing of the used test strip through an ejection port 230 in the housing 102.

The cam follower 274 is a substantially U-shaped element having two upright members 430 and 432 that are connected by a transverse member 434. The upright member 430 has an aperture 436 into which the pin 292c projecting from the leg 292b of the L-shaped element 292 on the carrier 296 is received. The upright member 432 has an aperture 442 into which the pin 294c projecting from the leg 294b of the L-shaped element 294 on the carrier 296 is received. The upright member 430 of the cam follower 274 is disposed between the upright member 448 of an L-shaped projection 450 of the cradle 280 and the upright member 282 of the cradle 280. Similarly, the upright member 432 of the cam follower 274 is disposed between the upright member 454 of an L-shaped projection 456 of the cradle 280 and the upright member 284 of the cradle 280. Rotation of the pins 292c and 294c in the apertures 436 and 442, respectively, make it possible for the lancing/collecting assembly 112 to achieve all of the positions required to carry out the operations needed to (a) receive a test strip from the assembly for storing and dispensing test strips 110, (b) form an opening in the skin of the patient, (c) collect a sample of biological liquid emerging from the skin of the patient, and (d) remove the test strip form the lancing/collecting assembly 112.

Figure 17:
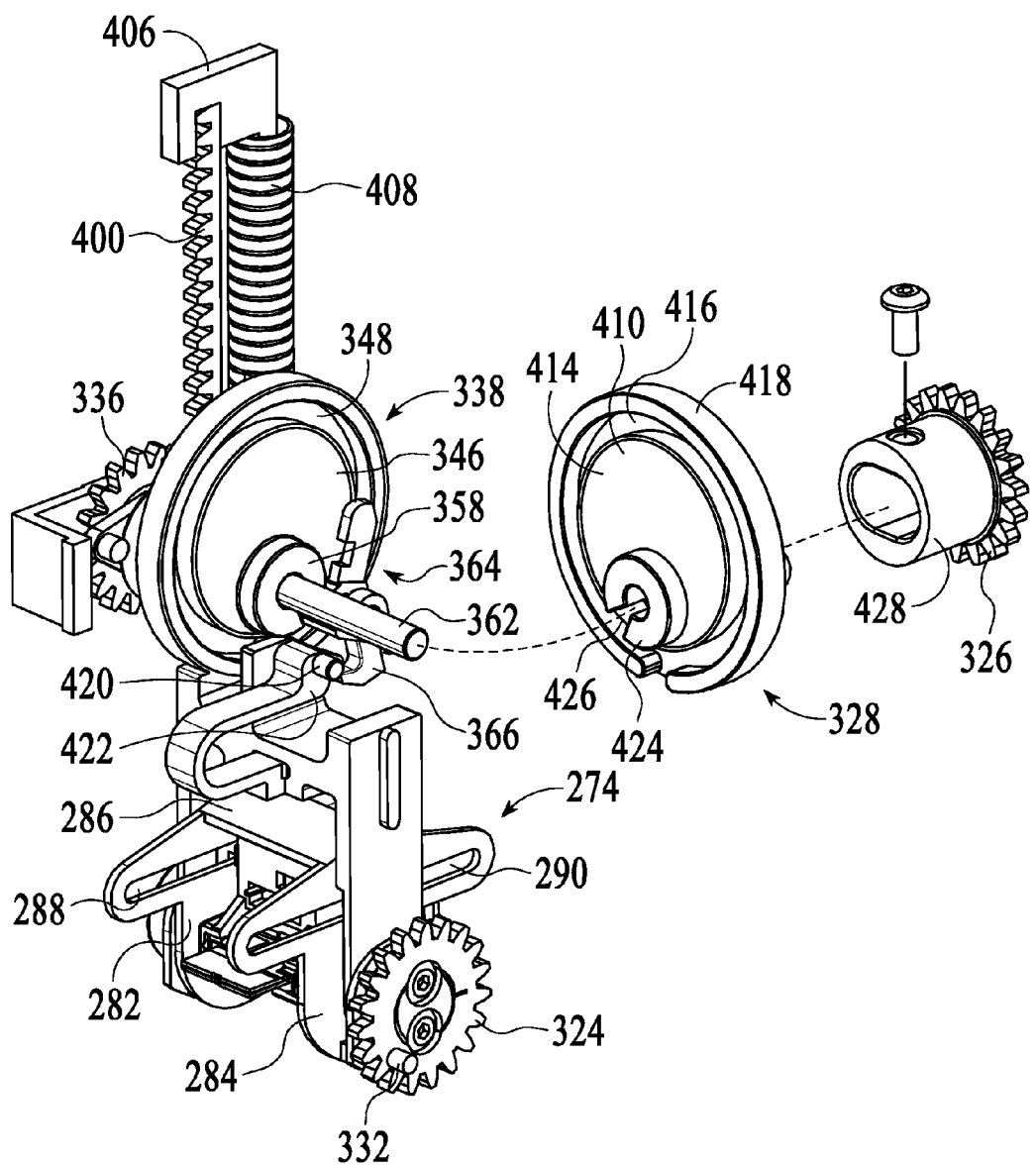
FIG. 17 is another exploded perspective view of selected components of a lancing/collecting assembly of a medical diagnostic apparatus of an alternative embodiment. This view shows a side of the lancing/collecting assembly not shown in FIG. 16.
Figure 18:
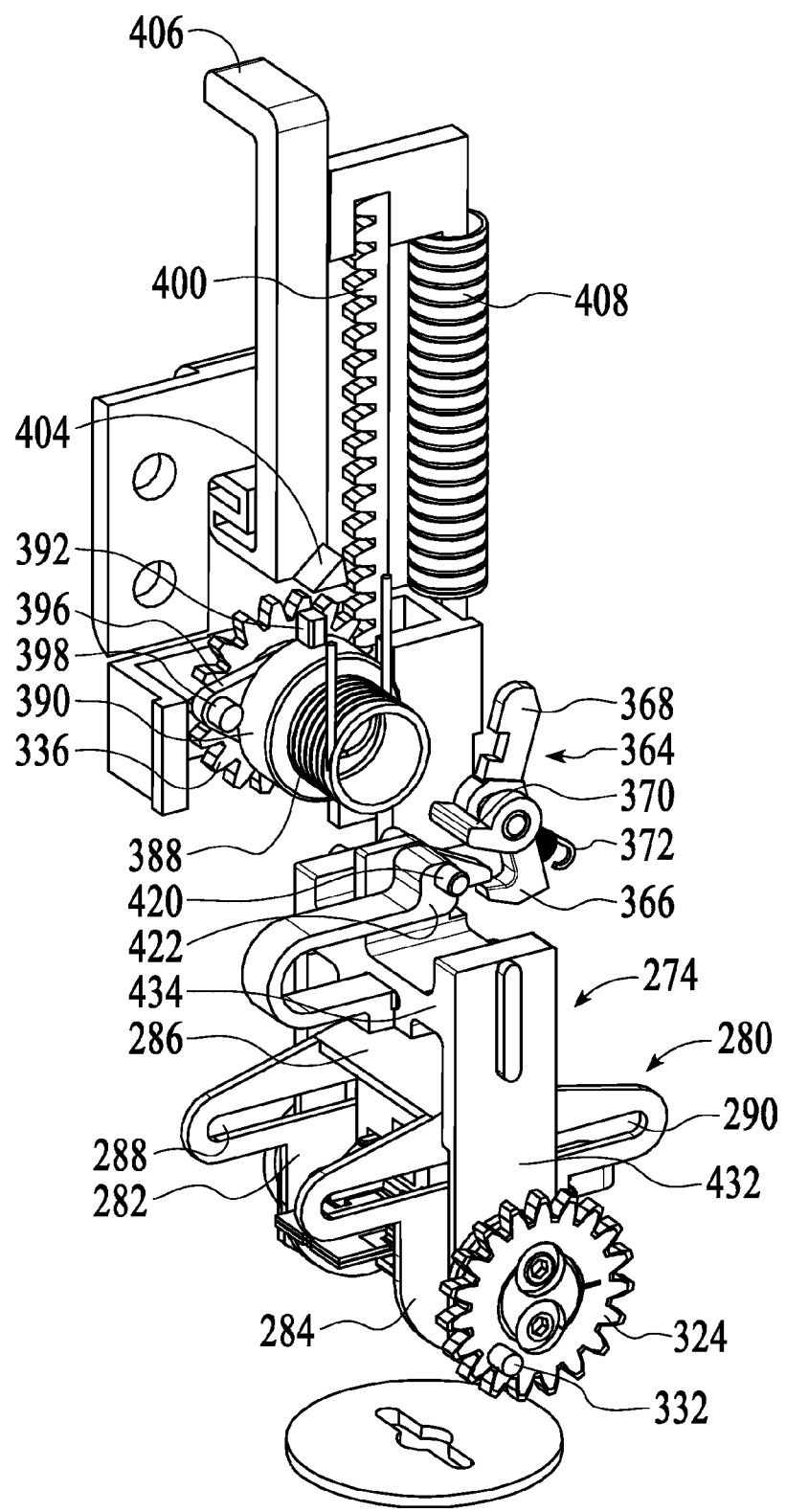
FIG. 18 is a perspective view of selected components for arming the lancet of a lancing/collecting assembly of a medical diagnostic apparatus of an alternative embodiment.
Figure 19:
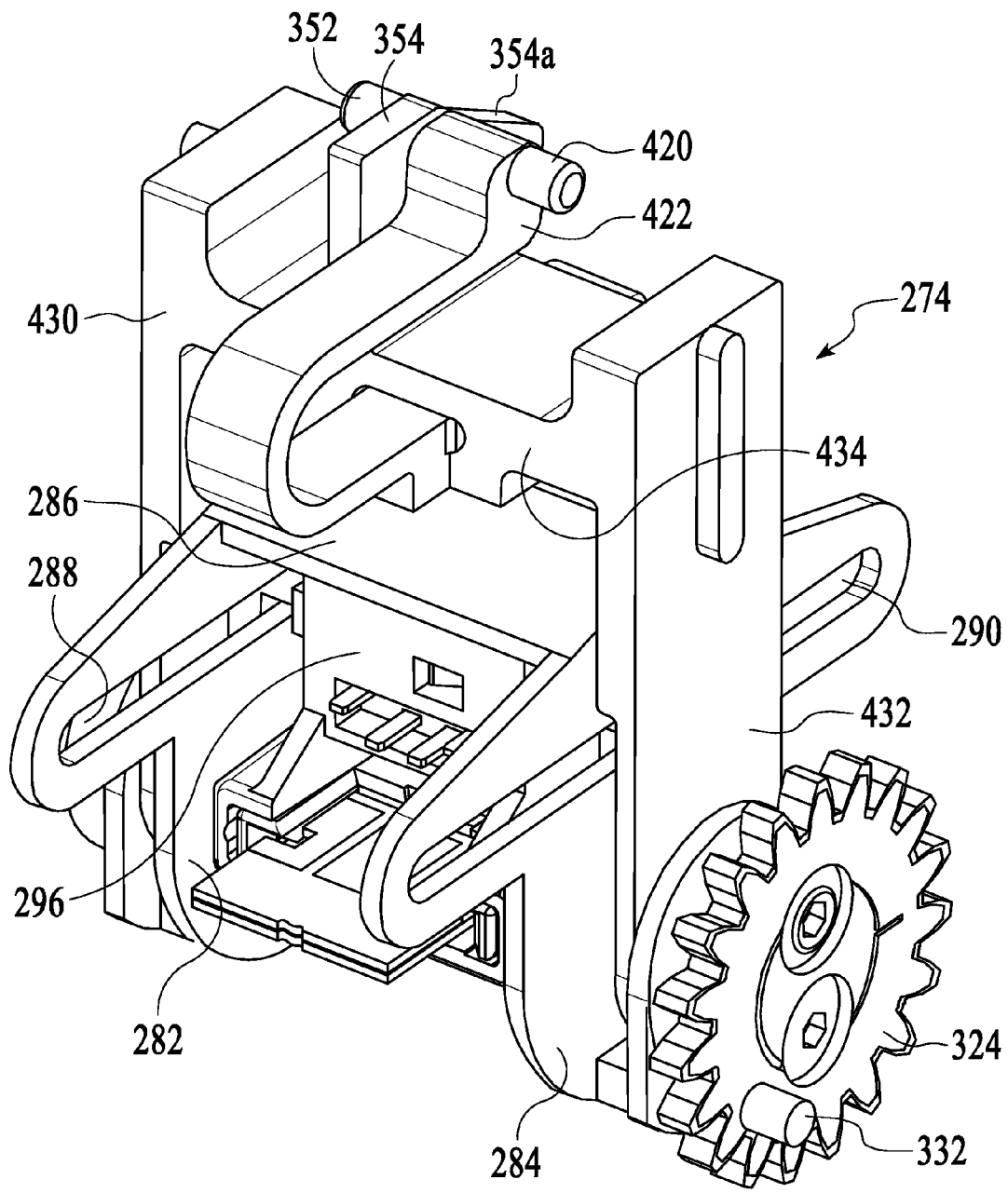
FIG. 19 is a perspective view of selected components of a lancing/collecting assembly of a medical diagnostic apparatus of an alternative embodiment.
Figure 20:
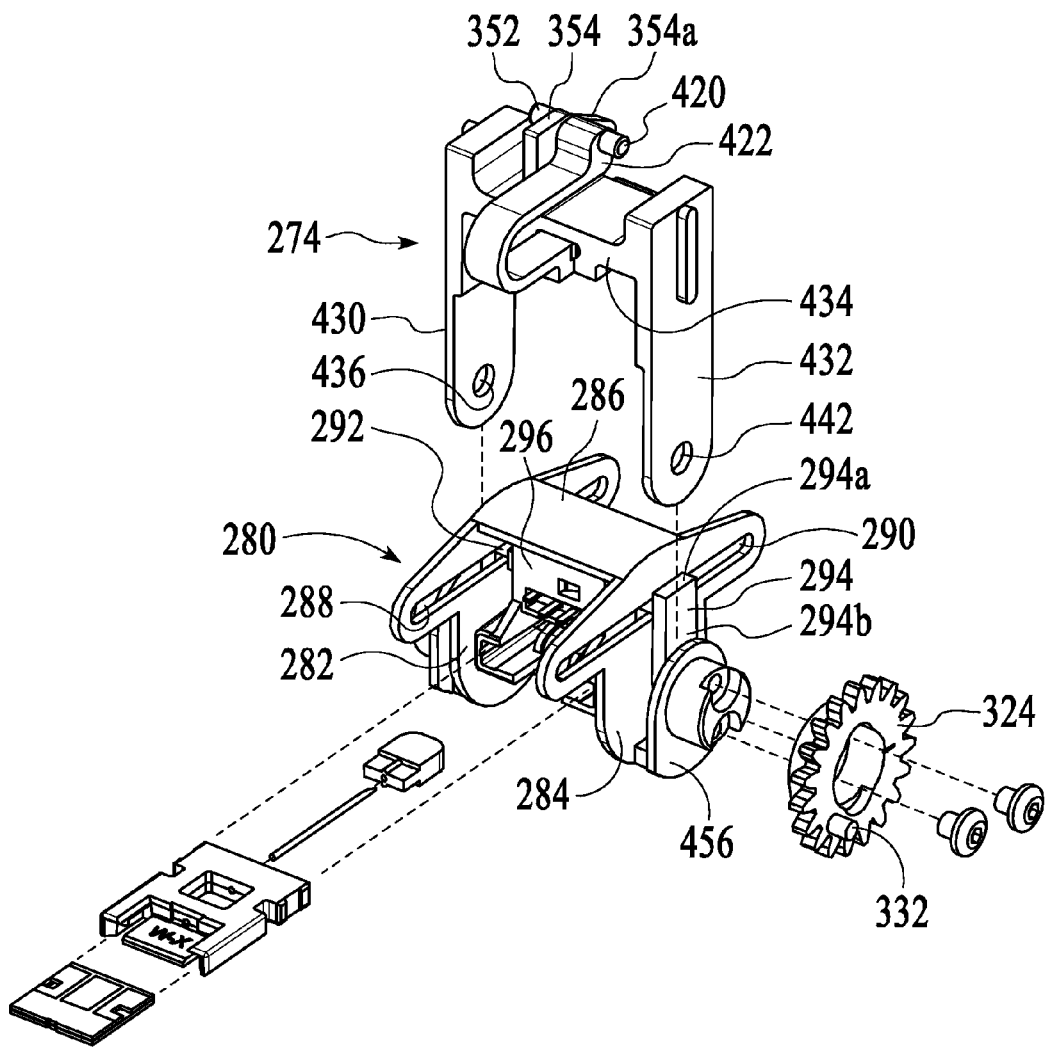
FIG. 20 is an exploded perspective view of selected components of a lancing/collecting assembly of a medical diagnostic apparatus of an alternative embodiment.
Figure 21:
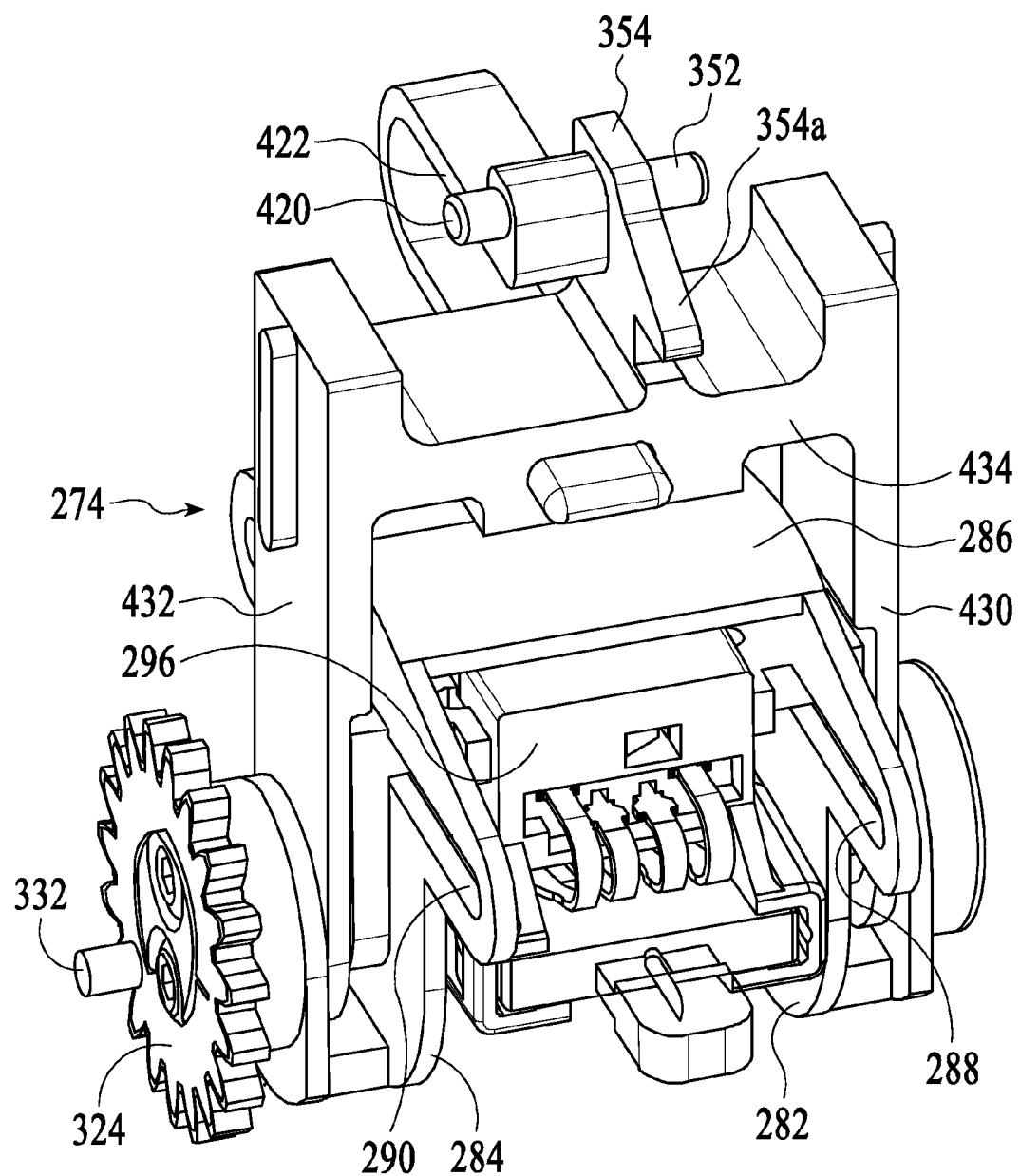
FIG. 21 is another perspective view of selected components of a lancing/collecting assembly of a medical diagnostic apparatus of an alternative embodiment. This view shows a side of the assembly not shown in FIG. 19.
Figure 22:
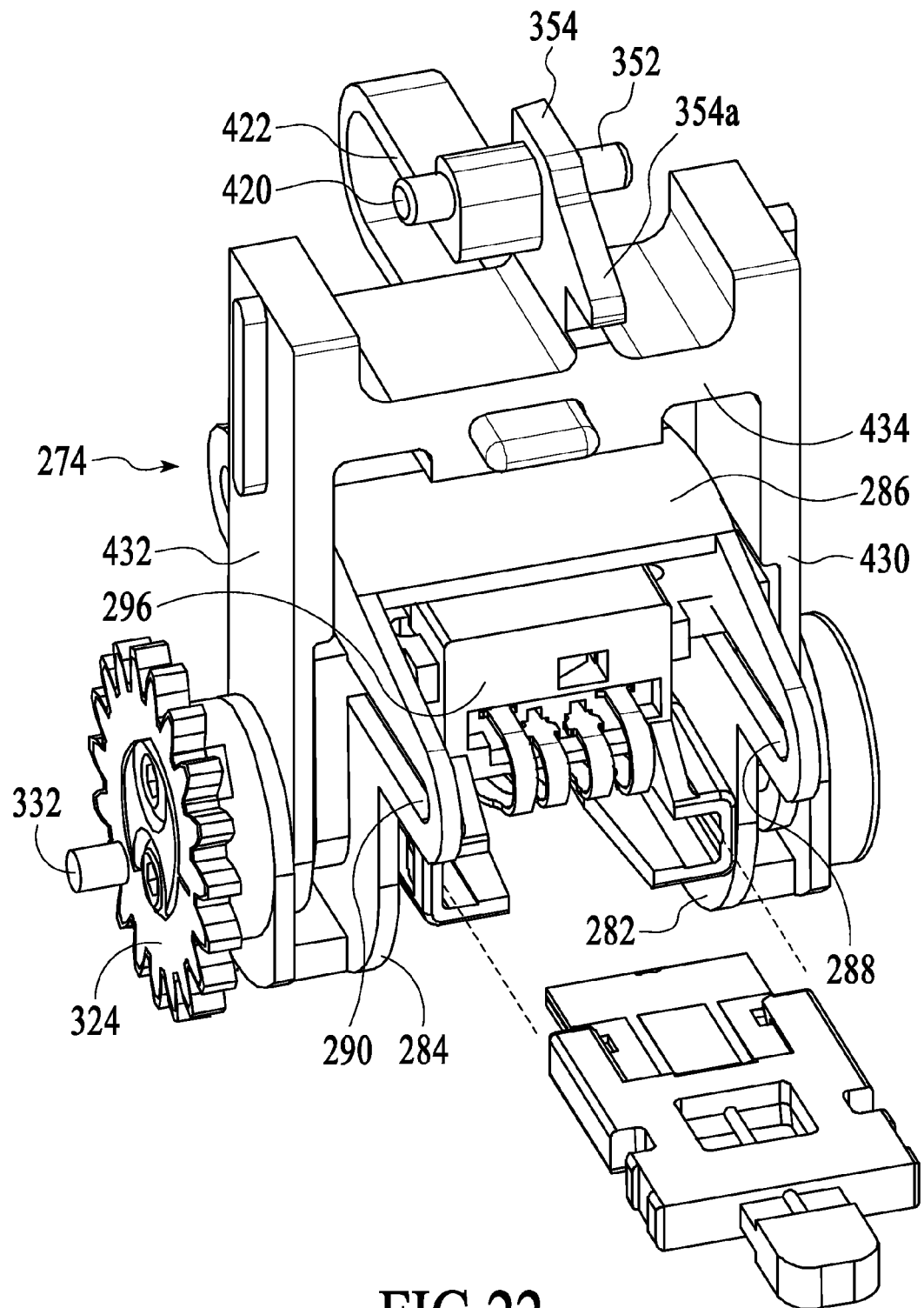
FIG. 22 is another perspective view of selected components of a lancing/collecting assembly of a medical diagnostic apparatus of an alternative embodiment. This view shows a side of the assembly not shown in FIG. 19.

As shown in FIG. 17, the projection 422 on the cam follower 274 is flexible and the projection 354 on the cam follower 274 is rigid. The flexible projection 422 is in the shape of the letter U. However, such a shape is merely a matter of choice and other shapes can be selected. For example, the projecting element can be diamond-shaped. The flexibility of the projection 422 enables the test strip to comply with the opening formed in the skin of the patient to facilitate collection of the sample of biological liquid. The rigid projection 354 is adjacent to the flexible projection 422. The lack of flexibility of the projection 354 enables the motion of the lancet of the lancet-containing portion of the test strip to be fixed, thereby allowing uniform puncturing of the skin of the patient during the lancing step. A nose portion 354a projecting from the projection 354 receives one end of the resilient biasing element 372, which locks the lancing cam 338 and the index cam 328 when these cams are not in operation.

The medical diagnostic device 100 can also include a mechanism for ejecting used test strips from the cradle 280. This mechanism can be operated by employing a user-actuated pushing assembly or a motor-actuated pushing assembly to push a used test strip out of the cradle 280 and out of the ejection port 230 of the housing 102.

To operate the lancing/collecting assembly, a motor can be used to apply a rotating drive input. Alternatively, any rotating drive source could be used, e.g., manual input by the user.

The lancing/collecting assembly 112 can be armed by actuating a slide 460 positioned in a slot in a side of the housing 102. The slide 460 is connected to the lancing rack 400 by means of a connector. In order to arm the lancet of the lancet-containing portion of the lancing/collecting assembly, the user need only move the slide 460 in the appropriate direction until the locking tab 404 on the trigger 406 abuts the locking tab 402 on the lancing cam 338. In an alternative embodiment, the slide 460 can be replaced by a motor capable of driving the lancing rack 400 in the appropriate direction.

Figure 24:
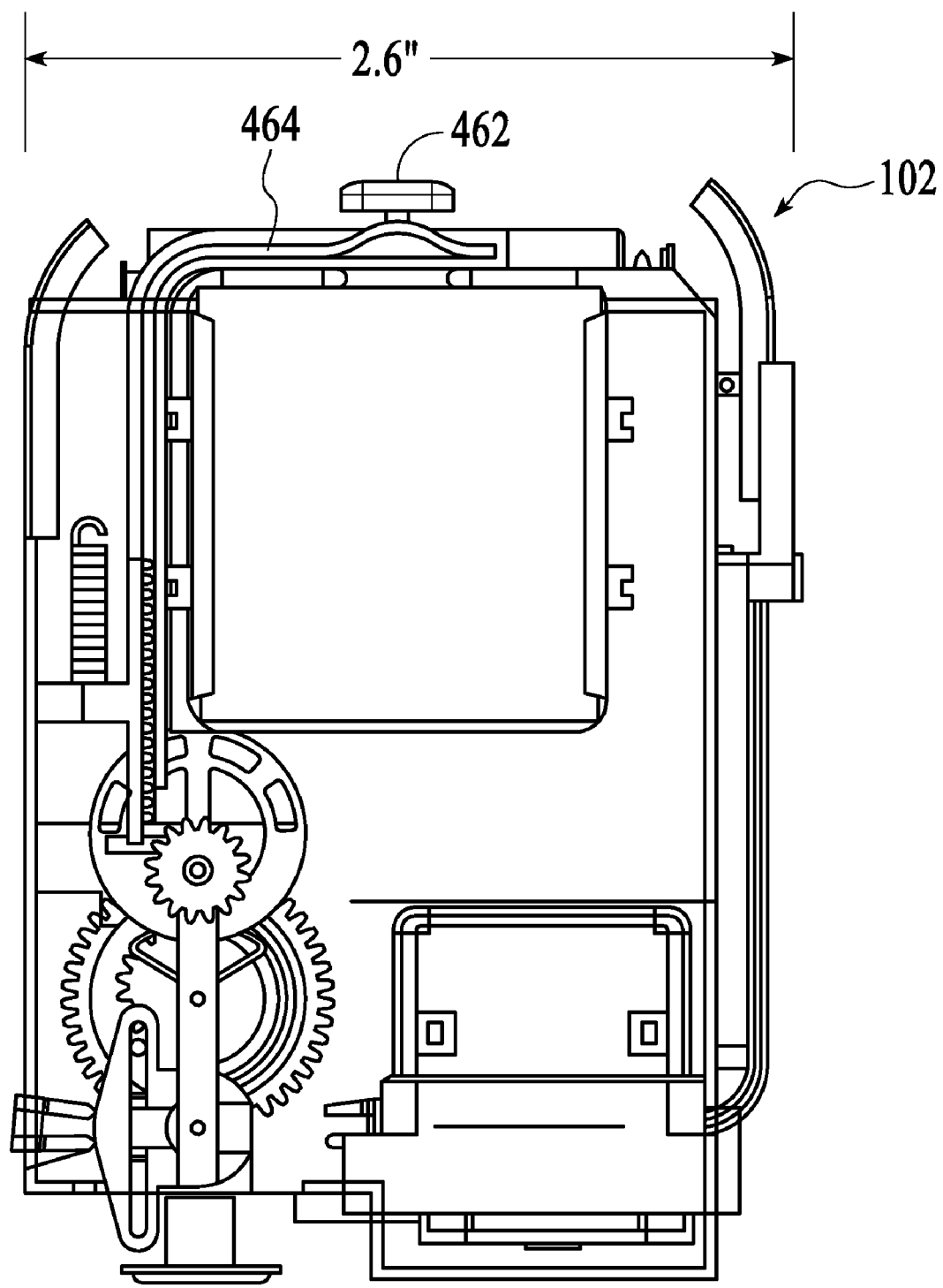
FIG. 24 is side view in elevation of a medical diagnostic apparatus of an alternative embodiment showing the position of a push-button suitable for triggering the lancing step of the method of an alternative embodiment.
Figure 25B:
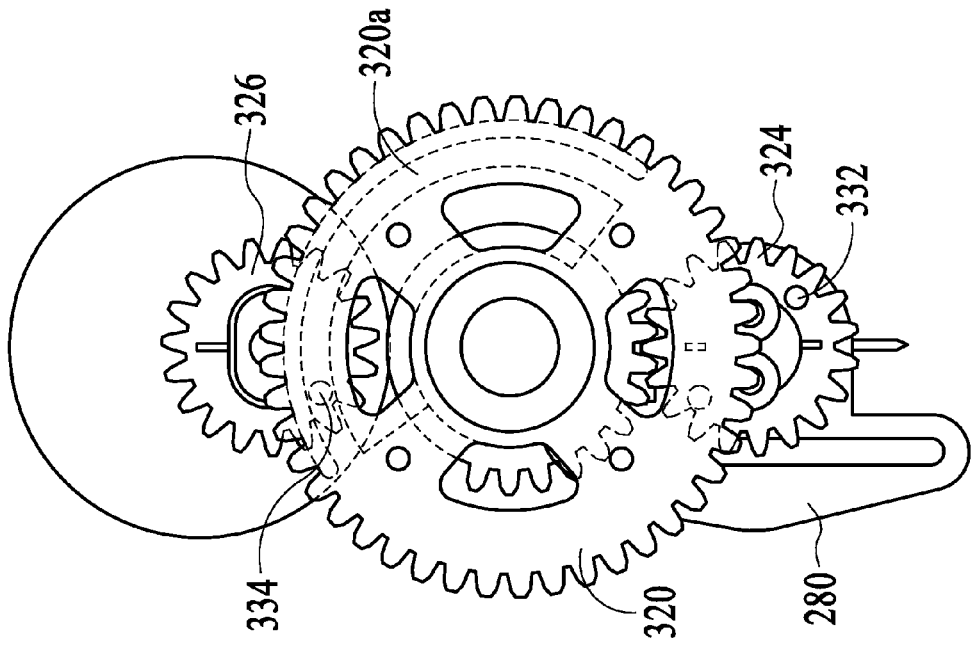
FIGS. 25A-25J, inclusive, are side elevational views illustrating positions of certain gears of a lancing/collecting assembly of a medical diagnostic apparatus of an alternative embodiment during one cycle of operation of the lancing/collecting assembly of the medical diagnostic device of an alternative embodiment.
Figure 25A:
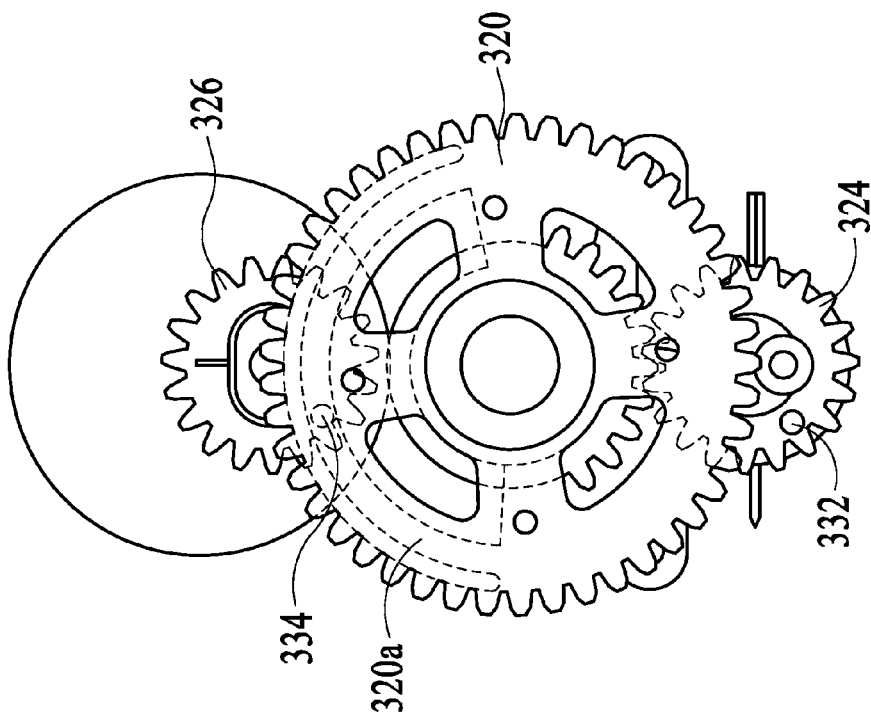
Figure 25C:
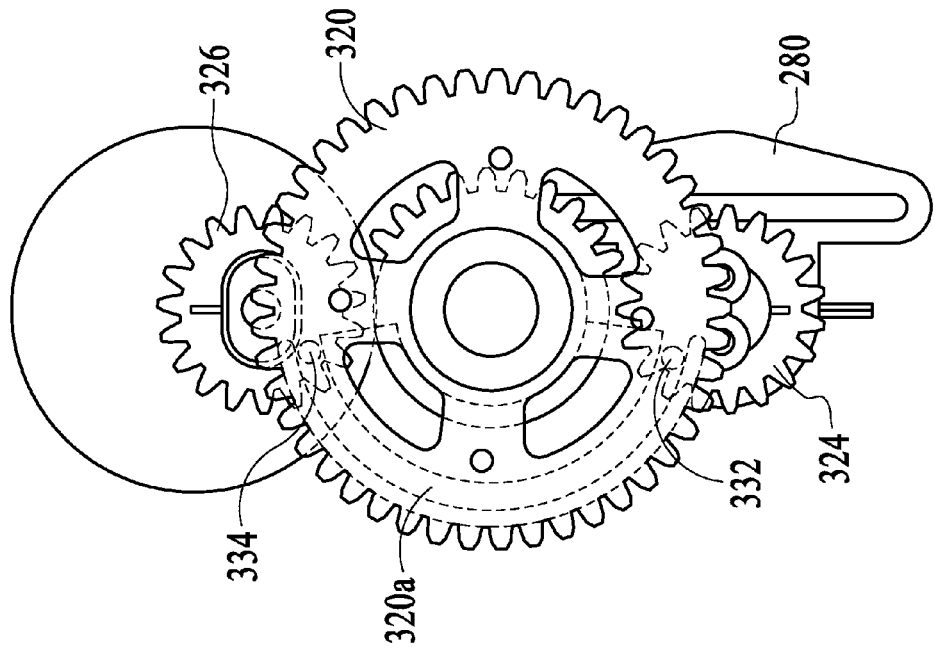
Figure 25D:
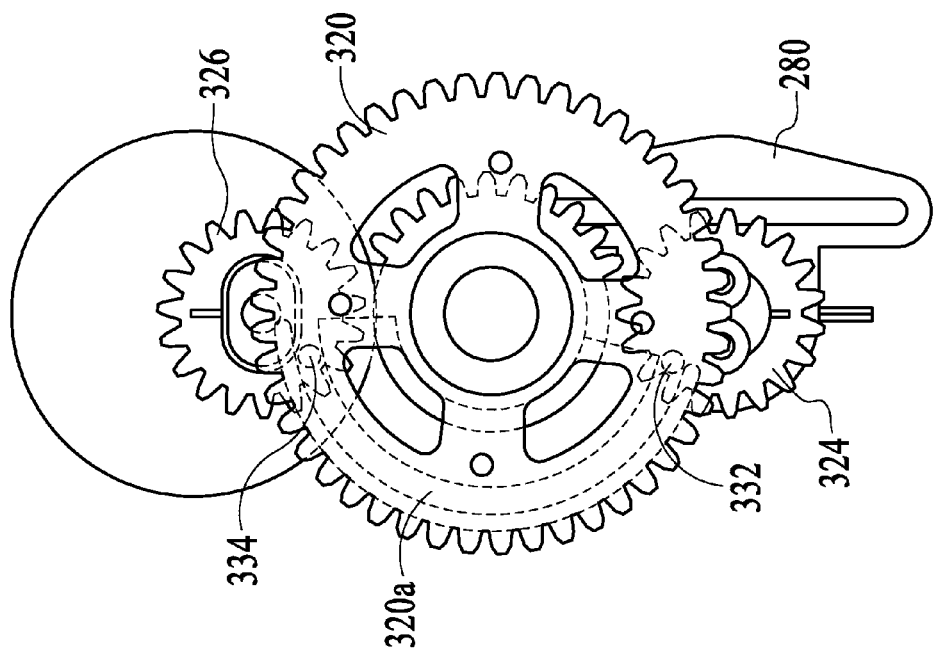
Figure 25F:
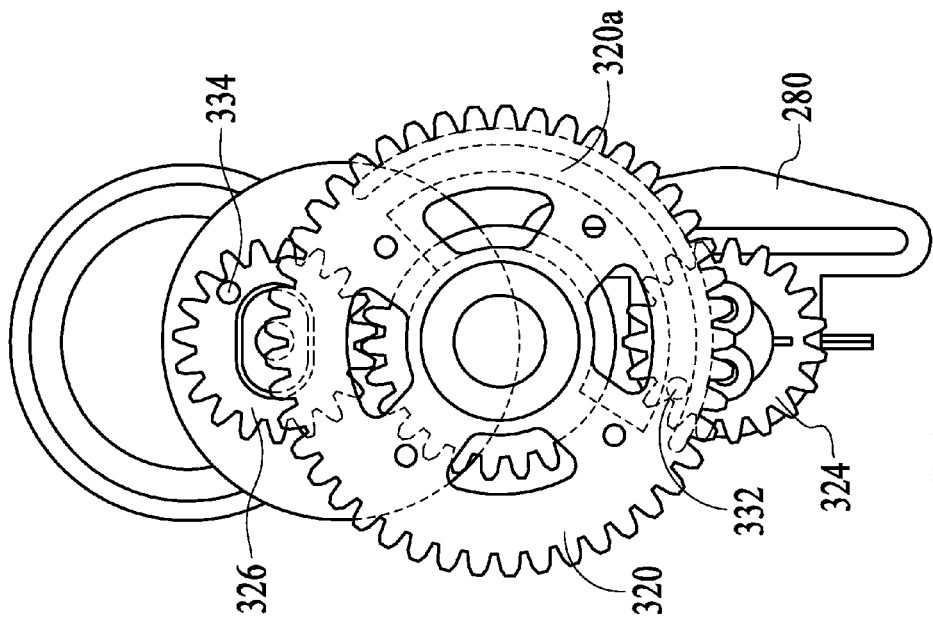
Figure 25E:
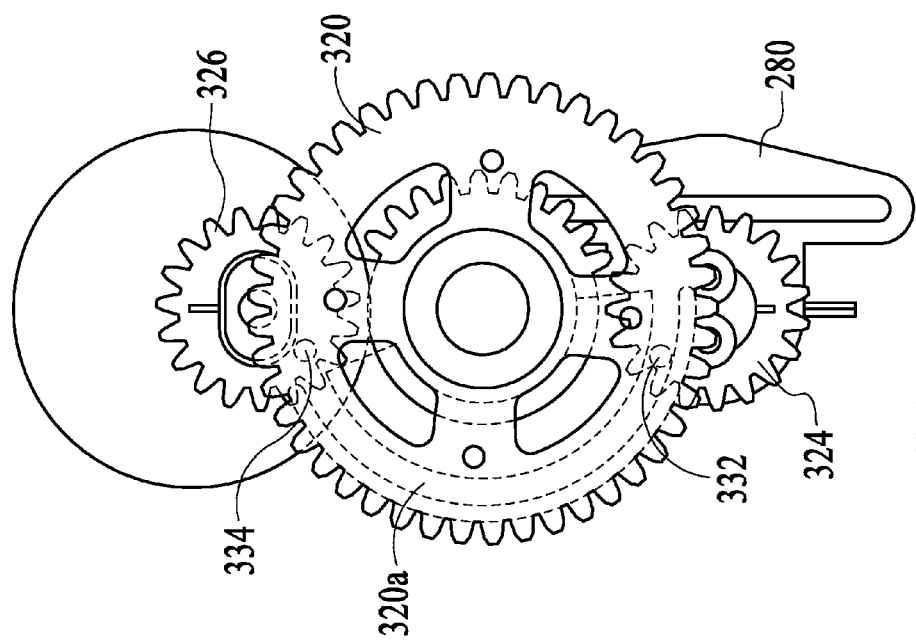
Figure 25H:
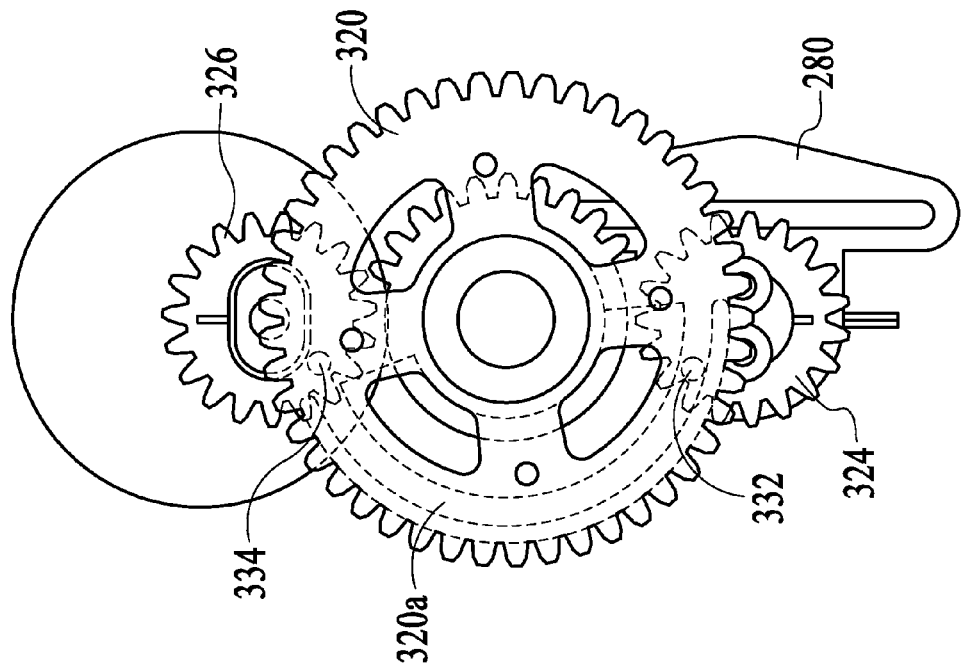
Figure 25G:
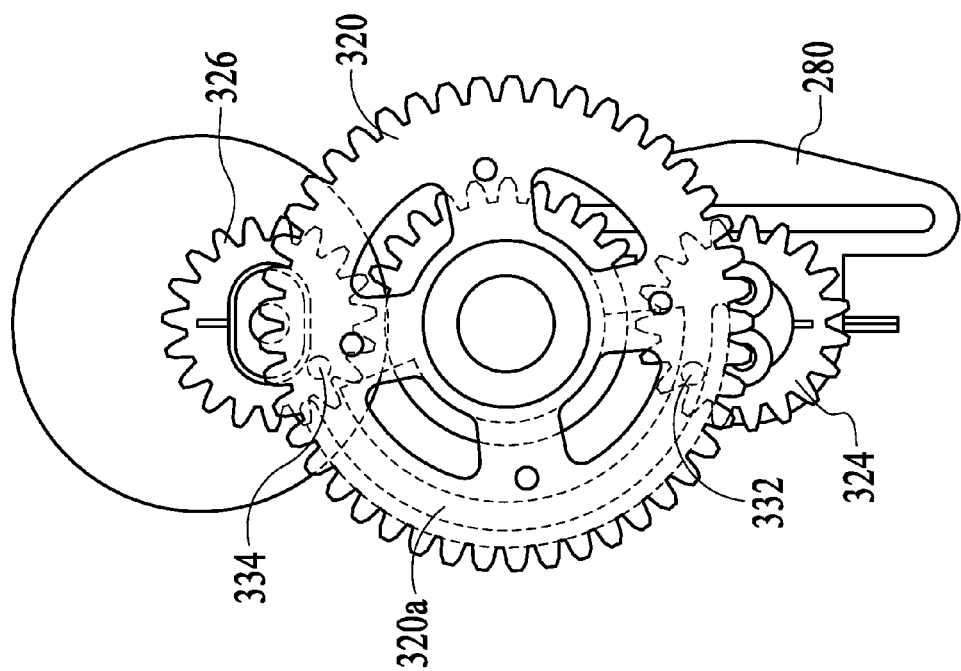
Figure 25J:
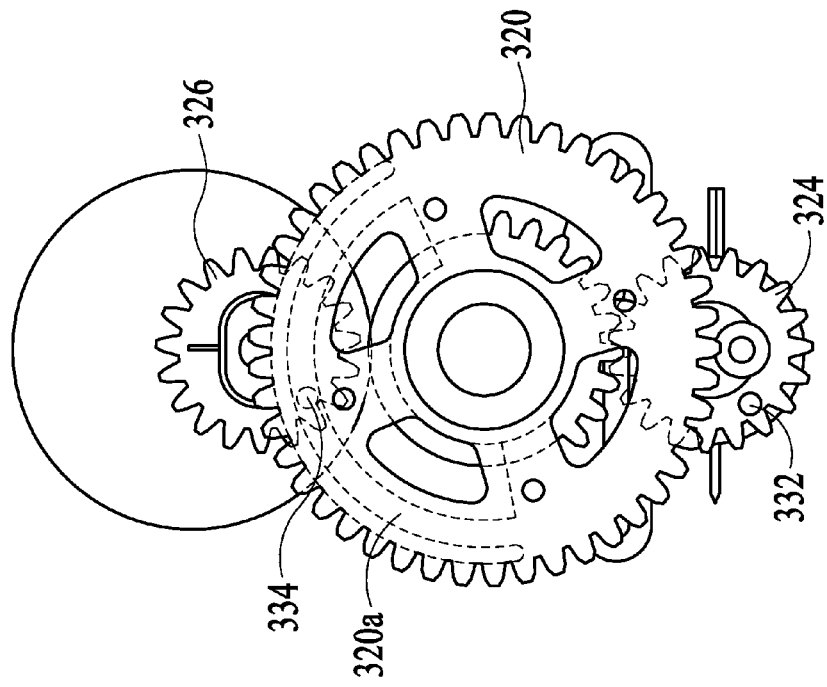
Figure 25I:
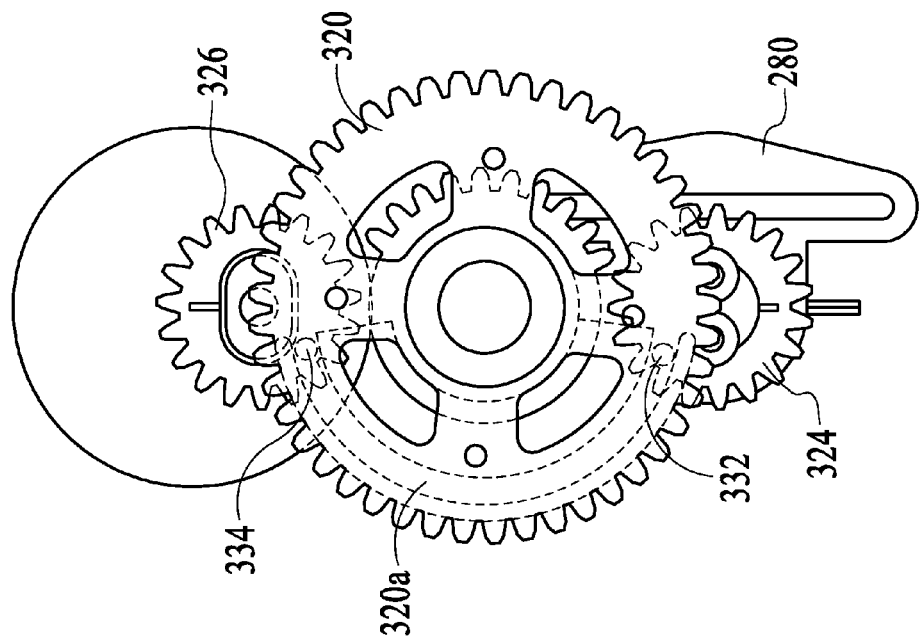

The trigger 406 of the lancing/collecting assembly 112 can be actuated by a push-button 462 positioned at the proximal end of an elongated element 464 that carries the locking tab 404, as shown in FIG. 24.

Test Strips

Figure 26A:
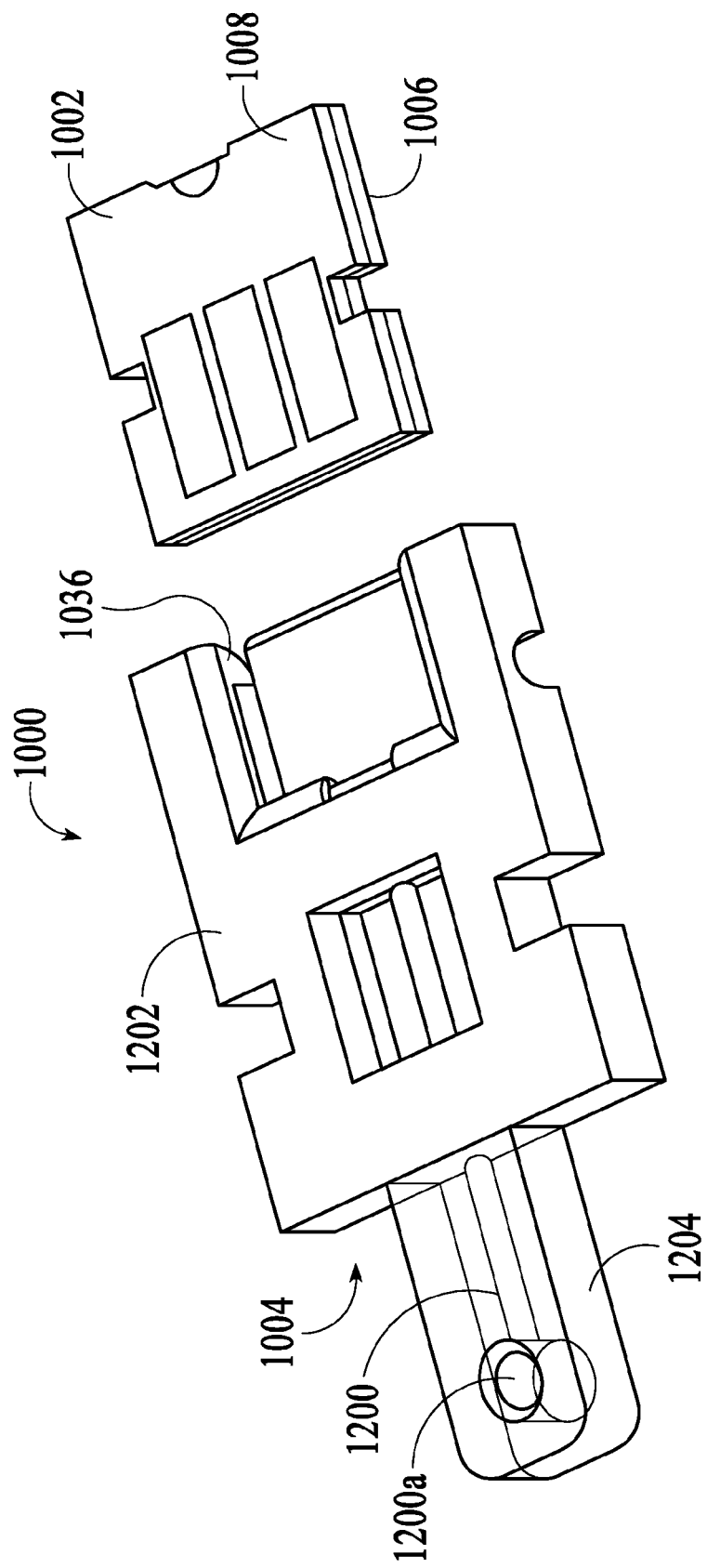
FIG. 26A is an exploded perspective view of one embodiment of the test strip of an embodiment, showing the lancet bearing a removable protective cover.
Figure 26B:
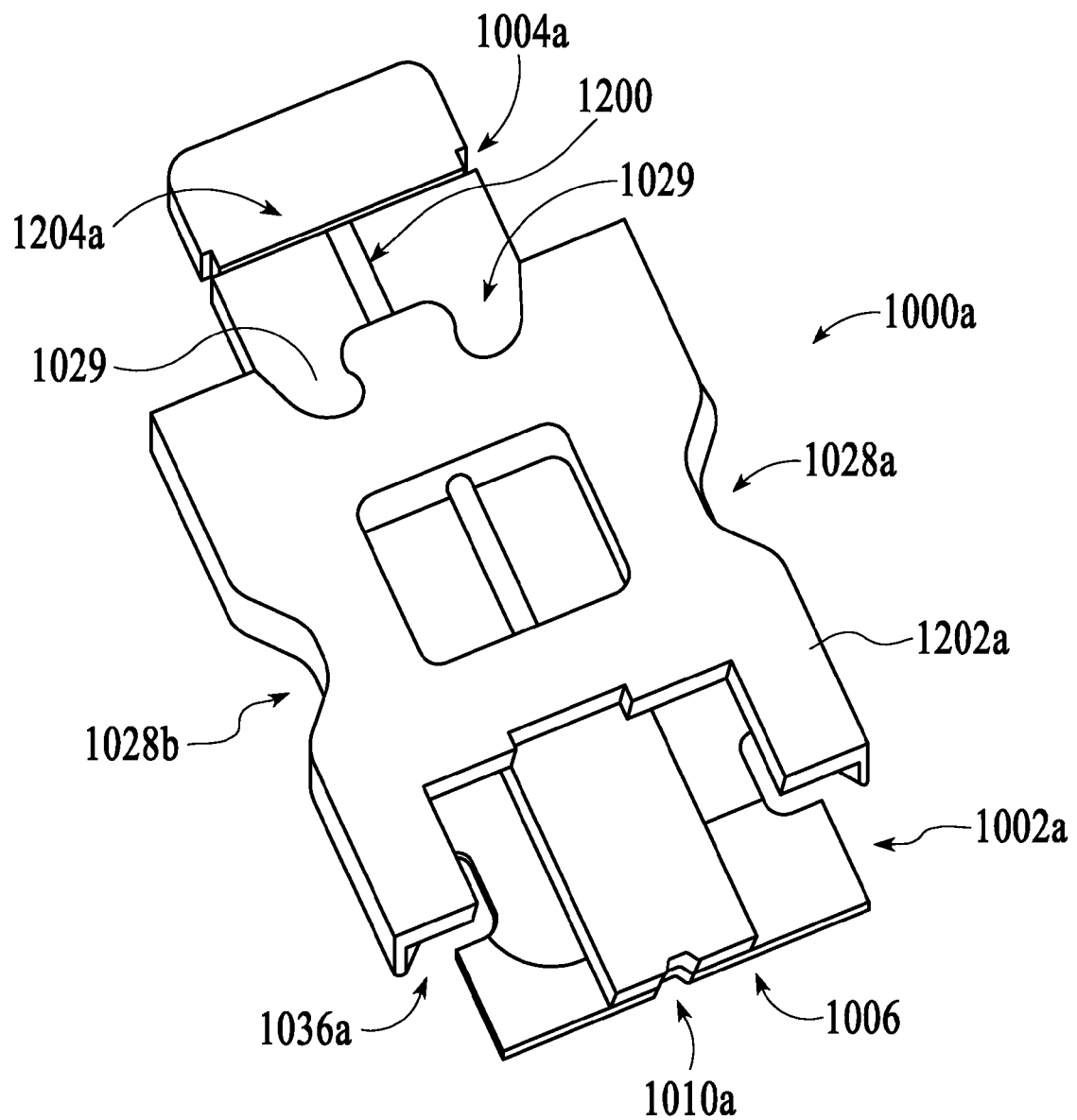
FIG. 26B is a perspective view of a testing striplet in accordance with an embodiment.

In order to make effective use of the medical diagnostic device, a novel test strip was developed. As shown in FIGS. 26A-26B, test strip 1000, 1000a suitable for use in accordance with an embodiment has a sensor-containing portion 1002, 1002a and a lancet-containing portion 1004, 1004a. Referring specifically to FIGS. 26A-26B, an integrated lancet and testing striplet 1000, 1000a is provided for measuring a body analyte, e.g., glucose, level in a diabetes care regimen. A lancet body 1202, 1202a includes a test strip receiving end 1036, 1036a and a lancet end. A lancet 1200 is coupled with and protruding from the lancet end and secured by a lancet cap 1204, 1204*a*. A test strip 1002, 1002*a* is coupled to the test strip receiving end 1036, 1036*a* of the lancet body 1202, 1202*a* having multiple electrodes and assay chemistry for testing an analyte, e.g., glucose, level of an applied body fluid. The test strip 1002, 1002*a* and lancet 1200 are relatively disposed at different ends of the striplet 1000, 1000*a* for providing both lancing and application of body fluid at a lancing site by reorienting and advancing the striplet 1000, 1000*a* within the meter after lancing to contact a sample receiving portion of the test strip precisely at the lancing site.

The reorienting may include rotating the striplet 1000, 1000*a* when the lancing site remains approximately at the predetermined location relative to the meter for application of body fluid to the sample receiving portion of the test strip 1002, 1002*a*. The test strip 1002, 1002*a* and lancet 1200 may be symmetrically disposed at opposite ends of the lancet body 1202, 1202*a*. The reorienting may include rotating and/or flipping the striplet 1000, 1000*a* when the lancing site remains approximately at the predetermined location relative to the meter for application of body fluid to the sample receiving portion 1010*a* of the test strip 1002, 1002*a*.

The lancet body 1202, 1202*a* may include a pair of relatively disposed recesses 1028*a*, 1028*b* for respectively positioning the test strip via a spring-loaded ball and detent mechanism (not shown) for lancing and application of body fluid at a same lancing/testing site. The recesses 1028*a*, 1028*b* may be trapezoidally-shaped, as in FIG. 26B.

The lancet cap 1204*a* of FIG. 26B includes two elastomeric arms 1029, although there may be one or more than two, that couple with defined cutouts in the lancet body 1202*a* for snapping the cap 1204*a* into and out of mating relationship with the lancet body 1202*a* by respective application of sufficient coupling and separation force.

Figure 26C:
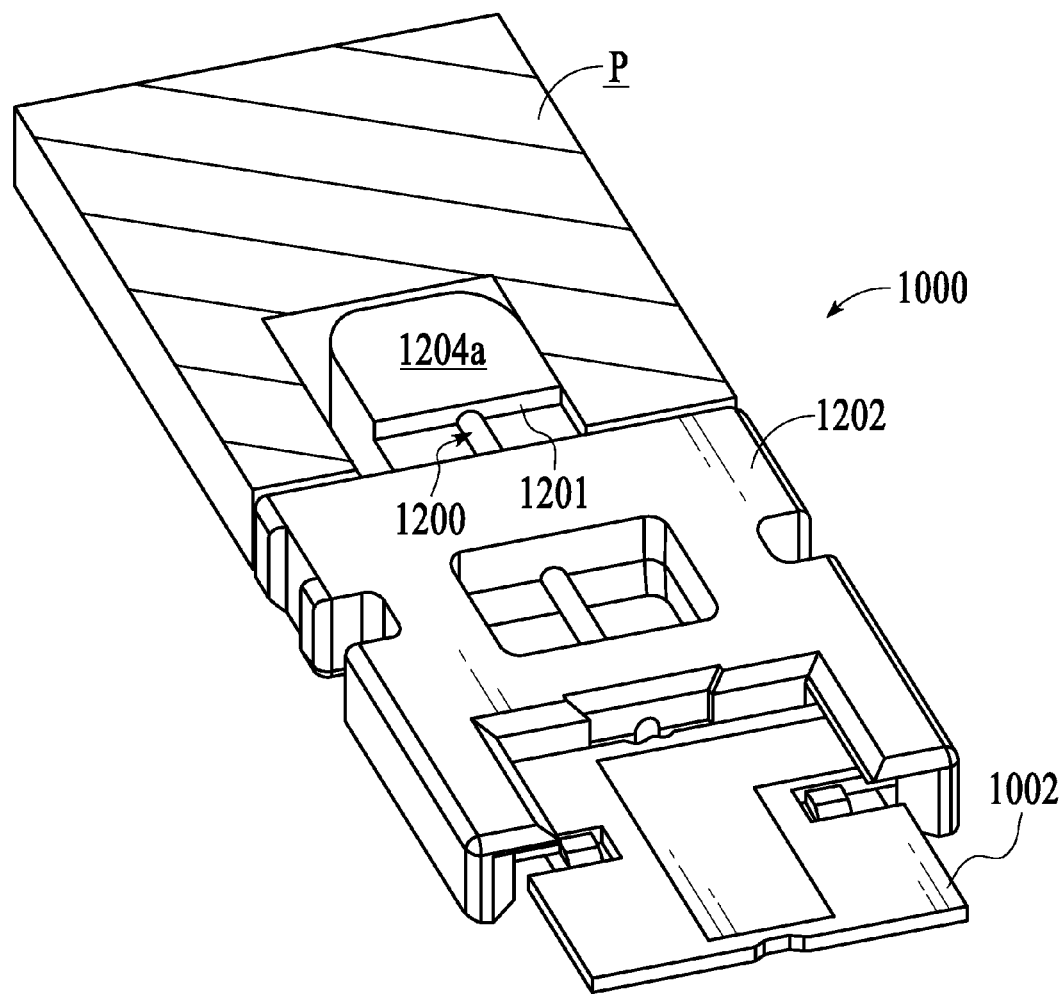
FIG. 26C is a perspective view of a testing striplet coupled with a pusher P which serves both to advance the striplet and in combination with a blade B in one embodiment also serves to arm the lancet by removing lancet cap in a retreating motion of the coupled-together blade B, cap and pusher P.
Figure 27:
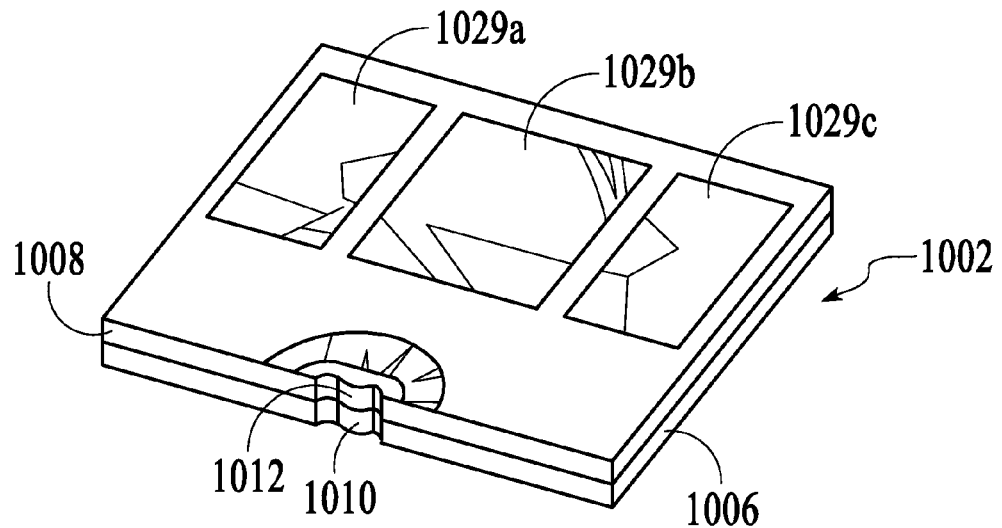
FIG. 27 is a perspective view of the sensor-containing portion of the embodiment of the test strip shown in FIG. 26.

Referring for a moment to FIG. 26C, a striplet 1000 is shown including a lancet body 1202, test strip 1002 coupled with the lancet body 1202, and a lancet cap 1204*a* protecting a lancet 1200 which is also coupled to the lancet body 1202. The pusher P of FIGS. 7A-7P is shown coupled with the striplet 1000. The pusher P has a U-shape in FIG. 26C, and may have any of a variety of shapes that fit somewhat snugly such as to overlap the lancet cap 1204*a* at least through the plane of a mating contour 1201 of the lancet cap 1204*a*. Although not shown in FIG. 26C, the pusher may have a corresponding contour to the mating contour 1201 of the lancet cap 1204*a*. When the blade B of FIGS. 7A-7P is disposed in mating relation with the mating contour 1201 of the lancet cap 1204*a*, the pusher P is also coupled, via its own corresponding contour or sufficient friction, with the blade B and/or with the lancet cap 1204*a*. This permits a retreating motion of the pusher P to bring the lancet cap 1204*a* with it away from the lancet body 1202 of the striplet 1000 for arming the lancet 1200 while the striplet 1000 is disposed in the turret 225 shown in FIGS. 7A-7P. Although not shown, a chain or other flexible component may be attached to the pusher P for advancing and retreating the pusher P, e.g., as illustrated in one example at FIG. 6F.

Figure 31:
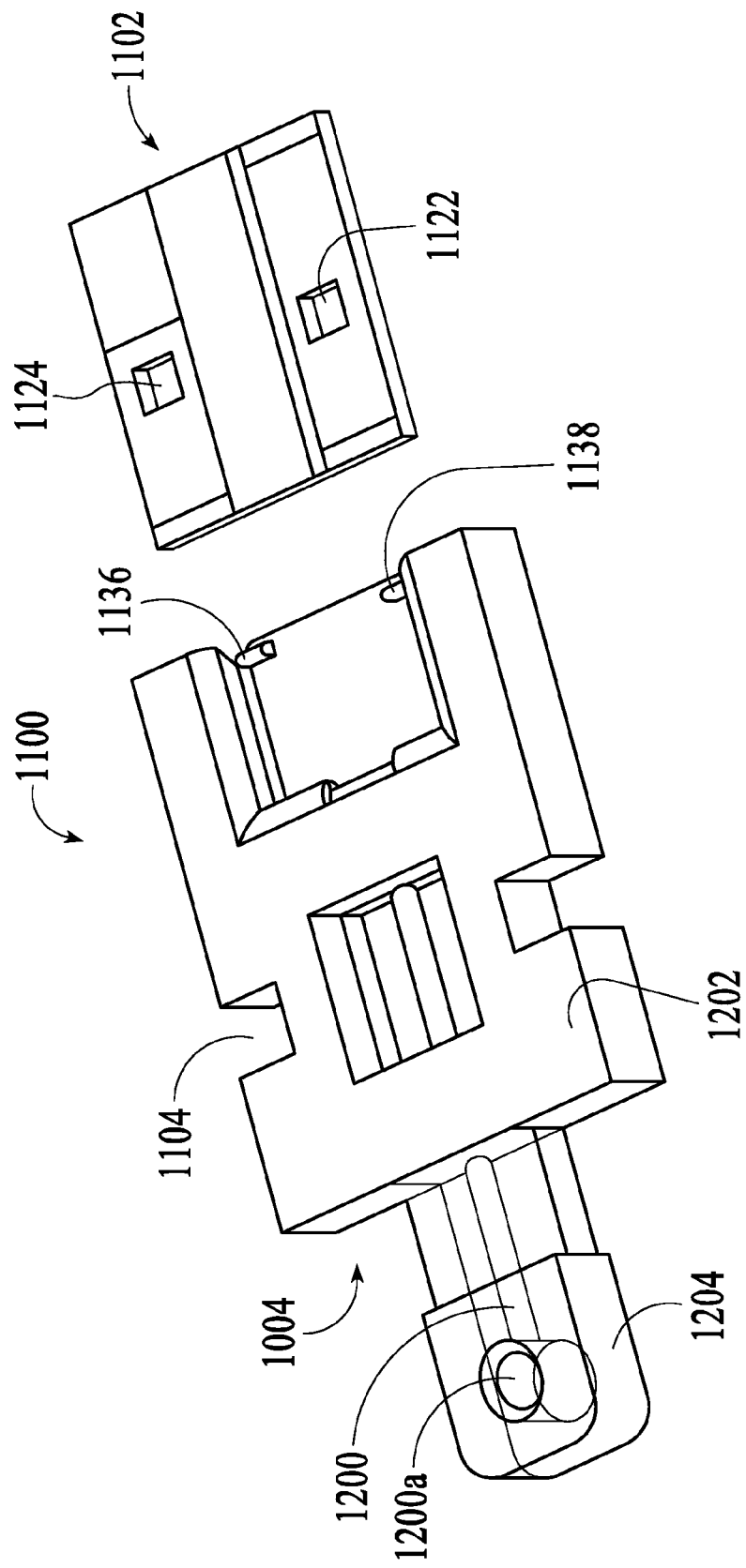
FIG. 31 is an exploded perspective view of still another embodiment of the test strip of an alternative embodiment, showing the lancet bearing a removable protective cover.

The lancet body 1202, 1202*a* and test strip 1002, 1002*a* of FIGS. 26A, 26B or see specifically FIG. 31, may include at least two teeth 1136, 1138 that fit corresponding slots 1122, 1124 for coupling the lancet body 1202, 1202*a* and test strip 1002, 1002*a*, 1102 together, and the lancet body 1202, 1202*a* has the teeth and the test strip 1002, 1002*a*, 1102 has the corresponding slots 1122, 1124.

Figure 28:
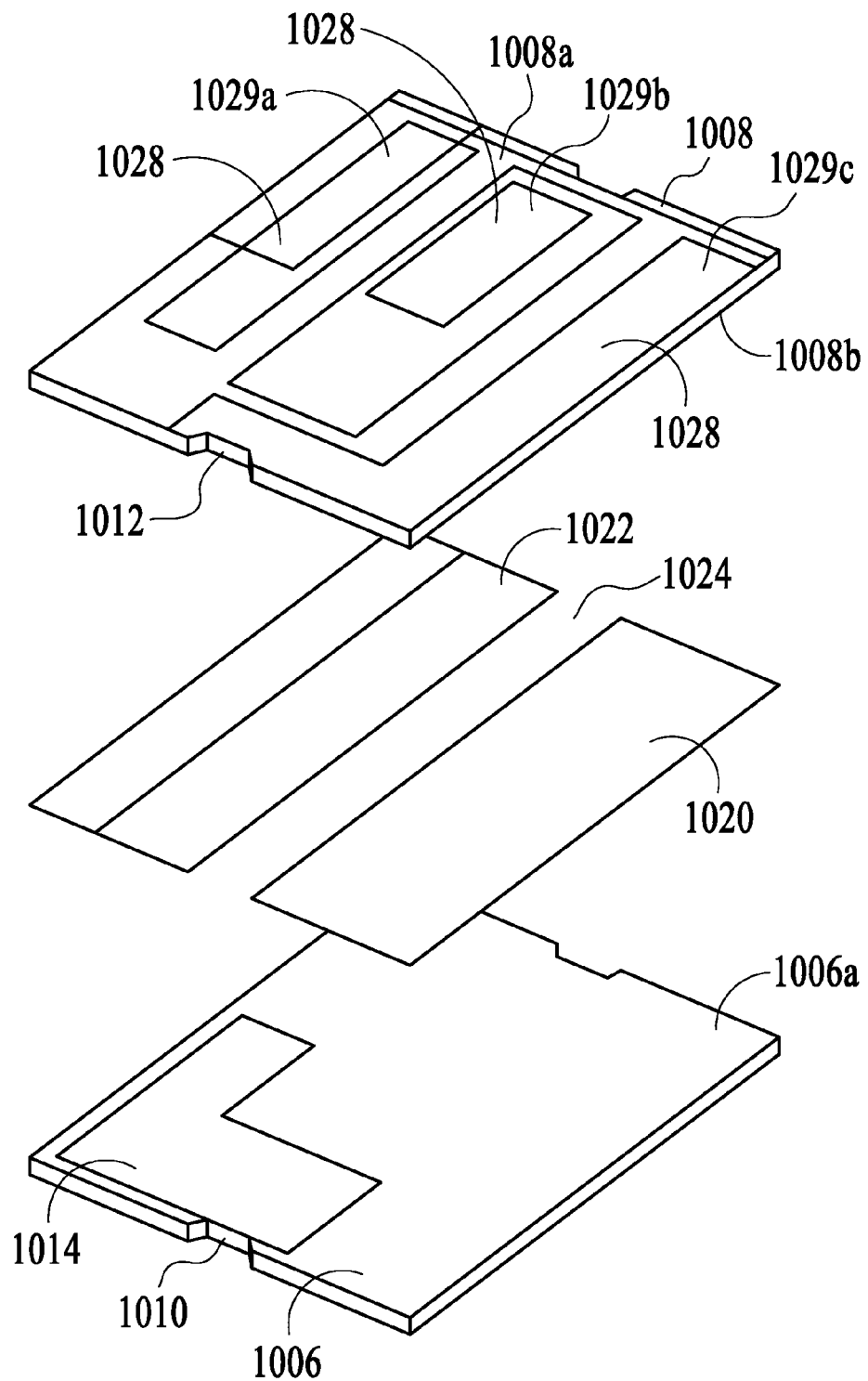
FIG. 28 is an exploded perspective view of the sensor-containing portion of the test strip shown in FIG. 27. In this view, the recesses for tabs of the lancet-containing portion of the test strip are not shown.

The test strip 1002, 1002*a*, 1102 may include a base 1006 and a cover 1008 as illustrated at FIG. 28. The base 1006 may have a layer of electrically conductive material applied to one major surface thereof 1006*a*, while the cover 1008 may have a working electrode and a trigger electrode applied to one major surface 1008*b* thereof. The base 1006 may be adhered to the cover 1008 by a layer of electrically conductive adhesive and/or a layer of non-conductive adhesive 1020, 1026.

The sensor-containing portion may include a sample flow channel, and a working electrode and a trigger electrode may be positioned in the flow channel.

The cover 1008 may include at least one electrical passageway running from an inner face to an outer face and/or a slot formed therein to attach the sensor-containing portion to a tab in the lancet-containing body.

The base may include an opening formed therein to attach the sensor-containing portion to a tab in the lancet-containing body.

The base 1006 or the cover 1008 has a recess 1010, 1010*a*, 1012 formed in an edge thereof that forms the sample receiving portion of the test strip. The recess 1010, 1010*a*, 1012 may have a hydrophilic material applied thereto. The lancet 1200 may be positioned approximately 180° from the recess 1010, 1010*a*, 1012. Electrical contact pads may be on one major surface of the cover 1006 and/or base 1008. The cover 1006 may include a layer of electrically conductive or semiconductive material, such as carbon. The trigger electrode may include carbon.

In one embodiment, the sensor-containing portion 1002 includes a base 1006 and a cover 1008. As shown in FIGS. 26-29B, inclusive, both the base 1006 and the cover 1008 are substantially rectangular in shape, although other shapes may be used. In this substantially rectangular embodiment, the base 1006 has two major surfaces 1006*a*, 1006*b* and four edges 1006*c*, 1006*d*, 1006*e*, and 1006*f* (see FIG. 28). The cover 1008 has two major surfaces 1008*a*, 1008*b* and four edges 1008*c*, 1008*d*, 1008*e*, and 1008*f*. The base 1006 has a recess 1010 formed in one edge thereof, and the cover 1008 has a recess 1012 formed in one edge thereof. The surfaces of these recesses 1010 and 1012 bear a hydrophilic material in order to enable the sample of biological liquid to have greater affinity for the recesses 1010 and 1012 than if the recesses were not bearing a hydrophilic material. The base 1006 and the cover 1008 may be made from an electrically non-conducting material, e.g., an insulating material that is not capable of carrying substantial electric charge or current. Examples of materials usable include polyesters, polyethylene (both high density and low density), polyethylene terephthalate, polycarbonate, vinyls, and the like. The material may be treated with a primer or other such coating to improve the adhesion of the electrodes thereon. In certain embodiments, the base and/or cover is made from a hydrophobic polymeric material, e.g., "MELINEX" polymer, or the like.

The base 1006 bears a layer of electrically conductive material 1014 on the major surface thereof facing the cover 1008. Conductive material that may be used include gold, carbon, platinum, ruthenium dioxide, palladium, and conductive epoxies, such as, for example, ECCOCOAT CT5079-3 Carbon-Filled Conductive Epoxy Coating (available from W. R. Grace Company, Woburn, Mass.), Ag/AgCl, Ag/AgBr, as well as other materials known to those skilled in the art. For example, the embodiment of FIG. 6A may include Ag/AgCl. This electrically conductive material functions as a dual-purpose reference/counter electrode. The major surface of the cover 1008 facing the base 1006 bears a layer of electrically conductive material 1016 in a first area, which layer of electrically conductive material constitutes a working electrode, and a layer of electrically conductive material 1018 in a second area, which layer of electrically conductive material constitutes a trigger electrode. The major surface of the cover 1008 facing the base 1006 also bears a layer of non-conductive adhesive 1020 in a first area and layer of non-conductive adhesive 1022 in a second area to bond the cover 1008 to the base 1006. The layers of non-conductive adhesive 1020, 1022 also function to space the cover 1008 from the base 1006 so that a channel 1024 running along the center of the sensor-containing portion 1002 of the test strip 1000 is formed. A layer of electrically conductive adhesive 1026 enables the transfer of signal from the major surface 1006*a* of the base 1006 to the major surface 1008*b* of the cover 1008. The layer of electrically conductive adhesive 1026 can be made from a pressure-sensitive adhesive doped with an electrically conductive material, e.g., carbon. The layer of electrically conductive adhesive 1026 may be any suitable thickness, e.g., 0.002 inch.

At least one electrical passageway 1028 enables the transfer of signal from the major surface 1008*b* of the cover 1008 to the major surface 1008*a* of the cover 1008. An electrical passageway is a passageway formed in the cover 1008. The at least one electrical passageway 1028 is filled with electrically conductive material, such as, for example, carbon. The benefit resulting from the use of one or more electrical passageways is that all of the contact pads 1029*a*, 1029*b*, 1029*c* of the sensor-containing portion 1002 of the test strip 1000 can be positioned on one major surface of the cover 1008 of the test strip 1000.

Figure 29A:
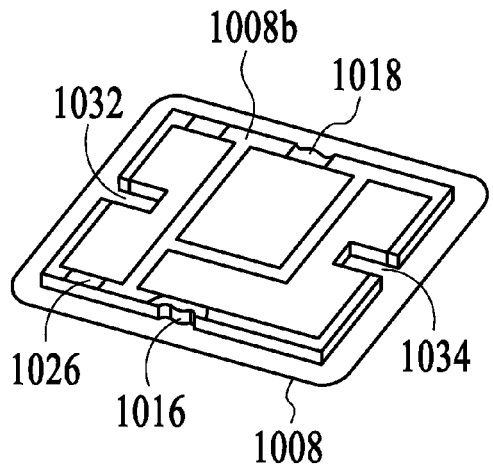
FIG. 29A is a perspective view of the inner face of the cover of the sensor-containing portion of the test strip shown in FIG. 26. In this embodiment, the recesses for tabs of the lancet-containing portion of the test strip are shown.
Figure 29B:
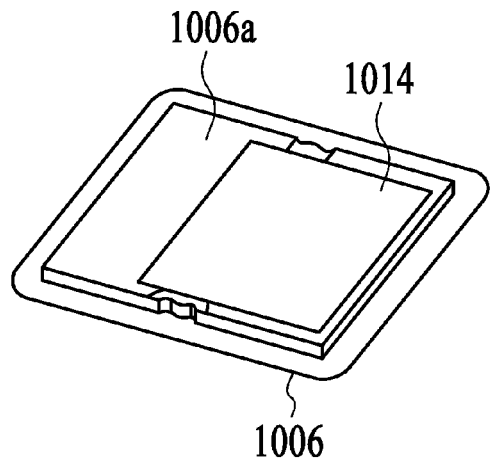
FIG. 29B is a perspective view of the inner face of the base of the sensor-containing portion of the test strip shown in FIG. 26.
Figure 29C:
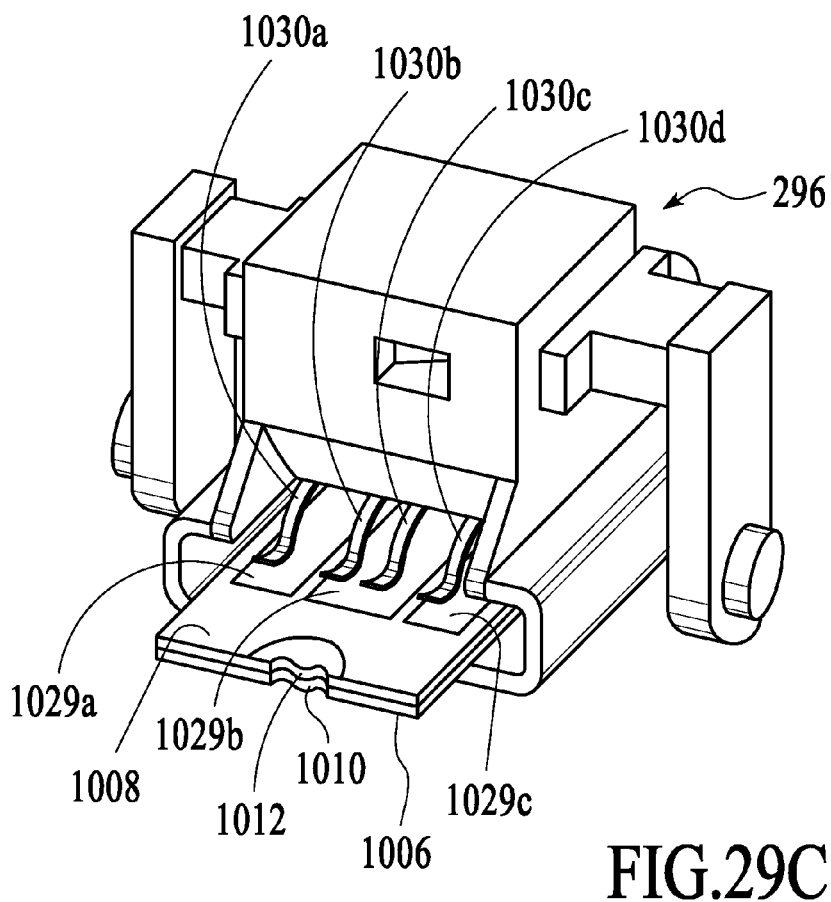
FIG. 29C is a perspective view of the test strip of FIG. 26 inserted into the analyzer of the medical diagnostic device of an alternative embodiment.

While not critical, it is advantageous that the dimensions of the sensor-containing portion 1002 of the test strip 1000 be as small as possible in order to reduce the size of the assembly 110 and reduce the volume of sample required to carry out a test. Typical dimensions of the base 1006 and cover 1008 are approximately 6 mm×6 mm×<2 mm. Typical dimensions of the electrodes and typical dimensions of a sample flow channel 1024 are described in U.S. Pat. Nos. 6,229,757 and 6,616,819, incorporated herein by reference. When the sample of biological liquid is introduced at the hydrophilic recesses 1010, 1012, the liquid is easily drawn up into the channel 1024, along which the liquid flows by means of capillary attraction. The major surface 1008*a* of the cover 1008 not facing the base 1006 has electrical contact pads 1029*a*, 1029*b*, 1029*c* exposed, which electrical contact pads 1029*a*, 1029*b*, 1029*c* are in contact with the contact leads 1030*a*, 1030*b*, 1030*c*, 1030*d* of the carrier 296, as shown in FIG. 29C. The cover 1008 also has two recesses 1032, 1034 in the edges perpendicular to the edge having the sample uptake recess 1012. The function of these recesses 1032, 1034 in the sides is to securely attach the sensor-containing portion 1002 of the test strip 1000 to the lancet-containing portion 1004 of the test strip 1000, which holds the lancet in place. As shown in FIG. 26, the tabs 1036 and 1038 project downwardly from the lancet-containing portion 1004 of the test strip 1000 toward the recesses 1032, 1034 in the edges of the sensor-containing portion 1002 of the test strip 1000.

A meter or other electrical device may use an electrical connector, which is configured to couple with and contact the contact pads at the end of a sensor. The meter may include a potentiostat or other component to provide a potential and/or current for the electrodes of the sensor. If configured for optical analysis, at least one light source may be provided, including componentry for measuring a property of the light as it impinges the sample, e.g., reflectance, absorbance, etc. The meter also typically includes a processor (e.g., a microprocessor or hardware) for determining the concentration of an analyte from the signals from the sensor. The meter also includes a display or port for coupling a display to the sensor. The display displays the signals from the sensor and/or results determined for the signals from the sensor including, for example, the concentration of an analyte, and/or the exceeding of a threshold of the concentration of an analyte (including, for example, hypo- or hyperglycemia). Furthermore, the meter may be configured to indicate to the user, via, for example, an audible, visual, or other sensory-stimulating alarm, when the level of the analyte is at or near a threshold level. For example, an alarm system may be included. For example, if glucose, is monitored then an alarm may be used to alert the user to a hypoglycemic or hyperglycemic glucose level and/or to impending hypoglycemia or hyperglycemia. The electrical connector employs contact leads that provide electrical connection between the sensor and the meter. The leads have proximal ends to physically contact the contact pads and distal ends to connect to any attached meter. The end of the sensor that has the contact pads can be slid into or mated with the electrical connector by placing the sensor into a slide area, which provides a support for and retains the sensor. It is important that the contact leads of the electrical connector make electrical contact with the correct pads of the sensor so that the working electrode and counter electrode(s) are correctly coupled to the meter. In certain embodiment of the medical diagnostic device 100 described herein, the carrier 296 substantially performs the aforementioned functions of the meter that is described in U.S. Pat. No. 6,616,819.

Figure 30A:
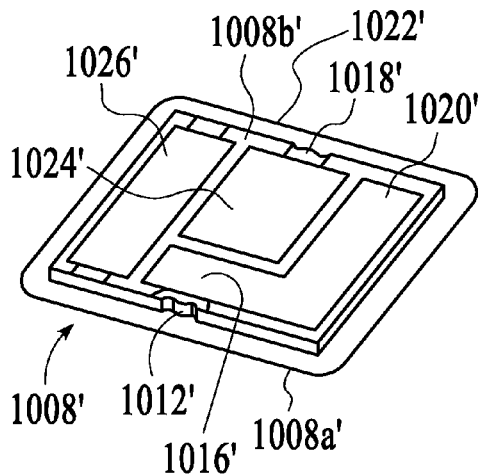
FIG. 30A is a perspective view of the inner face of the cover of another embodiment of the sensor-containing portion of the test strip of an alternative embodiment.
Figure 30B:
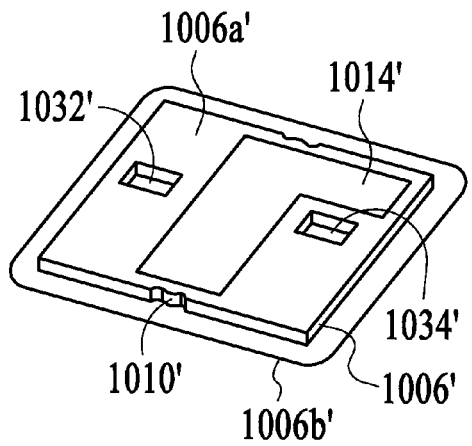
FIG. 30B is a perspective view of the inner face of the base of the sensor-containing portion of the test strip shown in FIG. 30A. In this embodiment, the openings for tabs of the lancet-containing portion of the test strip are shown.
Figure 30C:
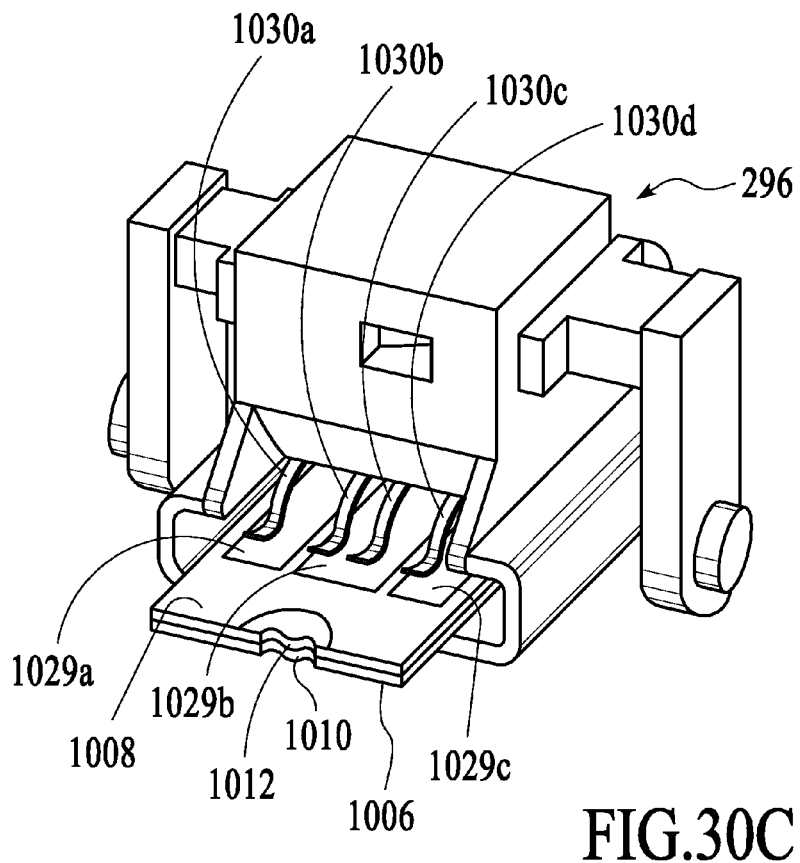
FIG. 30C is a perspective view of the test strip made from the base shown in FIG. 30A and the cover shown in FIG. 30B inserted into the analyzer of the medical diagnostic device of an alternative embodiment.

In another embodiment, the sensor-containing portion 1002' includes a base 1006' and a cover 1008'. As shown in FIGS. 30A-30C, inclusive, both the base 1006' and the cover 1008' are substantially rectangular in shape, but other shapes may be employed. In this embodiment, the base 1006' has two major surfaces 1006*a'*, 1006*b'* and four edges 1006*c'*, 1006*d'*, 1006*e'*, and 1006*f'*. The cover 1008' in this embodiment has two major surfaces 1008*a'*, 1008*b'* and four edges 1008*c'*, 1008*d'*, 1008*e'*, and 1008*f'*. The base 1006' has a recess 1010' formed in one edge thereof, and the cover 1008' has a recess 1012' formed in one edge thereof. The surfaces of these recesses 1010' and 1012' bear a hydrophilic material in order to enable the sample of biological liquid to have greater affinity for the recesses 1010', 1012' than if the recesses were not bearing a hydrophilic material.

The base 1006' bears a layer of electrically conductive material 1014' (for example, Ag/AgCl) on the major surface thereof facing the cover layer 1008'. This electrically conductive material functions as a dual purpose reference/counter electrode. The major surface of the cover 1008' facing the base 1006' bears a layer of electrically conductive material 1016' in a first area, which layer of electrically conductive material constitutes a working electrode, and a layer of electrically conductive material 1018' in a second area, which layer of electrically conductive material constitutes a trigger electrode. The major surface of the cover 1008' facing the base 1006' also bears a layer of non-conductive adhesive 1020' in a first area and layer of non-conductive adhesive 1022' in a second area to bond the cover 1008' to the base 1006'. The layers of non-conductive adhesive 1020', 1022' also function to space the cover 1008' from the base 1006' so that a channel 1024' running along the center of the sensor-portion 1002' of the test strip 1000' is formed. A layer of conductive adhesive 1026' enables the transfer of signal from the major surface 1006*a'* of the base 1006' to the major surface 1008*b'* of the cover 1008'. The layer of electrically conductive adhesive 1026' can be made from a pressure-sensitive adhesive doped with an electrically conductive material, e.g., carbon. The layer of electrically conductive adhesive 1026' typically has a thickness of about 0.002 inch.

At least one electrical passageway 1028' enables the transfer of signal from the major surface 1008*b'* of the cover 1008' to the major surface 1008*a'* of the cover 1008'. An electrical passageway 1028' is a passageway formed in the cover 1008'.

The at least one electrical passageway 1028' is filled with electrically conductive material, such as, for example, carbon. The benefit resulting from the use of one or more electrical passageways is that all of the contacts of the sensor-containing portion of the test strip can be positioned on one major surface of the cover of the test strip. The electrical passageways 1028' are identical to or substantially similar to the electrical passageways 1028 previously described and shown in FIG. 28.

Figure 32:
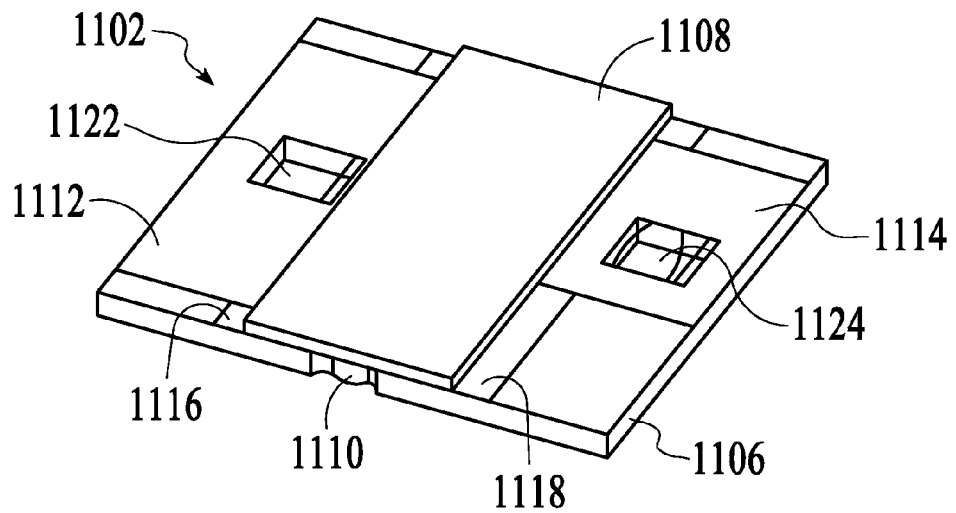
FIG. 32 is a perspective view of the sensor-containing portion of the test strip shown in FIG. 31.

While not critical, it is advantageous that the dimensions of the sensor-containing portion 1002' of the test strip 1000' be as small as possible in order to in order to reduce the size of the magazine 118 and reduce the volume of sample required to carry out a test. Typical dimensions of the base 1006' and cover 1008' are about 6 mm×6 mm×<2 mm. Typical dimensions of the electrodes and typical dimensions of channels 1024' that may be used are described in U.S. Pat. Nos. 6,229,757 and 6,616,819, incorporated herein by reference. When the sample of biological liquid is introduced at the sample receiving area, e.g., hydrophilic recesses 1010' and 1012', if present, the sample is easily drawn up into the channel 1024', along which the sample flows by means of capillary attraction. The major surface of the cover 1008' not facing the base 1006' has electrical contact pads 1029a', 1029b', 1029c' exposed, which electrical contact pads 1029a', 1029b', 1029c' are in contact with the contact leads 1030a, 1030b, 1030c, 1030d of the carrier 296, as shown in FIG. 30C. The base 1006' also has two openings 1032', 1034' formed therein on either side of one leg of the L-shaped electrode 1014'. The function of these openings 1032', 1034' is to securely attach the sensor-containing portion 1002' of the test strip 1000' to the lancet-containing portion, which holds the lancet in place. When the sensor-containing portion of the test strip has recesses in the sides of the cover, as shown in FIGS. 26 and 29A, the tabs of the lancet-containing portion of the test strip project downwardly, in the manner of the tabs of the lancet-containing portion shown in FIG. 26. When the sensor-containing portion of the test strip has openings in the base, as shown in FIGS. 30B, 31, and 32, the tabs of the lancet-containing portion of the test strip project upwardly, in the manner of the tabs of the lancet-containing portion shown in FIG. 31. The test strip 1000' of this embodiment can employ the same carrier 296 that can be used with the embodiment of the test strip 1000 previously described and the same type of meter as described in U.S. Pat. No. 6,616,819.

Figure 33:
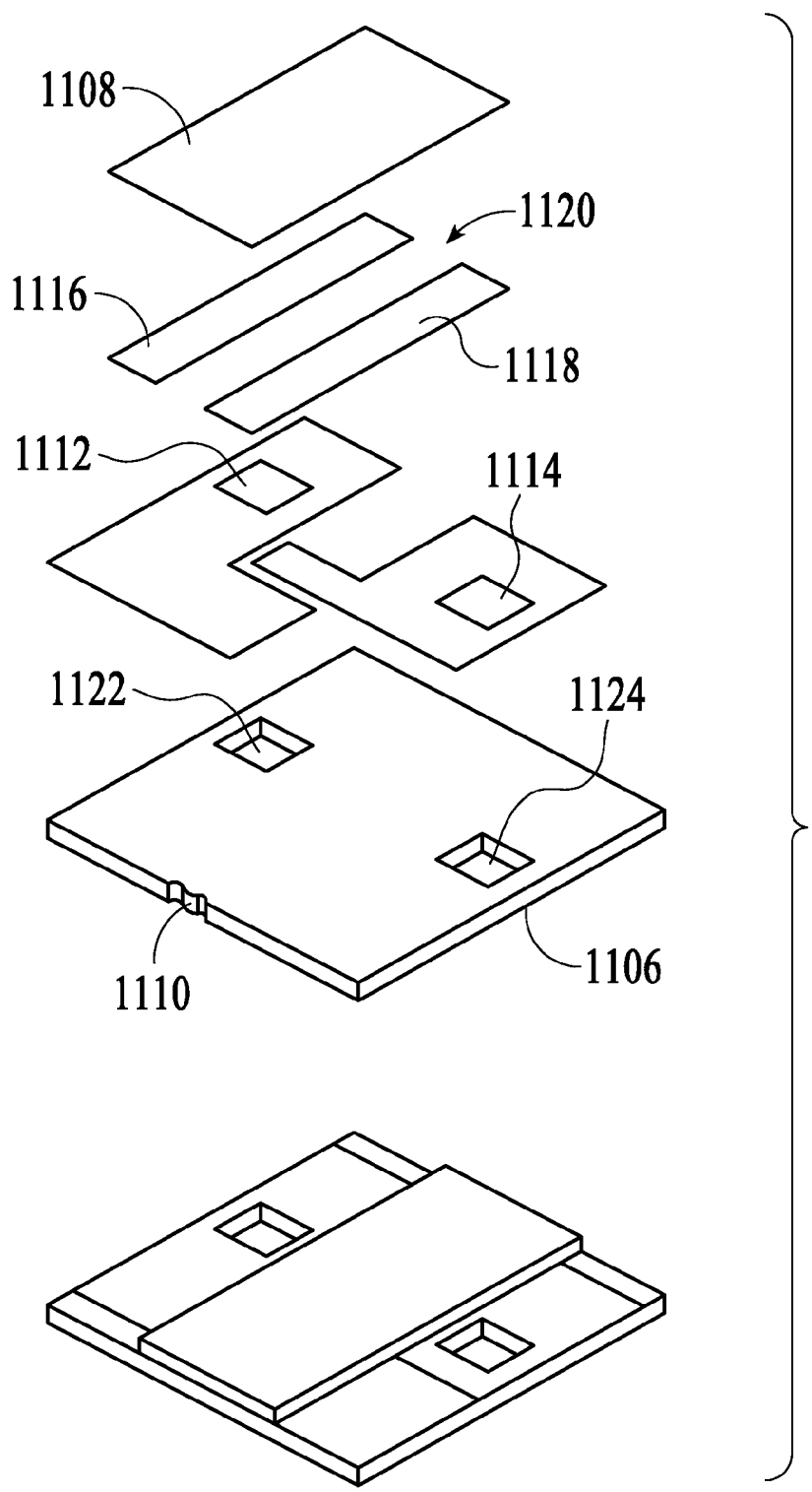
FIG. 33 is an exploded perspective view of the sensor-containing portion of the test strip shown in FIG. 31.

In still another embodiment, as shown in FIGS. 31-33, inclusive, a test strip 1100 includes a sensor-containing portion 1102 and a lancet-containing portion 1104. The sensor-containing portion 1102 includes a base 1106 and a cover 1108. The base 1106 is substantially rectangular in shape and has two major surfaces 1106a, 1106b and four edges 1106c, 1106d, 1106e, and 1106f. The base 1106 has a recess 1110 formed in one edge thereof. The surface of this recess 1110 bears a hydrophilic material in order to enable the sample of biological liquid to have greater affinity for the recess 1110 than if the recess were not bearing a hydrophilic material.

On one major surface of the base 1106 is a layer of electrically conductive material 1112 in a first area and a layer of electrically conductive material 1114 in a second area. The first area constitutes the working electrode and the second area constitutes the trigger electrode. The cover 1108 is separated from the base 1106 by layers 1116, 1118 of non-conductive adhesive applied to the base 1106 and cover 1108 in such a manner that a channel 1120 forming a sample flow path is created. This channel 1120 runs along the center of the sensor-portion 1102 of the test strip 1100. The cover 1108 is made of an electrically conductive material (such as, for example, vinyl having an electrically conductive material, e.g., Ag/AgCl, thereon) and functions as a dual purpose reference/counter electrode. When a sample of biological liquid is introduced at the hydrophilic recess 1110, the sample is easily drawn up into the channel 1116, along which the sample flows by means of capillary attraction. Portions of the electrically conductive material of the base 1106 function as electrical contact pads. The base 1106 has two openings 1122, 1124 formed therein on either side of the cover 1108. The function of these openings 1122, 1124 is to securely attach the sensor-containing portion 1102 of the test strip 1100 to the lancet-containing portion 1104, which holds the lancet in place. This embodiment does not require a conductive adhesive or electrical passageways to carry out determination of analytes.

The test strip 1100 of this embodiment can employ the same carrier 296 that can be used with the embodiments of the test strips 1000, 1000' previously described and the same type of meter as described in U.S. Pat. No. 6,616,819, which is incorporated by reference.

Below a sample application well or zone of a test strip may be a wicking membrane that is striped with various reagents to create various reagent, capture and/or eluate zones. A hemolysis reagent zone may be positioned below a sample application zone. The hemolysis reagent zone may include a hemolysis reagent that is striped, such as absorbed, confined, or immobilized, on a wicking membrane of the test strip. A small amount of hemolysis reagent, such as about 1 to about 2 or about 3 microliters, for example, is sufficient for striping the wicking membrane such that the hemolysis reagent zone is sufficiently confined on the test strip. Any reagent or combination of reagents suitable for hemolysis, and the consequent liberation of hemoglobin, can be used. By way of example, an ionic detergent, such as sodium dodecyl sulfate (SDS), a non-ionic detergent, such as a octylphenol ethylene oxide condensate or octoxynol-9 or t-octylphenoxypolyethoxy-ethanol, sold under the name, Triton X-100, and commercially available from Sigma Chemical or Sigma-Aldrich Co., or a hypotonic solution, may be used as a hemolysis reagent.

A glycated hemoglobin capture zone may be disposed downstream relative to the hemolysis zone. By way of example, any chemical reagent comprising at least one boron ligand, such as phenyl boronate or other boron affinity chemistry used in the above-referenced Glycosal test, or such as m-aminophenylboronic acid, such as that of a gel that is immobilized on cross-linked, beaded agarose, any antibody, such as anti-HbA1c antibody available from a number of sources, any immunoassay reagent, any chemical reagent including at least one binding ligand, such a boronic acid involving boron binding ligands, and the like, and any combination thereof, that is suitable for the binding of glycated hemoglobin to the capture zone 222, such as via covalent bonds, for example, or the capture of glycated hemoglobin in capture zone 222, may be used. A hemolysis layer/zone and a glycated hemoglobin capture zone can be integrated to form an integrated reagent zone.

A lancet 1200 can be integrated directly into the sensor-containing portion 1002, 1002', 1102 of the test strip. Alternatively, the sensor-containing portion 1002, 1002', 1102 of the test strip can be attached to the lancet-containing portion of the test strip. The medical diagnostic device 100 can have an alignment feature to ensure that movement, e.g., rotation, of the test strip during use does not result in misalignment of the sample application zone of the test strip. The alignment feature can be provided by springs associated with the carrier 296.

The lancet-containing portion 1004 shown in FIG. 26 can be used with, or can be modified to be used with, any of the sensor-containing portions 1002, 1002', and 1102 described herein. For example, the tabs for connecting the lancet-containing portion to the sensor-containing portion can be modified to project upwardly to enable the lancet-containing portion to be used with a sensor-containing portion having openings in the base, rather than recesses in the sides of the base and the cover. It should be noted that other embodiments of the lancet-containing portion can be used with any of the sensor-containing portions 1002, 1002', and 1102 described herein. As shown in FIG. 26, the lancet-containing portion 1004 is shown as having a lancet-containing body 1202. The lancet 1200 is held in the lancet-containing body 1202. The lancet-containing body 1202 can be attached to the sensor-containing portion 1002 by tabs 1036, 1038 or can be attached to the sensor-containing portion 1002', 1102 by tabs 1136, 1138. When the sensor-containing portion of the test strip has recesses in the sides of the cover, as shown in FIGS. 26 and 29A, the tabs 1036, 1038 of the lancet-containing portion of the test strip project downwardly, in the manner of the tabs of the lancet-containing portion shown in FIG. 26. When the sensor-containing portion of the test strip has openings in the base, as shown in FIGS. 30B, 31, and 32, the tabs 1136, 1138 of the lancet-containing portion of the test strip project upwardly, in the manner of the tabs of the lancet-containing portion shown in FIG. 31. Any suitable dimensions of the lancet-containing body may be employed, and in certain embodiments the lancet-containing body 1202 of the lancet-containing portion 1004 is 10 mm×8 mm×1.5 mm. Typical dimensions of the protective cover 1204 for the lancet 1200 are 3 mm×1.4 mm. Typical dimensions of the needle for forming the lancet 1200 are 28 to 30 gauge, 10 mm total length, 3.5 mm exposed length.

A lancet 1200 for puncturing the skin to obtain a sample of biological liquid includes a sharp metal component (needle) that is maintained in a sterile condition until the moment of use. In addition, an ideal lancet 1200 is disposable with minimum possibility of an injury subsequent to the initial use. The lancet 1200 includes a substantially cylindrical needle having a sharp end and an opposing end which may be a blunt end. The tip 1200a of the lancet 1200, i.e., the sharp end, has a protective cover 1204 that ensures sterility of the lancet 1200. The protective cover 1204 is also designed to be re-attached to the tip 1200a of the lancet 1200 for safe disposal. The blunt end can be embedded into the lancet-containing body 1202 by insert molding or adhesive. In one embodiment, the lancet-containing body 1202 includes a polymeric material molded into a substantially rectangular shape.

The tip 1200a of the lancet 1200 and as much of the lancet 1200 as is expected to puncture the skin of the patient can embedded in the protective cover 1204, e.g., a polymeric plug, which may be an elastomeric plug, e.g., thermoplastic elastomeric, silicone, plug. In this configuration, ionizing radiation can be used to sterilize the lancet 1200 and the elastomer will prevent subsequent contamination. Embedding the piercing portion (tip) 1200a of the lancet 1200 in a soft material does not damage the delicate tip 1200a of the lancet 1200 but forms a tight seal that allows for sterilization (such as by irradiation) and the preservation of that sterile condition. Such a protective cover 1204 can be removed from the piercing portion of the lancet 1200 either by pulling the protective cover 1204 off the tip 1200a of the lancet 1200 or by fully piercing the protective cover 1204 and allowing the protective cover 1204 to cover a more proximal part of the lancet 1200.

The nature of the thermoplastic elastomer (TPE) eliminates the necessity of relocating the tip 1200a of the used lancet 1200 precisely into the hole originally occupied by the tip 1200a of the unused lancet 1200. Relocation of the tip 1200a of the lancet 1200 at any position in the thermoplastic elastomeric protective cover 1204 is sufficient to prevent the tip 1200a of the lancet 1200 from being exposed after the test strip is ejected from the medical diagnostic device 100.

Thermoplastic elastomers (TPE) are easily processed rubbery materials. They can be easily formed in various shapes. If a sharp lancet 1200 is embedded into a piece of thermoplastic elastomer, and then irradiated by either gamma radiation or electron beam radiation of sufficient energy, the lancet 1200 is rendered sterile, and because the thermoplastic elastomer forms a tight seal, the lancet 1200 remains sterile for a relatively long period of time.

If the protective cover 1204 made is made of thermoplastic elastomer, and the thermoplastic elastomer is at least partially enveloped by a more rigid material, the protective cover 1204 acts more like a rigid body, but keeps the desired features of the thermoplastic elastomer. Configurations of this design might include the lamination of thermoplastic elastomer between thin layers of rigid plastic or metal or the coextrusion of thermoplastic elastomer with a more rigid polymer. The cross-section of such a coextruded profile can be circular, rectangular, or any other shape that renders it useful. Such a combination of thermoplastic elastomer and rigid material can be provided with features such that the combination is allowed to slide proximally on the shaft of the lancet 1200, eventually exposing the tip 1200a of the lancet 1200 for lancing. After the lancet 1200 is used, the subassembly can be slid distally and the connection between the protective cover 1204 and the lancet 1200 changed such that the protective cover 1204 cannot return to a position that exposes the tip 1200a of the lancet 1200.

It should be noted that all of the embodiments of the test strip shown herein are characterized by having the tip 1200a of the lancet 1200 of the lancet-containing portion 1004 of the test strip located 180° from the uptake recess_of the sensor-containing portion 1002, 1002', 1102 of the test strip. Such positioning renders the test strips suitable for use with the medical diagnostic device.

The test strips and the magazines 118 containing a plurality of test strips can be made by the following process:

To prepare the lancet-containing portion 1004 of a test strip, unfinished lancets are provided. These unfinished lancets are ground and cut to 10 mm. The ground, cut lancets 1200 are then molded into a plastic body 1202 to form the lancet-containing portion 1004 of the test strip. To prepare the sensor-containing portion 1002, 1002', 1102 of the test strip, the electrodes are printed onto the backing or cover, the appropriate reagents (discuss these) are coated over the electrodes, and the cards of sensor-containing portions 1002, 1002', 1102 are singulated to form individual sensor-containing portions 1002, 1002', 1102. The individual sensor-containing portions 1002, 1002', 1102 are combined with the lancet-containing portions 1004 to form completed test strips. Pluralities of test strips are then loaded into magazines 118.

The sensors described herein may be configured for analysis of an analyte in a small volume of sample by, for example, coulometry, amperometry, and/or potentiometry. The sensors may also be configured for optical analysis. The sensors may be configures to determine analyte concentration in about 1 µL or less of sample, e.g., 0.5 µL or less of sample e.g., 0.25 µL or less of sample e.g., 0.1 µL or less of sample. The chemistry of the sensors generally includes an electron transfer agent that facilitates the transfer of electrons to or from the analyte. One example of a suitable electron transfer agent is an enzyme which catalyzes a reaction of the analyte. For example, glucose, oxidase or glucose, dehydrogenase, such as pyrroloquinoline quinone glucose, dehydrogenase (PQQ), may be used when the analyte is glucose. Other enzymes may be used for other analytes. Additionally to or alternatively to the electron transfer agent, may be a redox mediator. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator may be a polymeric redox mediator or a redox polymer (i.e., a polymer having one or more redox species). Examples of suitable redox mediators and redox polymers are disclosed in U.S. Pat. Nos. 6,338,790; 6,229,757; 6,605,200 and 6,605,201, which are incorporated by reference.

The sensor also includes a sample chamber to hold the sample in electrolytic contact with the working electrode. In certain embodiments, the sample chamber may be sized to contain no more than about 1 µL of sample, e.g., no more than about 0.5 µL, e.g., no more than about 0.25 µL, e.g., no more than about 0.1 µL of sample.

The magazines 118 can be prepared by first molding the desiccants into platforms. Resilient biasing elements and the platforms are then assembled into the housings of the magazines. The magazines are then packed and shipped.

Operation

Figure 34:
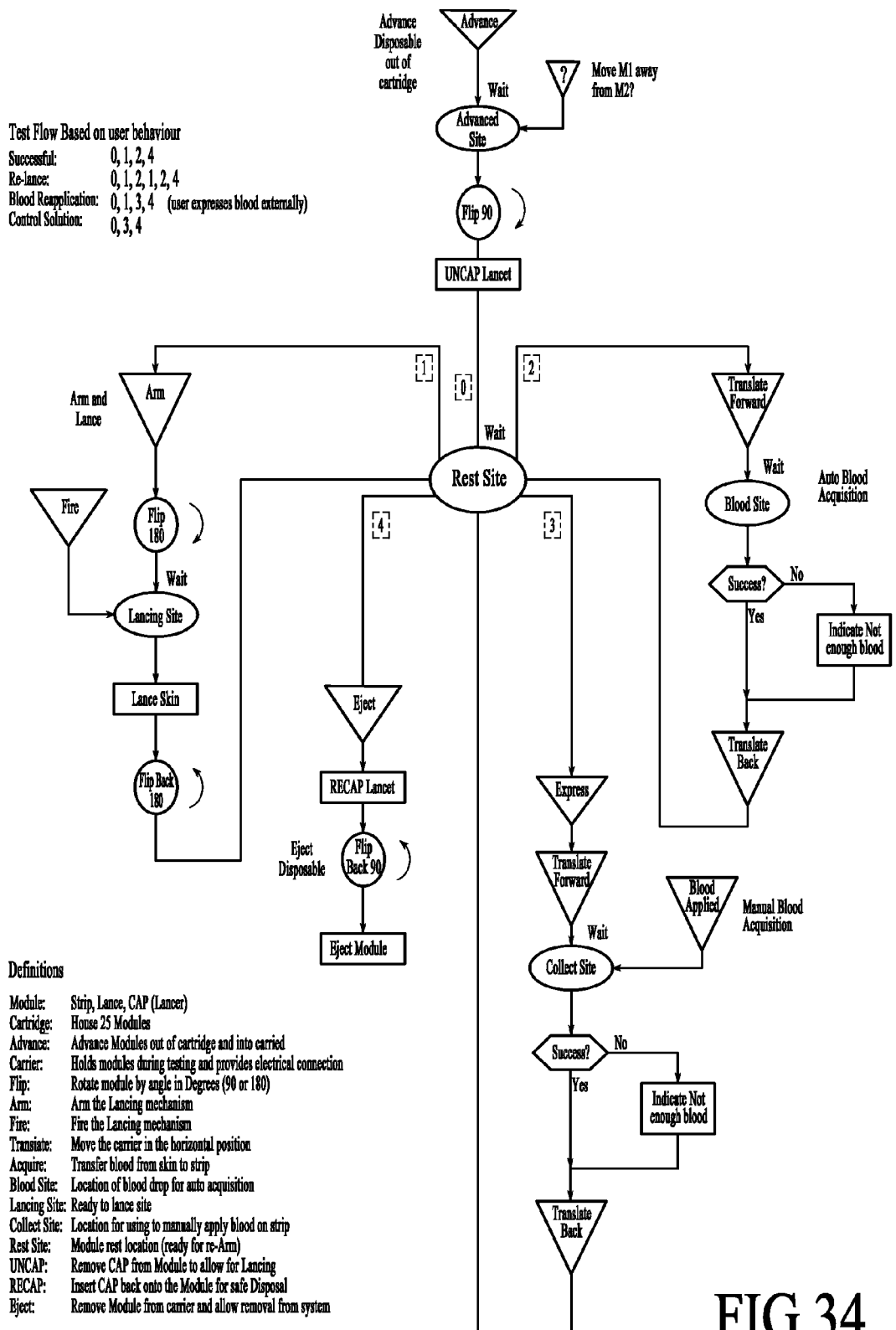
FIG. 34 is a flow chart illustrating the operations of the medical diagnostic device of an alternative embodiment.

Embodiments for operating the medical diagnostic device 100 to dispense a test strip, form an opening in the skin of a patient to obtain a sample of biological liquid, collect a sample of biological liquid from the patient, analyze the sample of biological liquid collected from the patient, and dispose of the used test strip will now be described. FIG. 34 also depicts the operational steps in a flow chart. In most places above and below herein, the reference numerals ending with "a" are left off for convenience, although most reference numerals having a corresponding numeral ending in "a" is intended to have the corresponding numeral there, and such are hereby incorporated there.

Referring now to FIGS. 1-7, the assembly 110 for storing and dispensing a plurality of test strips is inserted into the housing 102 of the medical diagnostic device 100. The housing has a door_through which the assembly 110 can be introduced to the proper position in the interior of the housing 102. The door_is on the side of the housing 102 opposite to the side of the housing 102 having the display 238. The door can be mounted by means of at least one hinge or can be mounted by a snap-fit feature.

For the sake of simplification, the test strip will be the test strip shown in FIGS. 26A-B. Other test strips described can be used in place of the test strip shown in FIG. 26A-26B. Each test strip 1000, 1000a in the assembly 110 has a lancet-containing portion and a sensor-containing portion 1002. The lancet-containing portion 1004 of the test strip 1000 has a protective cover 1204 to render the tip 1200a of the lancet 1200 sterile and prevent the tip 1200a of the lancet 1200 from causing an unwanted puncture. The sensor-containing portion 1002 of the test strip 1000 emerges first from the magazine 118. In order to feed a test strip 1000 from the magazine 118 to the cradle 280 of the lancing/collecting assembly 112, the lowermost test strip 1000 in the assembly 110 is fed from the assembly 110 to the cradle 280 of the lancing/collecting assembly 112.

In order to advance a test strip 1000 from the magazine 118 to the cradle 280 of the lancing/collecting assembly 112, the user causes the slide 142 to move in the required direction. Movement of the slide 142 alone, or in combination with another feature, enables the magazine 118 to become unsealed, so that a test strip 1000 can be removed from the magazine 118. When the magazine 118 is unsealed, the mechanism for advancing a test strip 1000 from the assembly for storing and dispensing test strips 110 to the lancing/collecting assembly 112 advances a test strip 1000 into the cradle 280 of the lancing/collecting assembly 112 and positions the test strip 1000 so that proper lancing, collecting of sample of biological liquid, and analyzing of the collected sample can be carried out. Prior to the lancing step, the protective cover 1204 of the lancet 1200 is removed, either before the test strip 1000 is positioned in the cradle 280 or after the test strip 1000 is positioned in the cradle 280. The assembly 114 for removing a protective cover 1204 from the tip 1200a of a lancet 1200 and re-attaching the protective cover 1204 to the tip 1200a of a used lancet 1200 retains the protective cover 1204 for subsequent re-attachment to the tip 1200a of the lancet 1200 of the lancet-containing portion 1004 of the test strip 1000 after the lancing step, the collecting step, and the analyzing step are completed.

After the test strip 1000 has been fed into the cradle 280, the medical diagnostic device 100 causes the test strip 1000 to be oriented in such a manner that the lancet 1200 of the lancet-containing portion 1004 of the test strip 1000 can be introduced into the skin of a patient to form an opening in the skin of the patient. In embodiments, such an orientation step is carried out by a motor. In these embodiments, the PCB assembly 232 can be programmed so that orientation is carried out accurately and reliably.

Such an orientation step is carried out by having the transmission system rotate the cradle 280 of the lancing/collecting assembly 112 about 90° (clockwise or counterclockwise), so that the tip 1200a of the lancet 1200 faces the opening_in the end cap 104, so that when the medical diagnostic device 100 is placed against the skin of the patient, the tip 1200a of the lancet 1200 will be facing the skin of the patient.

Then, the lancing/collecting assembly 112 is armed. Movement of the slide 460 causes a sufficient amount of energy for lancing and retracting to be stored in the torsion spring 388.

Appropriate movement of the slide 460 causes the locking tab 402 to abut the locking tab 404 to arm the lancing/collecting assembly 112. In an alternative embodiment, the lancing/collecting assembly 112 can be armed by means of a motor, thereby eliminating the need for the slide 460.

After the lancing/collecting assembly 112 is armed, the medical diagnostic device 100 is placed against the skin of the patient in such a manner that the opening in the end cap 104 overlies the position where the patient desires to puncture the skin. When the patient is ready to trigger the lancet 1200, the patient actuates the trigger 406, to disengage the locking tab 402 from the locking tab 404, thereby allowing the carrier 296 to traverse the slots 288 and 290 in the cradle 280 and move rapidly toward the skin of the patient, whereby the lancet 1200 in the lancet-containing portion 1004 of the test strip 1000 causes an opening to be formed in the skin of the patient. Immediately after the opening is formed in the skin of the patient, the carrier 296 is retracted by the action of the lancing cam 338, whereupon the lancet 1200 of the lancet-containing portion 1004 of the test strip 1000 moves away from the skin of the patient. Meanwhile, the sample of biological liquid is caused to emerge from the opening formed in the skin of the patient The medical diagnostic device 100 then causes the test strip 1000 to be oriented in such a manner that the sensor-containing portion 1002 of the test strip 1000 can be placed in contact with the sample of biological liquid emerging from the opening in the skin of the patient. For this step, the cradle 280 is rotated 180° so that the sensor-containing portion 1002 of the test strip 1000 directly overlies the biological liquid.

The medical diagnostic device 100 then enables the index cam 338 to move the cam follower 274 so that the carrier 296 can traverse the slots 288 and 290 to move toward the opening in the skin of the patient so that the sensor-containing portion 1002 of the test strip 1000 is able to collect biological liquid emerging from the opening in the skin of the patient. The carrier 296 and the movements thereof can be designed so that the carrier 296 can move toward and away from the skin in such a manner that a suitable quantity of biological liquid is collected. The flexibility of the flexible component 422 of the cam follower 274 assists in obtaining a sample of biological liquid from the opening in the skin of the patient.

The sample of biological liquid enters the sample application zone of the sensor-containing portion 1002 of the test strip 1000, i.e., the recesses 1010, 1012 formed in an edge of the test strip 1000. The sample of biological liquid travels along the sample flow channel 1024 to the area where the reagents are disposed. The appropriate reaction occurs, thereby activating the electronics and bringing about a reading of the concentration of the analyte, which reading is shown in the display. If insufficient quantity of the sample of biological liquid is drawn in the initial lancing step, the user can actuate a retesting procedure before actuating the analyzing step, whereby the test is aborted so that the user can re-arm the lancing mechanism and begin again.

The sensor-containing portion 1002 of the test strip 1000 collects a sufficient quantity of sample of biological liquid to allow analysis of the sample of biological liquid. After a sufficient amount of sample of biological liquid is collected, the carrier 296, the electrical components of which are in electrical contact with the contacts of the sensor-containing portion 1002 of the test strip 1000, measures the quantity of analyte in the sample by means of an electrochemical analyzer. By this process, the sample of biological liquid is analyzed to determine at least one characteristic of the sample of biological liquid.

After the sample of biological liquid is analyzed, the protective cover 1204 is re-attached to the tip 1200a of the lancet 1200 of the lancet-containing portion 1004 of the test strip 1000. After the protective cover 1204 is re-attached, the re-covered test strip 1000 is ejected from the port 230 in the housing 102.

FIG. 34 is a flow chart that illustrates various steps of a method in accordance with several embodiments. As shown in FIG. 34, there are five basic components of the method. Component 0 involves advancing the test strip from the magazine 118 into the cradle 280, removing the protective cover 1204 from the lancet 1200, and rotating the cradle 280 to position the lancet 1200 for entering the skin of the patient. It should be noted that the protective cover 1204 could be removed from the lancet 1200 prior to rotating the cradle 280 into position for lancing. Component 1 involves arming and triggering the lancet 1200. Component 2 involves indexing the test strip so that the sensor portion of the test strip can obtain blood from the opening formed in the skin in Component 1. Component 3 involves collecting blood from the opening formed in the skin in Component 1. Component 4 involves reattaching the protective cover 1204 to the lancet 1200 and ejecting the used test strip from the medical diagnostic device 100.

Figure 35G:
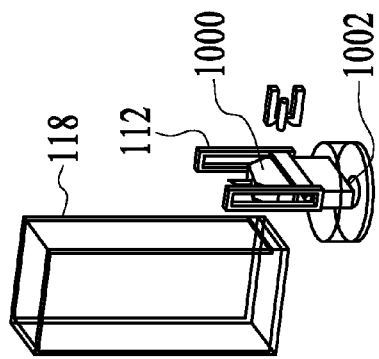
Figure 35H:
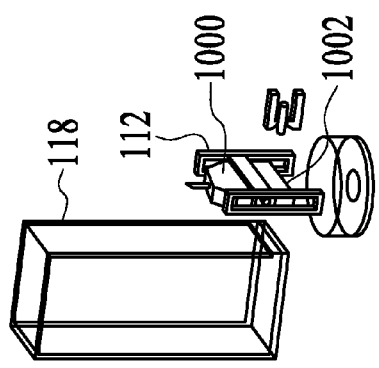
Figure 35I:
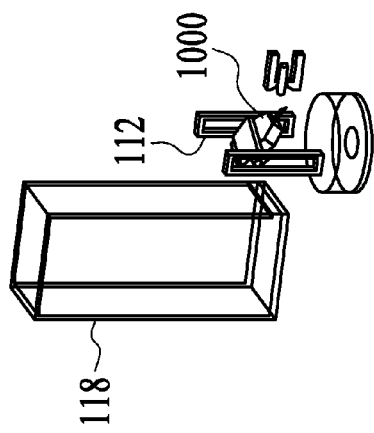
Figure 35J:
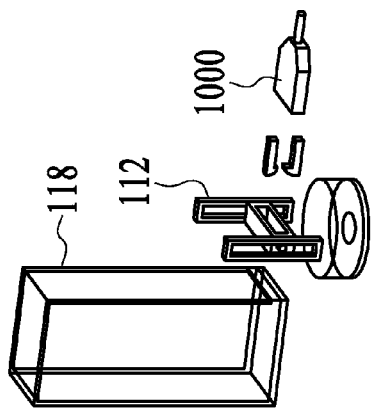
Figure 35K:
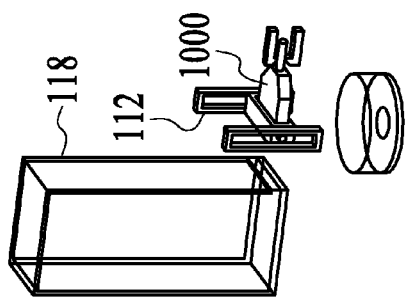
Figure 35L:
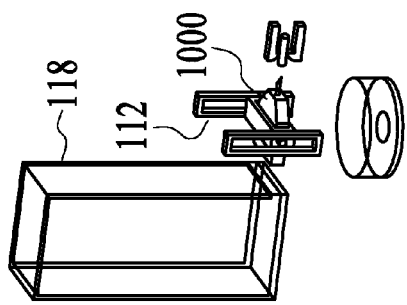
Figure 35M:
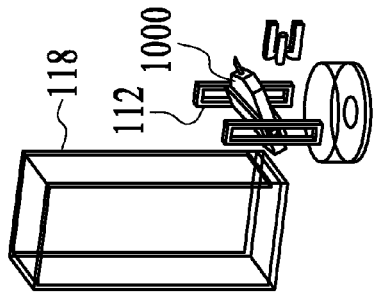

FIG. 35A through FIG. 35M, inclusive, illustrate in schematic form one way of carrying out a method according to embodiments herein. For the sake of simplification, the test strip will be the test strip shown in FIG. 26. Other test strips described can be used in place of the test strip shown in FIG. 26. FIG. 35A shows a test strip 1000 in the magazine 118. FIG. 35B shows the test strip 1000 advanced from the magazine 118 and inserted into the lancing/collecting assembly 112, which is represented schematically by two parallel upright elements, each element having a slot formed therein. FIG. 35C shows the protective cover 1204 being removed from the lancet 1200 of the test strip 1000. It should be noted that the protective cover 1204 could be removed before the test strip 1000 is inserted into the lancing/collecting assembly 112. FIG. 35D shows the test strip 1000 rotated 90° so that the lancet 1200 is in position for lancing the skin of the patient. FIG. 35E shows that the lancet 1200 has entered the skin of the patient. FIG. 35F shows that the lancet 1200 has been retracted from the skin of the patient. FIG. 35G shows that the test strip 1000 is being rotated 180° so that the sensor-containing portion 1002 can collect biological liquid emerging from the opening formed in the skin of the patient. FIG. 35H shows that the sensor-containing portion 1002 of the test strip 1000 is ready to be indexed so that the sensor-containing portion 1002 can collect biological liquid emerging from the opening formed in the skin of the patient. FIG. 35I shows the sensor-containing portion 1002 of the test strip 1000 contacting the biological liquid emerging from the skin of the patient. FIG. 35J shows that the test strip 1000 is being rotated 90° so that the test strip 1000 will come into the proper in position for being ejected from the medical diagnostic device. FIG. 35K shows the test strip 1000 in position for ejection from the medical diagnostic device 100. FIG. 35L shows the protective cover 1204 being reattached to the lancet 1200. FIG. 35M shows the test strip 1000 being ejected from the medical diagnostic device 100.

Alternative Embodiments

In an alternative embodiment, a medical diagnostic device is provided that carries out the functions of:
  (a) storing a plurality of lancets and sensors;
  (b) feeding a plurality of lancets and sensors to a system that employs a lancet to form an opening in the skin of a patient and then employs the sensor to collect a sample of biological liquid that emerges from the opening formed in the skin;
  (c) forming an opening in the skin of the patient by means of the lancet;
  (d) collecting the sample of biological liquid emerging from the opening formed in the skin of the patient by means of the sensor;
  (e) analyzing the sample of biological liquid collected by the sensor; and
  (f) ejecting the used lancet and the used sensor in a safe manner.

In a further embodiment, a test strip includes a lancet-containing portion and a sensor-containing portion. During the time that the test strip is stored in the medical diagnostic device, a protective cover encloses the lancet of the lancet-containing portion. The medical diagnostic device is capable of removing the protective cover to enable the lancet to form an opening in the skin of the patient and is further capable of re-attaching the protective cover onto the lancet to enable the medical diagnostic device to eject the used test strip in a safe manner.

In another embodiment, a lancing/collecting assembly receives a test strip that includes both a lancet-containing portion and a sensor-containing portion. By means of various operations, the lancing/collecting assembly is configured to (a) orient the lancet-containing portion of the test strip in such a manner that the lancet of the lancet-containing portion of the test strip can be advanced toward a lancing and testing site on the skin of the patient in order to form an opening therein, (b) arm the lancet of the lancet-containing portion of the test strip, (c) trigger the armed lancet of the lancet-containing portion of the test strip so that the lancet forms an opening in the skin of the patient at the lancing and testing site, (d) orient the sensor-containing portion of the test strip in such a manner that the sensor-containing portion of the test strip can be advanced toward the opening formed in the skin of the patient to collect a sample of biological liquid emerging from the opening in the skin of the patient at the lancing and testing site which remains proximate to a lancing and testing port of an analyte, e.g., glucose, monitoring apparatus; and (e) advance the sensor of the sensor-containing portion of the test strip so that sufficient quantity of the sample of biological liquid can be collected for analysis to determine a parameter of the biological liquid, e.g., a body analyte, e.g., glucose, level.

The lancing/collecting assembly may also incorporate an analyzer that is capable of analyzing the sample of biological liquid collected from the opening in the skin of the patient.

In another embodiment, a storing/dispensing assembly is provided for a plurality of test strips, each of which includes a lancet-containing portion and a sensor-containing portion.

In a further embodiment, a method for using a medical diagnostic device includes:
(a) feeding one of multiple test strips, each of the test strips having a lancet-containing portion and a sensor-containing portion, to a lancing/collecting assembly that employs a lancet of the lancet-containing portion to form an opening in the skin of a patient, and then employs a sensor of the sensor-containing portion to collect a sample of biological liquid that emerges from the opening formed in the skin;
(b) forming an opening in the skin of the patient by means of a lancet in the lancet-containing portion;
(c) collecting a sample of biological liquid emerging from the opening formed in the skin of the patient by means of the sensor of the sensor-containing portion;
(d) analyzing the sample of biological liquid collected by the sensor of the sensor-containing portion; and
(e) ejecting the used test strip in a safe manner.

The medical diagnostic device of this embodiment can perform a plurality of diagnostic tests, e.g., 25 tests, before the device requires refilling with test strips. The medical diagnostic device can perform the functions of storing and dispensing test strips, lancing the skin of a patient, collecting a sample of biological liquid, analyzing the sample of biological liquid collected, and disposing of used test strips. In the case of collection of an inadequate quantity of sample, the medical diagnostic device enables re-lancing.

In accordance with another embodiment, the medical diagnostic device requires only a small volume of sample to carry out a complete test, e.g., 0.3 microliter (see, e.g., U.S. Pat. Nos. 7,058,437, 6,618,934, 6,591,125 and 6,551,494, which are hereby incorporated by reference).

The test strip combines a lancet and a sensor in a single small unit. After the skin of the patient is pierced and a sample of biological liquid, e.g., blood, appears, the test strip is moved into position for collecting a sample of the liquid, and the liquid enters the sample application zone of the sensor-containing portion of the test strip without manipulation of the test strip by the user.

Further features and advantages include the small, readily portable and storable size of the integrated meter. The integrated meter is small enough to be handheld, and easily handled by a self-care diabetic. In some embodiments, the meter is less than 5" tall, less than 3" wide, and less than 1.5" deep. In some of these embodiments, the meter is less than 4" tall and in one embodiment, just under 3.5" tall. In some embodiments, the meter is less than 2.6" wide, such as between approximately 2.5" and 2.6" wide, and just under 1.5" deep. The meter may be rectangular, or one or both sides may be contoured concave or convex, as may the top and/or bottom, and the front and back faces.

In some embodiments, the meter may be plugged in, but is also powered by a battery which is located substantially oppositely to where the striplets are accessed, i.e., disposed oppositely in at least one dimension of the meter. The battery may be provided in a compartment at the top and back of the meter, which is opposite the striplet access near the front and bottom of the meter, i.e., disposed oppositely in at least two dimensions. In some embodiments, the striplet is exposed from lancing and testing and ejection at one side of the meter, while the battery compartment is at the other side, i.e., disposed opposite the striplet access in all three dimensions.

The striplet is also small in size. Generally the striplet is less than 2 mm×less than 1 mm×less than 0.3 mm, and in some embodiments, less than 1.5 mm×less than 0.75 mm×less than 0.2 mm, e.g., approximately 1 mm×0.5 mm×0.1 mm.

The meter and striplet are advantageously ideal for alternative site testing, i.e., away from the fingertips, where smaller amount of blood are available than at the fingertips, such as less than 1 microliter, and even less than 0.5 microliters, or less than 0.3 microliters, or less than 0.2 microliters, or even 0.1 microliters (100 nanoliters). See for example U.S. Pat. No. 6,284,125 which describes this feature in more detail and in incorporated by reference.

The system includes, in some embodiments, calibration one or more schemes. A calibration module, whether it be a bar code, a RFID tag, a label, or otherwise may be located on a striplet and/or on a striplet container. U.S. application Ser. No. 11/350,398, which is assigned to the same assignee and incorporated by reference, provides further examples. There may be contact pads that may be shorted together or kept apart during the test strip manufacturing process in order to communicate a calibration code to the meter. There may be a set of contact pads and a varying resistance between the two pads where the resistance is changed during the manufacturing process of the test strip to communicate a calibration code to the meter. There may be an electrical memory that is readable and writable by the meter, which communicates a calibration code to the meter. A calibrator can carry other information such as striplet expiration and/or a striplet number count down.

In addition, a data processing terminal may include a personal computer, a portable computer such as a laptop or a handheld device (e.g., personal digital assistants (PDAs)), and the like, each of which may be configured for data communication with the integrated meter, or a receiver associated therewith, via a wired or a wireless connection. Such data processing terminal may be connected to a data network for storing, retrieving and updating data corresponding to a detected analyte level of a user.

The data processing terminal may include an infusion device such as an insulin infusion pump or the like, which may be configured to administer insulin to patients, and which may be configured to communicate with the integrated meter for receiving, among others, the measured analyte level and/or transmitting insulin dose values or other information relating to a diabetes care or other health care regimen. Alternatively, a receiver unit may be especially provided for receiving communications from the integrated meter, and may be configured to integrate an infusion device therein or otherwise communicate therewith. The receiver unit may be configured to administer insulin therapy to patients, for example, for administering and modifying basal profiles, as well as for determining appropriate boluses for administration based on, among others, the detected analyte levels received from the integrated meter.

Additionally, the integrated meter may be configured for bi-directional wireless communication, or may be configured in a network of devices that communication via a network hub. The integrated meter may be configured to communicate (that is, transmit data and/or receive data) from multiple devices via a wired or wireless communication link. The communication link may include one or more of an RF communication protocol, an infrared communication protocol, a Bluetooth enabled communication protocol, an 802.11x wireless communication protocol, or an equivalent wireless communication protocol which provides secure, wireless communication of several units (for example, per HIPPA requirements) while avoiding potential data collision and interference.

The present invention is not limited to the embodiments described above herein, which may be amended or modified without departing from the scope of the present invention as set forth in the appended claims, and structural and functional equivalents thereof. The Background section is incorporated by reference into the detailed description as disclosing alternative embodiments.

In methods that may be performed according to embodiments herein and that may have been described above and/or claimed below, the operations have been described in selected typographical sequences. However, the sequences have been selected and so ordered for typographical convenience and are not intended to imply any particular order for performing the operations.

What is claimed is:

1. An analyte monitoring apparatus, comprising:
   a housing;
   a user interface coupled with the housing including one or more switches or a display or both;
   one or more integrated lancet and test strips contained in the housing that include both a lancet and an analyte test strip at different ends of the integrated lancet and test strip,
   wherein a longitudinal axis extends from the lancet end to the analyte test strip end of the integrated lancet and test strip, and wherein the test strip is flat and a lateral axis extends within a plane of the test strip and perpendicular to the longitudinal axis;
   a lancing and testing port defined in the housing for permitting the integrated lancet and test strip to contact a lancing site outside the housing;
   a set of mechanical components for loading an integrated lancet and test strip for a lancing and testing process, for advancing the integrated lancet and test strip for lancing through said port at a lancing site proximate to the port, for re-orienting the integrated lancet and test strip such that the integrated lancet and test strip is rotated about a line parallel to the lateral axis, and for advancing the integrated lancet and test strip for testing at said lancing site also through said port; and
   an analyzer for determining an analyte level of a body fluid applied to the test strip from the lancing site.

2. The apparatus of claim 1, further comprising a cartridge coupled into a slot in the housing which contains several integrated lancet and test strips.

3. The apparatus of claim 2, wherein the cartridge comprises at least one guide rail for relative positioning within the housing with respect to the set of mechanical components.

4. The apparatus of claim 2, further comprising a seal which generally maintains the integrated lancet and test strips within the cartridge free from exposure to ambient air, and is configured for releasing the seal temporarily to permit loading of an integrated lancet and test strip for a lancing and testing process.

5. The apparatus of claim 4, wherein the seal comprises an elastomeric seal.

6. The apparatus of claim 4, wherein the seal comprises a bellows.

7. The apparatus of claim 4, wherein the cartridge comprises at least one guide rail for relative positioning within the housing with respect to the set of mechanical components, said guide rail having a stopping point at which the cartridge remains stationary relative to the housing when said seal is temporarily broken for loading the integrated lancet and test strip.

8. The apparatus of claim 2, wherein the cartridge comprises a biasing member for providing the integrated lancet and test strips at a loading end of the cartridge.

9. The apparatus of claim 2, wherein the cartridge comprises a structural support for the integrated lancet and test strips within the cartridge.

10. The apparatus of claim 9, wherein the cartridge comprises a desiccating member for keeping the integrated lancet and test strips substantially free of moisture.

11. The apparatus of claim 10, wherein one or both of the structural support and desiccating member are provided as inserts.

12. The apparatus of claim 11, wherein the inserts comprise a hard plastic insert for providing said structural support and a desiccating plastic insert for providing said desiccating.

13. The apparatus of claim 1, wherein the set of mechanical components comprises an integrated lancet and test strip slot for holding the integrated lancet and test strip during re-orientation which includes rotation of the integrated lancet and test strip.

14. The apparatus of claim 13, wherein the integrated lancet and test strip slot is coupled with a cam that oscillates between points corresponding to different orientations of the integrated lancet and test strip for lancing and testing.

15. The apparatus of claim 14, wherein the said oscillation is about a point of unstable equilibrium.

16. The apparatus of claim 1, wherein the lancet and analyte test sensor are each coupled to a lancet body.

17. The apparatus of claim 16, wherein the lancet and test sensor each protrude from the lancet body, and wherein the one or more integrated lancet and test strips further comprise a lancet cap protecting the protruding lancet; and wherein said set of mechanical components include a cover-storing portion for removing the lancet cap.

18. The apparatus of claim 17, wherein the cover-storing portion is for providing a space and a frictional force for holding the lancet cap during a lancing and testing process, and for providing the lancet cap to re-cover the lancet for safe ejection of a used integrated lancet and test strip.

19. The apparatus of claim 1, wherein the set of mechanical components comprises:(i) a first mechanical subset including a first set of gears, a pusher, a tub sealing with a cartridge including the one or more integrated lancet and test strips, and a turret including an integrated lancet and test strip slot within which the integrated lancet and test strip is disposed during lancing and testing, wherein the first mechanical subset is for unsealing the tub and cartridge for accessing the integrated lancet and test strip, advancing the integrated lancet and test strip to the turret, and ejecting the integrated lancet and test strip after testing; and(ii) a second mechanical subset including a second set of gears, a blade and mating lancet cap contour, the turret, and a carriage which contains the turret, wherein the second mechanical subset is for arming/disarming the lancet by removing/replacing the lancet cap from/to over the lancet, re-orienting the integrated lancet and test strip between lancing and testing, and performing both lancing and testing through the lancing and testing port at the lancing site.

20. The apparatus of claim 19, wherein the disarming comprises replacing the lancet cap for safe ejection of a used testing integrated lancet and test strip.

21. The apparatus of claim 19, wherein the carriage translates in a same direction for both the lancing and the testing.

22. The apparatus of claim 21, wherein opposite ends of the integrated lancet and test strip are sequentially provided through the same lancing and testing port for the lancing and the testing.

23. The apparatus of claim 1, wherein the re-orienting of the integrated lancet and test strip comprises rotating the integrated lancet and test strip.

24. The apparatus of claim 1, wherein the re-orienting of the integrated lancet and test strip comprises flipping the integrated lancet and test strip.

25. The apparatus of claim 1, further including a transmission system for orienting said lancing/collecting assembly in a first position, whereby a lancet associated with said lancet-containing portion of said test strip can be used to form an opening in the skin of a patient, and in a second position, whereby a sensor associated with said sensor-containing portion of said test strip can be used to collect a sample of biological liquid from said patient.

26. The apparatus of claim 1, wherein the analyte comprises blood glucose.

* * * * *